United States Patent
Berme et al.

(10) Patent No.: US 9,066,667 B1
(45) Date of Patent: Jun. 30, 2015

(54) SYSTEM AND METHOD FOR TESTING DYNAMIC VISUAL ACUITY AND/OR GAZE STABILIZATION

(71) Applicant: Bertec Corporation, Columbus, OH (US)

(72) Inventors: Necip Berme, Worthington, OH (US); Kamran Barin, Columbus, OH (US); Daniel James Petit, Columbus, OH (US)

(73) Assignee: Bertec Corporation, Columbus, OH (US)

(*) Notice: Subject to any disclaimer, the term of this patent is extended or adjusted under 35 U.S.C. 154(b) by 0 days.

(21) Appl. No.: 14/535,117

(22) Filed: Nov. 6, 2014

(51) Int. Cl.
*A61B 3/02* (2006.01)
*A61B 3/00* (2006.01)
*A61B 3/032* (2006.01)

(52) U.S. Cl.
CPC ............... *A61B 3/032* (2013.01); *A61B 3/0033* (2013.01)

(58) Field of Classification Search
CPC ........ A61B 3/0091; A61B 3/02; A61B 3/032; A61B 3/036; A61B 3/11; A61B 3/113; A61B 3/145; A61H 5/005
USPC ......... 351/238, 200, 203–206, 208–211, 214, 351/221, 222, 233, 236, 243–246
See application file for complete search history.

(56) References Cited

U.S. PATENT DOCUMENTS

| | | | |
|---|---|---|---|
| 6,038,488 A | 3/2000 | Barnes et al. | |
| 6,113,237 A | 9/2000 | Ober et al. | |
| 6,152,564 A | 11/2000 | Ober et al. | |
| 6,295,878 B1 | 10/2001 | Berme | |
| 6,354,155 B1 | 3/2002 | Berme | |
| 6,389,883 B1 | 5/2002 | Berme et al. | |
| 6,936,016 B2 | 8/2005 | Berme et al. | |
| 7,195,355 B2 | 3/2007 | Nashner | |
| 7,500,752 B2 | 3/2009 | Nashner | |
| 8,181,541 B2 | 5/2012 | Berme | |
| 8,315,822 B2 | 11/2012 | Berme et al. | |
| 8,315,823 B2 | 11/2012 | Berme et al. | |
| D689,388 S | 9/2013 | Berme | |

(Continued)

OTHER PUBLICATIONS

Herdman, Susan J. et al., "Computerized Dynamic Visual Acuity Test in the Assessment of Vestibular Deficits", The American Journal of Otology, Inc., vol. 19, No. 6, 1998, pp. 790-796.

(Continued)

*Primary Examiner* — Stephone B Allen
*Assistant Examiner* — Brandi Thomas
(74) *Attorney, Agent, or Firm* — The Law Office of Patrick F. O'Reilly III, LLC

(57) ABSTRACT

A system for testing the vision of a subject is disclosed herein. The system includes a motion sensing device, the motion sensing device configured to measure a velocity or speed of a head of a subject; a visual display device having an output screen, the visual display device configured to display one or more visual objects on the output screen so that the one or more visual objects are visible to the subject; and a data processing device, the data processing device operatively coupled to the motion sensing device and the visual display device, the data processing device being specially programmed to carry out the steps of the vision tests. A method for the testing the vision of a subject is also disclosed herein. The vision tests may assess the dynamic visual acuity and/or the gaze stabilization of the subject.

26 Claims, 32 Drawing Sheets

(56) References Cited

U.S. PATENT DOCUMENTS

| | | |
|---|---|---|
| D689,389 S | 9/2013 | Berme |
| 8,543,540 B1 | 9/2013 | Wilson et al. |
| 8,544,347 B1 | 10/2013 | Berme |
| 8,643,669 B1 | 2/2014 | Wilson et al. |
| 8,700,569 B1 | 4/2014 | Wilson et al. |
| 8,704,855 B1 | 4/2014 | Berme et al. |
| 8,764,532 B1 | 7/2014 | Berme |
| 8,847,989 B1 * | 9/2014 | Berme et al. .................. 345/633 |
| D715,669 S | 10/2014 | Berme |
| 8,902,249 B1 | 12/2014 | Wilson et al. |
| 2003/0216656 A1 | 11/2003 | Berme et al. |
| 2008/0228110 A1 | 9/2008 | Berme |
| 2011/0277562 A1 | 11/2011 | Berme |
| 2012/0266648 A1 | 10/2012 | Berme et al. |
| 2012/0271565 A1 | 10/2012 | Berme et al. |
| 2014/0313488 A1 * | 10/2014 | Kiderman et al. ............ 351/246 |

OTHER PUBLICATIONS

Grassi, Massimo et al., "MLP: MATLAB toolbox for rapid and reliable auditory threshold estimation", Behavior Research Methods, 2009, 41(1), pp. 20-28.

\* cited by examiner

See Fig. 11B for Continuation

| Patient Information | | | |
|---|---|---|---|
| Name: Alex Barnes | | | Height: 6'5", Weight: N/A, BMI: N/A |
| Identifier: | | Sex: F | Date of Birth: 1994/04/05 |

Gaze Stabilization Test Report - Sep 11, 2014

| Trial Number | Target Velocity | Achieved Vel | Percent | Response | Trial Number | Target Velocity | Achieved Vel | Percent | Response |
|---|---|---|---|---|---|---|---|---|---|
| 1 | 90.0 | 93.7 | -- | correct | 1 | 90.0 | 84.4 | -- | correct |
| 2 | 170.0 | 163.1 | -- | incorrect | 2 | 170.0 | 176.2 | -- | incorrect |
| 3 | 130.0 | 129.1 | -- | correct | 3 | 130.0 | 129.2 | -- | correct |
| 4 | 150.0 | 155.4 | -- | correct | 4 | 150.0 | 147.2 | -- | incorrect |
| 5 | 160.0 | 168.6 | -- | incorrect | 5 | 140.0 | 136.6 | -- | incorrect |
| 6 | 150.0 | 153.1 | -- | correct | 6 | 130.0 | 120.9 | -- | correct |
| 7 | 160.0 | 159.1 | -- | incorrect | 7 | 140.0 | 132.8 | -- | correct |
| 8 | 150.0 | 143.3 | -- | correct | 8 | 140.0 | 139.6 | -- | correct |
| 9 | 160.0 | 158.3 | -- | correct | 9 | 140.0 | 132.7 | -- | correct |
| 10 | 160.0 | 155.8 | -- | incorrect | 10 | 140.0 | 131.9 | -- | correct |
| 11 | 160.0 | 164.1 | -- | correct | 11 | 140.0 | 141.6 | -- | correct |
| 12 | 160.0 | 161.6 | -- | incorrect | 12 | 140.0 | 145.0 | -- | correct |
| -- | -- | -- | -- | -- | 13 | 140.0 | 149.6 | -- | correct |
| -- | -- | -- | -- | -- | 14 | 140.0 | 130.4 | -- | correct |

Gaze Stabilization Left = 160 deg/s     Gaze Stabilization Right = 140 deg/s

FIG. 29B

SYSTEM AND METHOD FOR TESTING DYNAMIC VISUAL ACUITY AND/OR GAZE STABILIZATION

CROSS-REFERENCE TO RELATED APPLICATIONS

Not Applicable

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

1. Field of the Invention

The invention generally relates to a system and method for the testing the vision of a subject. More particularly, the invention relates to a system and method for testing the dynamic visual acuity and gaze stabilization of a subject.

2. Background

People maintain their upright posture and balance using inputs from proprioceptive, vestibular and visual systems. During normal daily activity, where dynamic balance is to be maintained, other factors also matter. These factors are visual acuity, reaction time, and muscle strength. Reaction time and muscle strength are important to be able to recover from a potential fall. Visual acuity is important to see a potential danger.

In general, a test for measuring visual acuity (VA) is concerned with measuring the acuteness or clearness of a subject's vision. A test that is specifically designed to measure a subject's dynamic visual acuity focuses on the subject's ability to visually discern fine details in an object while of the head of the subject is being displaced at a generally constant velocity, while a gaze stabilization test focuses on the ability of a subject to ascertain details of an object while his or her head is being displaced over a range of different velocities.

Conventional tests for measuring dynamic visual acuity and gaze stabilization require the distance from the subject to the display screen to be accurately determined. As such, either this distance must be measured each time the test is performed, or alternatively, the distance must be initially measured and then, the placement of the subject relative to display screen must always remain consistent in the testing room in order for the test results to be accurate (e.g., the chair on which the subject is seated during the test and the display screen on which the object is displayed must always be maintained a constant distance apart). Obviously, measuring the distance between the subject and the display screen each time the test is performed is both inconvenient and time consuming for the both the subject and the person performing the test. Also, determining the distance before the performance of each test is particularly problematic when subjects having disorders are being tested. These subjects are especially susceptible to easy fatigue. In addition, it is often very difficult, or even completely impractical, to always maintain a constant distance between each subject being tested and the display screen. After all, the visual testing system may comprise a portable type system that is moved from site to site, and set up in different locations each time the test is being performed. In such a portable situation, it is virtually impossible to maintain a constant distance between the location of the subject and the display screen. Thus, it is necessary to measure this distance each time the testing arrangement is set up. Even if the testing arrangement is not portable, and always in the same testing room, it is still very difficult to maintain a constant distance between the subject and the display screen. For example, if subjects are seated on a chair during the vision test and the chair is not fixed in place, subjects will most likely displace the chair when they get up from the seated position after completing the test, thereby shifting the position of the chair relative to the display screen. This movement of the chair will require the distance between the subject and display screen to be determined again.

What is needed, therefore, is a system and method for testing the dynamic visual acuity and gaze stabilization of a subject that does not require the measurement of the exact distance between the subject and the display screen. Moreover, a system and method for testing the dynamic visual acuity and gaze stabilization of a subject is needed that can be easily transported, and set up in different locations, without necessitating the measurement of the exact distance between the subject and the display screen at each of the different testing locations. Furthermore, a need exists for a system and method for testing the dynamic visual acuity and gaze stabilization of a subject that is capable of being quickly implemented, and produces accurate results as long as the relative location of the subject to the display screen remains generally constant during a particular test session.

BRIEF SUMMARY OF EMBODIMENTS OF THE INVENTION

Accordingly, the present invention is directed to a system and method for testing the dynamic visual acuity and gaze stabilization of a subject that substantially obviates one or more problems resulting from the limitations and deficiencies of the related art.

In accordance with one or more embodiments of the present invention, there is provided a system for testing the vision of a subject, which includes: a motion sensing device, the motion sensing device configured to measure a velocity or speed of a head of a subject; a visual display device having an output screen, the visual display device configured to display one or more visual objects on the output screen so that the one or more visual objects are visible to the subject; and a data processing device, the data processing device operatively coupled to the motion sensing device and the visual display device. The data processing device being specially programmed to display one or more configurations of one or more visual objects having a first initial size on the output screen of the visual display device while the subject maintains a generally fixed position of his or her head; determine whether or not the subject correctly identifies the one or more configurations of the one or more visual objects having the first initial size; incrementally decrease and/or increase the size of the one or more visual objects on the output screen of the visual display device during a first set of successive trials, and determine whether or not the subject correctly identifies one or more configurations of each of the differently sized visual objects during the first set of successive trials while the subject maintains a generally fixed position of his or her head;

determine a size parameter of a first threshold version of the one or more visual objects based upon a performance of the subject during the first set of successive trials during which the subject maintains the generally fixed position of his or her head, wherein the determination of the size parameter of the first threshold version of the one or more visual objects does not require the exact distance between the subject and the visual display device to be measured or determined; display one or more configurations of the one or more visual objects having a second initial size on the output screen of the visual display device while the subject's head undergoes displacement at a velocity or speed within a predetermined range as measured by the motion sensing device; determine whether or not the subject correctly identifies the one or more configurations of the one or more visual objects having the second initial size; incrementally decrease and/or increase the size of the one or more visual objects on the output screen of the visual display device during a second set of successive trials, and determine whether or not the subject correctly identifies one or more configurations of each of the differently sized visual objects during the second set of successive trials when the subject's head undergoes displacement at a velocity or speed within the predetermined range as measured by the motion sensing device; determine a size parameter of a second threshold version of the one or more visual objects based upon a performance of the subject during the second set of successive trials during which the subject's head undergoes displacement; compare the size parameter of the second threshold version of the one or more visual objects to the size parameter of the first threshold version of the one or more visual objects; and generate a quantitative assessment of dynamic visual acuity loss using the size parameters of the first and second threshold versions of the one or more visual objects.

In a further embodiment of this aspect of the present invention, the motion sensing device comprises at least one of an accelerometer, a gyroscope, and a magnetometer.

In yet a further embodiment, the motion sensing device is configured to be attached to the head of the subject by means of an adjustable band.

In still a further embodiment, the system further comprises a user input device, the user input device configured to output an input signal in response to a manipulation of the user input device by a system user, the user input device being operatively coupled to the data processing device. The determination of whether or not the subject correctly identifies the one or more configurations of the one or more visual objects during the first and second successive trials is based upon the input signal from the user input device.

In yet a further embodiment, the user input device comprises at least one of: (i) a mouse, (ii) a keyboard, (iii) a clicking device, (iv) a voice recognition device, and (v) a joystick.

In still a further embodiment, the one or more visual objects displayed on the output screen of the visual display device comprise one or more optotypes, the one or more optotypes comprising at least one of: (i) a Tumbling E, (ii) a Landolt C, (iii) different letters of a recognized alphabet, and (iv) any other identifiable symbol.

In yet a further embodiment, the second initial size of the one or more visual objects is equal to the first initial size of the one or more visual objects or the second initial size of the one or more visual objects is larger than the first initial size of the one or more visual objects.

In still a further embodiment, during the second set of successive trials, the data processing device is further specially programmed to generate and display a visual indicator on the output screen of the visual display device that indicates whether or not the velocity or speed at which the subject's head is being displaced lies within the predetermined range.

In yet a further embodiment, the data processing device is further specially programmed to generate a practice mode for the second set of successive trials during which the subject's head undergoes displacement; and wherein, during the practice mode, the data processing device is specially programmed to generate and display a visual indicator on the output screen of the visual display device that indicates whether or not the head of the subject is being displaced within a prescribed range of motion.

In still a further embodiment, the system further comprises an auditory output device operatively coupled to the data processing device; and wherein, during the second set of successive trials, the data processing device is further specially programmed to generate and output an audible cue configured to assist the subject in achieving a head velocity or speed that lies within the predetermined range.

In yet a further embodiment, the one or more configurations of the one or more visual objects displayed on the output screen of the visual display device by the data processing device comprise a series of different visual objects displayed in succession on the output screen of the visual display device.

In accordance with one or more other embodiments of the present invention, there is provided a system for testing the vision of a subject, which includes: a motion sensing device, the motion sensing device configured to measure a velocity or speed of a head of a subject; a visual display device having an output screen, the visual display device configured to display one or more visual objects on the output screen so that the one or more visual objects are visible to the subject; and a data processing device, the data processing device operatively coupled to the motion sensing device and the visual display device. The data processing device being specially programmed to display one or more configurations of one or more visual objects having a first initial size on the output screen of the visual display device while the subject maintains a generally fixed position of his or her head; determine whether or not the subject correctly identifies the one or more configurations of the one or more visual objects having the first initial size; incrementally decrease and/or increase the size of the one or more visual objects on the output screen of the visual display device during a first set of successive trials, and determine whether or not the subject correctly identifies one or more configurations of each of the differently sized visual objects during the first set of successive trials while the subject maintains a generally fixed position of his or her head; determine a size parameter of a first threshold version of the one or more visual objects based upon a performance of the subject during the first set of successive trials during which the subject maintains the generally fixed position of his or her head, wherein the determination of the size parameter of the first threshold version of the one or more visual objects does not require the exact distance between the subject and the visual display device to be measured or determined; display one or more configurations of the one or more visual objects having a second initial size on the output screen of the visual display device while the subject's head undergoes displacement at a velocity or speed within a predetermined range as measured by the motion sensing device; determine whether or not the subject correctly identifies the one or more configurations of the one or more visual objects having the second initial size; incrementally decrease and/or increase the predetermined velocity or speed range within which the subject's head is to be displaced while the subject identifies one or more configurations of the one or more visual objects during a second set of successive trials, and determine whether or not the subject correctly identifies the one or more configurations of the one or more visual objects for each of the predetermined velocity or speed ranges during the second set of successive trials, the velocity or speed of the head of the subject being measured by the motion sensing device; compute a maximum head velocity or head speed at which the subject is capable of correctly identifying one or more configurations of the one or more visual objects; and generate a quantitative assessment of gaze stabilization based upon the computed maximum head velocity or head speed at which the subject is capable of correctly identifying one or more configurations of the one or more visual objects.

In a further embodiment of this aspect of the present invention, the one or more visual objects displayed on the output screen of the visual display device comprise one or more optotypes, the one or more optotypes comprising at least one of: (i) a Tumbling E, (ii) a Landolt C, (iii) different letters of a recognized alphabet, and (iv) any other identifiable symbol.

In yet a further embodiment, the second initial size of the one or more visual objects is equal to the first initial size of the one or more visual objects or the second initial size of the one or more visual objects is larger than the first initial size of the one or more visual objects.

In still a further embodiment, during the second set of successive trials, the data processing device is further specially programmed to generate and display a visual indicator on the output screen of the visual display device that indicates whether or not the velocity or speed at which the subject's head is being displaced lies within the predetermined range.

In yet a further embodiment, the system further comprises an auditory output device operatively coupled to the data processing device; and wherein, during the second set of successive trials, the data processing device is further specially programmed to generate and output an audible cue configured to assist the subject in achieving a head velocity or speed that lies within the predetermined range.

In still a further embodiment, the one or more configurations of the one or more visual objects displayed on the output screen of the visual display device by the data processing device comprise a series of different visual objects displayed in succession on the output screen of the visual display device.

In accordance with yet one or more other embodiments of the present invention, there is provided a method for testing the vision of a subject, the method comprising the steps of: (i) providing a motion sensing device, the motion sensing device configured to measure a velocity or speed of the head of the subject; (ii) providing a visual display device having an output screen, the visual display device configured to display one or more visual objects on the output screen so that the one or more visual objects are visible to the subject; (iii) providing a data processing device, the data processing device operatively coupled to the motion sensing device and the visual display device; (iv) positioning the subject in front of the output screen of the visual display device such that one or more visual objects are visible to the subject; (v) displaying one or more configurations of the one or more visual objects having a first initial size on the output screen of the visual display device while the subject maintains a generally fixed position of his or her head; (vi) determining, by using the data processing device, whether or not the subject correctly identifies the one or more configurations of the one or more visual objects having the first initial size; (vii) incrementally decreasing and/or increasing the size of the one or more visual objects on the output screen of the visual display device using the data processing device during a first set of successive trials, and determining whether or not the subject correctly identifies one or more configurations of each of the differently sized visual objects during the first set of successive trials; (viii) determining, by using the data processing device, a size parameter of a first threshold version of the one or more visual objects based upon a performance of the subject during the first set of successive trials during which the subject maintains the generally fixed position of his or her head, wherein the determination of the size parameter of the first threshold version of the one or more visual objects does not require the exact distance between the subject and the visual display device to be measured or determined; (ix) displaying one or more configurations of the one or more visual objects having a second initial size on the output screen of the visual display device when the subject's head undergoes displacement at a velocity or speed within a predetermined range as measured by the motion sensing device; (x) determining, by using the data processing device, whether or not the subject correctly identifies the one or more configurations of the one or more visual objects having the second initial size; (xi) incrementally decreasing and/or increasing the size of the one or more visual objects on the output screen of the visual display device using the data processing device during a second set of successive trials, and determining whether or not the subject correctly identifies one or more configurations of each of the differently sized visual objects during the second set of successive trials when the subject's head undergoes displacement at a velocity or speed within the predetermined range as measured by the motion sensing device; (xii) determining, by using the data processing device, a size parameter of a second threshold version of the one or more visual objects based upon a performance of the subject during the second set of successive trials during which the subject's head undergoes displacement; (xiii) comparing, by using the data processing device, the size parameter of the second threshold version of the one or more visual objects to the size parameter of the first threshold version of the one or more visual objects; (xiv) generating, by using the data processing device, a quantitative assessment of dynamic visual acuity loss using the size parameters of the first and second threshold versions of the one or more visual objects; (xv) outputting the quantitative assessment of dynamic visual acuity loss of the subject on the output screen of the visual display device; (xvi) displaying one or more configurations of the one or more visual objects having a third initial size on the output screen of the visual display device when the subject's head undergoes displacement at a velocity or speed within a predetermined range as measured by the motion sensing device, (xvii) determining, by using the data processing device, whether or not the subject correctly identifies the one or more configurations of the one or more visual objects having the third initial size; (xviii) incrementally decreasing and/or increasing, using the data processing device, the predetermined velocity or speed range within which the subject's head is to be displaced while identifying one or more configurations of the one or more visual objects during a third set of successive trials, and determining whether or not the subject correctly identifies the one or more configurations of the one or more visual objects for each of the predetermined velocity or speed ranges during the third set of successive trials, the velocity or speed of the head of the subject being measured by the motion sensing device; (xix) computing, by using the data processing device, a maximum head velocity or head speed at which the subject is capable of correctly identifying one or more configurations of the one or more visual objects; (xx) generating, by using the data processing device, a quantitative assessment of gaze stabilization based upon the computed maximum head velocity or head speed at which the subject is capable of correctly identifying the one or more configurations of the one or more visual objects; and (xxi) outputting the quantitative assessment of gaze stabilization of the subject on the output screen of the visual display device.

In a further embodiment of this aspect of the present invention, the one or more configurations of the one or more visual objects are only displayed on the output screen of the visual display device during the second set or third set of successive trials when the data processing device determines that the subject's head is undergoing displacement at a velocity or speed that lies within the predetermined range.

In yet a further embodiment, a user input device is additionally provided, the user input device configured to output an input signal in response to a manipulation of the user input device by a system user, the user input device being operatively coupled to the data processing device. In this further embodiment, the method further includes the step of inputting a response of the subject regarding the configuration of the one or more visual objects into the user input device, outputting an input signal from the user input device that is indicative of the response of the subject, and transmitting the input signal of the user input device to the data processing device so that the data processing device is capable of determining whether or not the subject has correctly identified a configuration of the one or more visual objects based upon the response of the subject.

In still a further embodiment, the user input device is configured to accept at least four different responses of a subject, each of the at least four different responses of the subject corresponding to a different configuration of the one or more visual objects.

In yet a further embodiment, the method further comprises the step of computing, by using the data processing device, the logarithm of the ratio of the size parameter of the second threshold version of the one or more visual objects to the size parameter of the first threshold version of the one or more visual objects.

In still a further embodiment, the computed logarithm comprises a base 10 logarithm.

In yet a further embodiment, a static visual acuity of the subject is not determined in carrying out the steps of the method.

In still a further embodiment, an exact distance between the subject and the visual display device is not measured or determined in carrying out the steps of the method.

In yet a further embodiment, a Snellen fraction is not determined in carrying out the steps of the method.

It is to be understood that the foregoing summary and the following detailed description of the present invention are merely exemplary and explanatory in nature. As such, the foregoing summary and the following detailed description of the invention should not be construed to limit the scope of the appended claims in any sense.

BRIEF DESCRIPTION OF THE SEVERAL VIEWS OF THE DRAWINGS

The invention will now be described, by way of example, with reference to the accompanying drawings, in which:

FIG. 29B is an eighth exemplary operator screen image of the visual display device, which illustrates a second part of an exemplary report generated by the vision testing system for displaying the results from a gaze stabilization test, according to an embodiment of the invention.

Throughout the figures, the same components/steps are always denoted using the same reference characters so that, as a general rule, they will only be described once.

DETAILED DESCRIPTION OF EMBODIMENTS OF THE INVENTION

The present invention is described herein, in an exemplary manner, with reference to computer system architecture and flowcharts that illustrate exemplary processes carried out by the computer system. In one or more embodiments, functional blocks of the flowchart illustrations can be implemented by computer system instructions. These computer program instructions may be loaded directly onto an internal data storage device of a computing device (e.g., a hard drive of a computer). Alternatively, these computer program instructions could be stored on a portable computer-readable medium (e.g., a flash drive, a floppy disk, a compact disk, etc.), and then subsequently loaded onto a computing device such that the instructions can be executed thereby. In other embodiments, these computer program instructions could be embodied in the hardware of the computing device, rather than in the software thereof. It is also possible for the computer program instructions to be embodied in a combination of both the hardware and the software.

This description describes in general form the computer program(s) required to carry out the dynamic visual acuity and gaze stabilization testing of a subject. Any competent programmer in the field of information technology could develop a system using the description set forth herein.

For the sake of brevity, conventional computer system components, conventional data networking, and conventional software coding will not be described in detail herein. Also, it is to be understood that the connecting lines shown in the block diagram(s) included herein are intended to represent functional relationships and/or operational couplings between the various components. Similarly, connecting lines are also used between the elements of the flowcharts in order to illustrate the functional relationships therebetween. In addition to that which is explicitly depicted, it is to be understood that many alternative or additional functional relationships and/or physical connections may be incorporated in a practical application of the system.

1. Exemplary Vision Testing Systems

Figure 1:
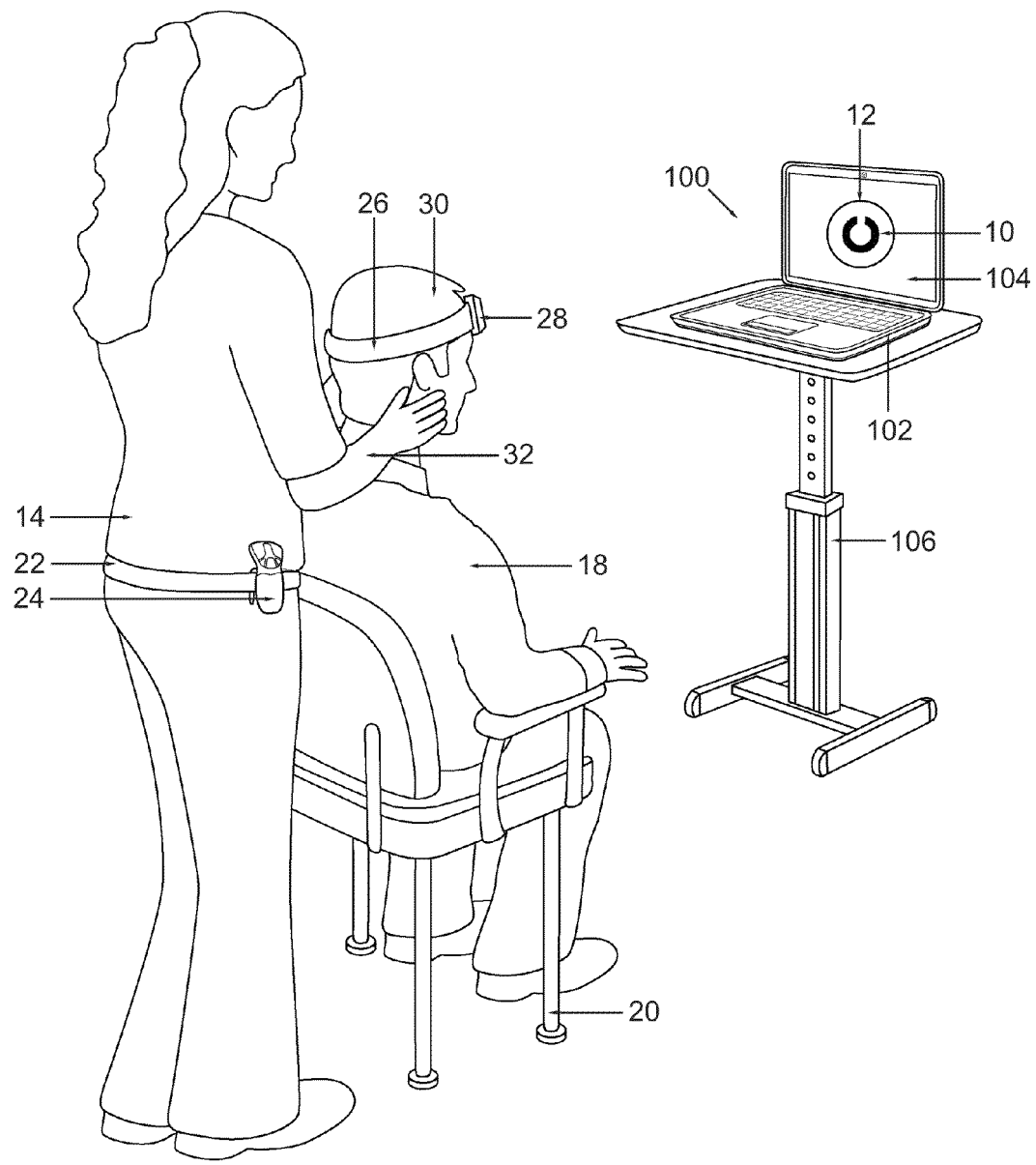
FIG. 1 is a diagrammatic perspective view of a first exemplary vision testing system that utilizes a laptop computing device, according to one embodiment of the invention.

A first exemplary embodiment of a vision testing system is seen generally at 100 in FIG. 1. In the illustrative embodiment, the vision testing system 100 generally comprises a laptop computing device 102 with a visual display device 104. The laptop computing device 102 is one exemplary form of a data processing device and/or data processing and data acquisition device. In FIG. 1, the laptop computing device 102 is disposed on an adjustable height table 106 so that the height of the laptop computing device 102 is selectively adjustable by a user. In one or more embodiments, the height of the table 106 is adjusted prior to each test session such that the center of the visual display device 104 of the laptop computing device 102, which contains the one or more visual objects 10, is generally horizontally aligned with the eyes of the subject 18 (i.e., so the subject 18 is looking straight at the visual object 10 on the visual display device 104 during the testing).

The one or more visual objects 10 (e.g., optotypes), which the subject identifies during each vision test described herein, are displayed on the visual display device 104 of the laptop computing device 102 in the first exemplary embodiment. Specifically, as shown in FIG. 1, the visual object 10 is displayed on the output screen of the laptop visual display device 104 within a circle 12. The circle 12 circumscribes the visual object 10 and focuses the attention of the subject 18 on the central region of the output screen containing the visual object 10.

While a circle 12 is used to circumscribe the visual object 10 in the exemplary embodiment of FIG. 1, it is to be understood that other suitable shapes could be used to circumscribe the visual object 10 as well. For example, the visual object 10 may be alternatively circumscribed by a square or rectangle, as these shapes are also capable of effectively focusing the subject's attention on the central region of the output screen of the visual display device 104 containing the visual object 10.

In addition, while the visual object 10 in FIG. 1 is in the form of a Landolt C optotype, it is to be understood that other suitable visual objects 10 may be used in place of the Landolt C. For example, the visual object 10 alternatively may comprise a Tumbling E optotype or an optotype comprising different letters of a recognized alphabet (e.g., different letters of the English alphabet). That is, in some embodiments, the subject 18 may identify different letters of a recognized alphabet, rather than different orientations of the same letter or optotype. Also, in other embodiments, the visual object 10 alternatively may comprise any other identifiable symbol (e.g., a crescent, a star, etc.).

In one or more embodiments, different letters or objects may be displayed in succession during a particular test (e.g., during the dynamic visual acuity (DVA) test or gaze stabilization test (GST) described hereinafter). For example, during a particular test, a Tumbling E optotype may be displayed first, then followed by the letter "K", a crescent symbol, a star symbol, etc. In this exemplary fashion, the letters that are displayed to the subject 18 can be consistently varied during the performance of the testing.

Referring again to FIG. 1, it can be seen that the head 30 of the subject 18 is fitted with a motion sensing device 28 disposed thereon. In particular, in the illustrative embodiment, the motion sensing device 28 is removably coupled to the head of the subject 18 using a stretchable, elastic headband 26 (i.e., a resilient band 26). The motion sensing device 28 is configured to measure a velocity or speed of the head 30 of the subject 18 when the head 30 of the subject 18 is displaced during the latter portion of the dynamic visual acuity (DVA) and gaze stabilization tests described herein. That is, the motion sensing device 28 determines the angular displacement and velocity of the subject's head 30 during the latter portions of the dynamic visual acuity (DVA) and gaze stabilization tests (e.g., the angular velocity of the subject's head 30 in degrees per second). In one or more embodiments, the motion sensing device 28 comprises at least one of an accelerometer and a gyroscope.

In an exemplary embodiment, the motion sensing device 28 may comprise a three-dimensional motion sensing device (i.e., an inertial measurement unit (IMU)) having a 3-axis accelerometer, a 3-axis rate gyro, and a 3-axis compass (i.e., a 3-axis magnetometer). Also, the exemplary motion sensing device 28 may comprise a wireless data connection to the laptop computing device 102. In particular, the laptop computing device 102 may comprise a data transmission interface unit that is operatively connected to one of the output ports of the laptop computing device 102, such as the universal serial bus (USB) port of the laptop computing device 102. As such, the laptop computing device 102 provided with the data transmission interface unit wirelessly communicates with the motion sensing device 28 using a local wireless network. In addition, the exemplary motion sensing device 28 is both lightweight (e.g., less than 30 grams) and compact in size (e.g., less than 40 mm by 70 mm by 20 mm) so that it is generally comfortable for the subject 18 to wear on his or her head 30.

Next, referring to FIG. 10, an explanation of the three (3) directions of head rotation that the motion sensing device 28 is capable of detecting will be described. First, the motion sensing device 28 is configured to detect the rotation of the head 30 of the subject 18 about the yaw axis 66 of rotation as indicated by the curved arrow 72 in FIG. 10. The curved arrow 72 about the yaw axis 66 indicates the common side-to-side movement of the subject's head 30 during the vision testing. Secondly, the motion sensing device 28 is configured to detect the rotation of the head 30 of the subject 18 about the pitch axis 62 of rotation as indicated by the curved arrow 68 in FIG. 10. The curved arrow 68 about the pitch axis 62 indicates the up-and-down movement of the subject's head 30 during the vision testing. Thirdly, the motion sensing device 28 is configured to detect the rotation of the head 30 of the subject 18 about the roll axis 64 of rotation as indicated by the curved arrow 70 in FIG. 10. The curved arrow 70 about the roll axis 64 indicates the tilt-right and tilt-left movement of the subject's head 30 during the vision testing. In addition to the ability to determine head rotation about all three (3) axes of rotation, the use of a three-dimensional motion sensing device 28 advantageously permits the determination of whether the subject 18 is rotating his or her head 30 purely about the desired axis of rotation (e.g., the yaw axis) or whether there is also off-axis rotation of the subject's head 30 during the prescribed rotation (e.g., the subject is rotating his or head 30 about a combination of the yaw axis and the roll axis, or about a combination of the yaw axis and the pitch axis). Because off-axis rotation may adversely affect the accuracy of the vision testing results, it is important to determine if off-axis rotation is present during the vision testing of the subject 18. The utilization of a three-dimensional motion sensing device 28 enables the determination of this off-axis rotation.

Now, an illustrative manner in which the computing device 102, 202, 302 of the vision testing system 100, 200, 300 performs the head rotation calculations from the output of the motion sensing device 28 will be explained in detail. In particular, this calculation procedure will describe the manner in which the angular position and the angular velocity of the head of the subject 18 may be determined using the signals from the motion sensing device 28 (i.e., the head-mounted IMU) of the vision testing system 100, 200, 300. As explained above, in one or more embodiments, the motion sensing device 28 may be in the form of an IMU, which includes the following three triaxial sensor devices: (i) a three-axis accelerometer sensing linear acceleration $\vec{a}\,'$, (ii) a three-axis rate gyroscope sensing angular velocity $\vec{\omega}\,'$, and (iii) a three-axis magnetometer sensing the magnetic north vector $\vec{n}\,'$. The motion sensing device 28 (i.e., the IMU) senses in the local (primed) frame of reference attached to the IMU itself. Because each of the sensor devices in the IMU is triaxial, the vectors $\vec{a}'$, $\vec{\omega}'$, $\vec{n}'$ are each 3-component vectors. A prime symbol is used in conjunction with each of these vectors to symbolize that the measurements are taken in accordance with the local reference frame. The unprimed vectors that will be described hereinafter are in the global reference frame.

The objective of these calculations is to find the angular position or orientation $\vec{\theta}(t)$ and the angular velocity $\vec{\omega}(t)$ of the head of the subject 18 in the global, unprimed, inertial frame of reference. The initial orientation in the global frame of reference may be either known in advance or derived from $\vec{\Theta}_0$, as will be explained below with regard to the rotation transformation matrix.

For the purposes of the calculation procedure, a right-handed coordinate system is assumed for both global and local frames of reference. The global frame of reference is attached to the Earth. The acceleration due to gravity is assumed to be a constant vector $\vec{g}$. Also, for the purposes of the calculations presented herein, it is presumed the sensor devices of the inertial measurement unit (IMU) provide calibrated data. In addition, all of the one or more output signals from the IMU are treated as continuous functions of time. Although, it is to be understood the general form of the equations described herein may be readily discretized to account for IMU sensor devices that take discrete time samples from a bandwidth-limited continuous signal.

The angular velocity $\vec{\omega}(t)$ of the subject's head rotation is obtained by coordinate transformation using the IMU output signal(s) as follows:

$$\vec{\omega}(t) = \vec{\Theta}(t)\vec{\omega}'(t) \quad (1)$$

where $\vec{\Theta}(t)$ is the matrix of the rotation transformation that rotates the instantaneous local frame of reference into the global frame of reference.

The orientation $\vec{\theta}(t)$ of the subject's head rotation is obtained by single integration of the angular velocity using the IMU output signal(s) as follows:

$$\vec{\theta}(t) = \vec{\theta}_0 + \int_0^t \vec{\omega}(t) dt \quad (2)$$

$$\vec{\theta}(t) = \vec{\theta}_0 + \int_0^t \vec{\Theta}(t)\vec{\omega}'(t) dt \quad (3)$$

There are two aspects to the coordinate transformation matrix $\vec{\Theta}(t)$ calculation: (i) the initial value $\vec{\Theta}_0 = \vec{\Theta}(0)$ at t=0 and (ii) subsequent updates to this value. The updates may be integrated from the angular velocity, i.e., the time derivative $\dot{\Theta}$ of the rotation transformation matrix may be set as a function of the angular velocity, and then the coordinate transformation matrix becomes:

$$\vec{\Theta}(t) = \int_0^t \dot{\Theta}(\tau, \vec{\omega}'(\tau)) d\tau \quad (4)$$

The value at any point in time may be derived from known local and global values of both the magnetic north vector and the acceleration of gravity. Those two vectors are usually non-parallel. This is the requirement for the $\vec{\Theta}(\vec{g}', \vec{n}', \vec{g}, \vec{n})$ to be unique. The knowledge of either of those vectors in isolation gives a family of non-unique solutions $\vec{\Theta}(\vec{g}', \vec{g})$ or $\vec{\Theta}(\vec{n}', \vec{n})$. Both are unconstrained in one component of rotation. The $\vec{\Theta}(\vec{g}', \vec{n}', \vec{g}, \vec{n})$ has many known implementations, with the common one being the Kabsch algorithm.

In one or more embodiments, if a known starting global orientation is assumed, and the time-derivative of the rotation transformation matrix as a function of the angular velocity in the local frame is used, it is possible to obtain the matrix without the need for the accelerometer and magnetometer in the IMU.

Advantageously, in one or more embodiments, the motion sensing device 28 described above requires no manual calibration step or setup time, other than putting the device 28 on the head 30 of the subject 18. That is, there is no required manual calibration and/or tare step (e.g., to calibrate the accelerometer with respect to gravity and/or to zero the gyroscope) that must be performed prior to the execution of each particular test (i.e., a DVA or GST test). Obviating the need for manual calibration and/or a manual tare step advantageously saves valuable time during the execution of a particular test series. In order to avoid these laborious and tedious manual steps, at the beginning of every dynamic visual acuity (DVA) and gaze stabilization test (GST) trial, the motion sensing device 28 (i.e., inertial measurement unit 28) is automatically re-tared (or re-zeroed) to the subject's head position at that time by the computing device 102, 202, 302. With each of these zeroing events, the computing device 102, 202, 302 also checks the orientation of the motion sensing device 28 in order to make sure that it is on the subject's head 30 correctly and/or to make sure the subject 18 is still and has his or her head held in the correct orientation. The computing device 102, 202, 302 checks the orientation of the motion sensing device 28 by using the data from the linear accelerometer, and by determining which axis the gravity vector lies in. If the computing device 102, 202, 302 detects no issues with the orientation of the motion sensing device 28, nothing happens on the subject or clinician screen (i.e., no message is displayed in order to save time). Conversely, if the computing device 102, 202, 302 determines that there is a problem with the orientation of the motion sensing device 28, a flag pops up on the operator or clinician screen and the test will not begin (i.e., the DVA or GST test will not begin). In order to begin the test, the clinician must adjust the motion sensing device 28 or the subject's head 30 to the correct position and press "okay" on the keyboard 206, 306 of the computing device 102, 202, 302 to dismiss the flag. Upon the "okay" input, the motion sensing device 28 will tare to its position at that time and the test will begin. In these one or more embodiments, the flag only pops up once per trial.

Also, advantageously, in these one or more embodiments, the motion sensing device 28 does not require a flat and/or still surface for using the motion sensing device 28 (i.e., the inertial measurement unit). In addition, in these one or more embodiments, the motion sensing device 28 does not comprise an electrical cord that operatively connects it to the computing device 102, 202, 302. That is, the motion sensing device 28 is wirelessly coupled to the computing device 102, 202, 302 without the use of any electrical wires. Because the motion sensing device 28 is not tethered (i.e., it contains no electrical cord), it can advantageously accommodate various configurations and distances from the computing device 102, 202, 302. In other words, the configuration of the vision testing system 100, 200, 300 in a room is not limited by the physical limitations imposed upon the system 100, 200, 300 by the fixed length of an electrical cord connecting the motion sensing device 28 to the computing device 102, 202, 302 (e.g., the electrical cord of a tethered motion sensing device 28 may be too short to accommodate a desired testing configuration).

Referring again to FIG. 1, it can be seen that a clinician 14 is standing behind a subject 18 seated on a chair 20. During the latter portion of the vision tests described herein, wherein the subject's head 30 is to be displaced back-and-forth, the clinician 14 may move the subject's head 30 using her arms 32 so that the velocity and range of motion of the subject's head 30 is capable of being more accurately controlled. Alternatively, the subject 18 can move his own head 30 without the assistance of the clinician 14 during these portions of the test.

As shown in the illustrative embodiment of FIG. 1, it can also be seen that the clinician 14 is provided with a user input device 24 attached to her waist via a belt or elastic band 22. The user input device 24 is configured to output an input signal in response to a manipulation of the user input device by a system user (i.e., the clinician 14). In the illustrative embodiment, the user input device 24 is operatively coupled to the laptop computing device 102 by wireless data transmission means. For example, the user input device 24 may comprise a wireless mouse that wirelessly communicates with the laptop computing device 102. In other embodiments, the user input device may alternatively comprise (i) a keyboard (e.g., the keyboard of the laptop computing device 102 in FIG. 1 or the separate keyboards 206, 306 in FIGS. 2 and 3), (ii) a wireless clicking device, or (iii) a voice recognition device that allows the clinician 14 and/or the subject 18 to verbally input the subject's response (e.g., to record the subject's perceived orientation of the optotype).

Figure 5:
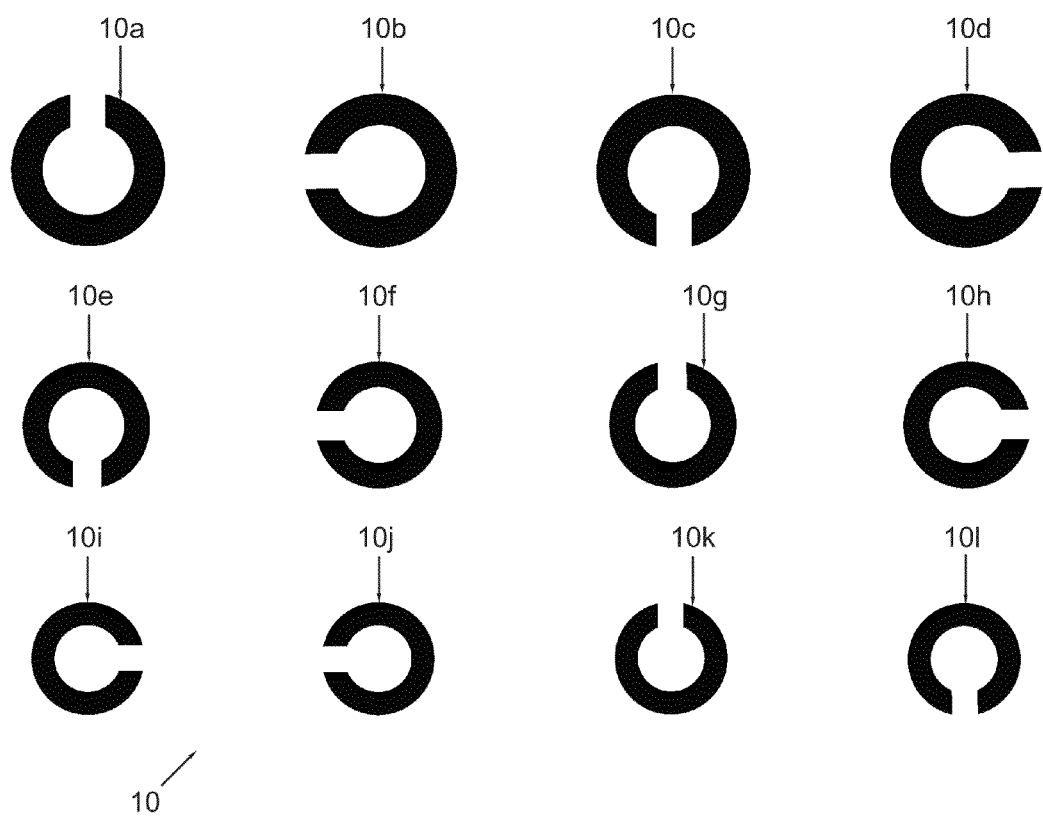
FIG. 5 is an illustration of a first exemplary type of optotype that may be utilized in the embodiments of the vision testing system described herein.

During the vision testing of the subject 18, after the subject 18 identifies the perceived configuration of the visual object 10 that is displayed on the visual display device 104, the clinician 14 may use the user input device 24 in order to enter and transmit the subject's response (i.e., the perceived configuration of the visual object 10) to the laptop computing device 102. In one or more embodiments, the user input device 24 is configured to accept at least four different responses of the subject 18, wherein each of the at least four different responses of the subject 18 correspond to different configurations of the visual object 10. For example, turning to FIG. 5, it can be seen that, if the visual object 10 is in the form of a Landolt C optotype, a first configuration of the visual object 10a is one in which the Landolt C is pointing up (see the top row of FIG. 5), a second configuration of the visual object 10b is one in which the Landolt C is pointing to the left, a third configuration of the visual object 10c is one in which the Landolt C is pointing down, and a fourth configuration of the visual object 10d is one in which the Landolt C is pointing to the right. Then, referring to the middle row of FIG. 5, it can be seen that these same four configurations of the Landolt C can be displayed on the visual display device 104 in a smaller overall size (e.g., Landolt C optotypes 10e, 10f, 10g, 10h). Finally, with reference to the bottom row of FIG. 5, it can be seen that these same four configurations of the Landolt C can be displayed on the visual display device 104 in an even smaller overall size (e.g., Landolt C optotypes 10i, 10j, 10k, 10l). In addition to those optotypes explicitly illustrated in FIG. 5, it is to be understood that at least four (4) other configurations of the Landolt C optotype are possible, namely configurations of the Landolt C optotype pointing in each of the four forty-five (45) degree angular positions (i.e., pointing up and to the left, pointing up and to the right, pointing down and to the left, and pointing down and to the right).

Figure 6:
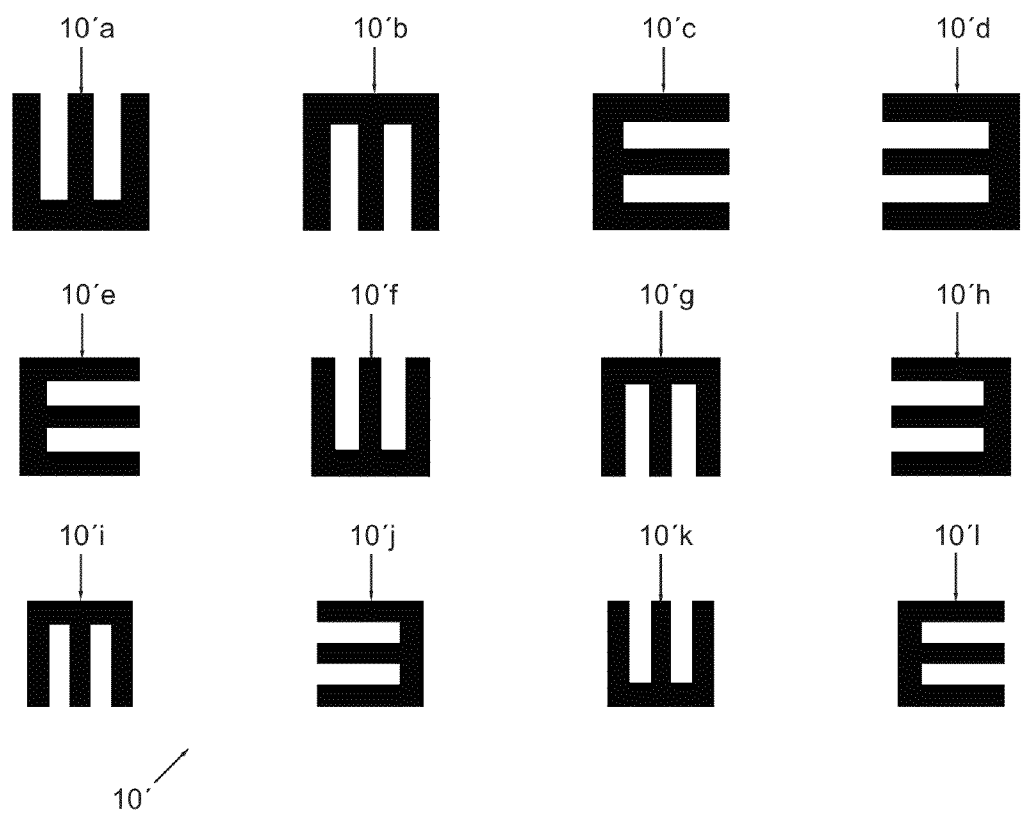
FIG. 6 is an illustration of a second exemplary type of optotype that may be utilized in the embodiments of the vision testing system described herein.

As another example, referring to FIG. 6, it can be seen that, if the visual object 10' is in the form of a Tumbling E optotype, a first configuration of the visual object 10'a is one in which the Tumbling E is pointing up (see the top row of FIG. 6), a second configuration of the visual object 10'b is one in which the Tumbling E is pointing down, a third configuration of the visual object 10'c is one in which the Tumbling E is pointing to the right, and a fourth configuration of the visual object 10'd is one in which the Tumbling E is pointing to the left.

Next, referring to the middle row of FIG. 6, it can be seen that these same four configurations of the Tumbling E can be displayed on the visual display device 104 in a smaller overall size (e.g., Tumbling E optotypes 10'e, 10'f, 10'g, 10'h). Finally, with reference to bottom row of FIG. 6, it can be seen that these same four configurations of the Tumbling E can be displayed on the visual display device 104 in an even smaller overall size (e.g., Tumbling E optotypes 10'i, 10'j, 10'k, 10'l).

Figure 2:
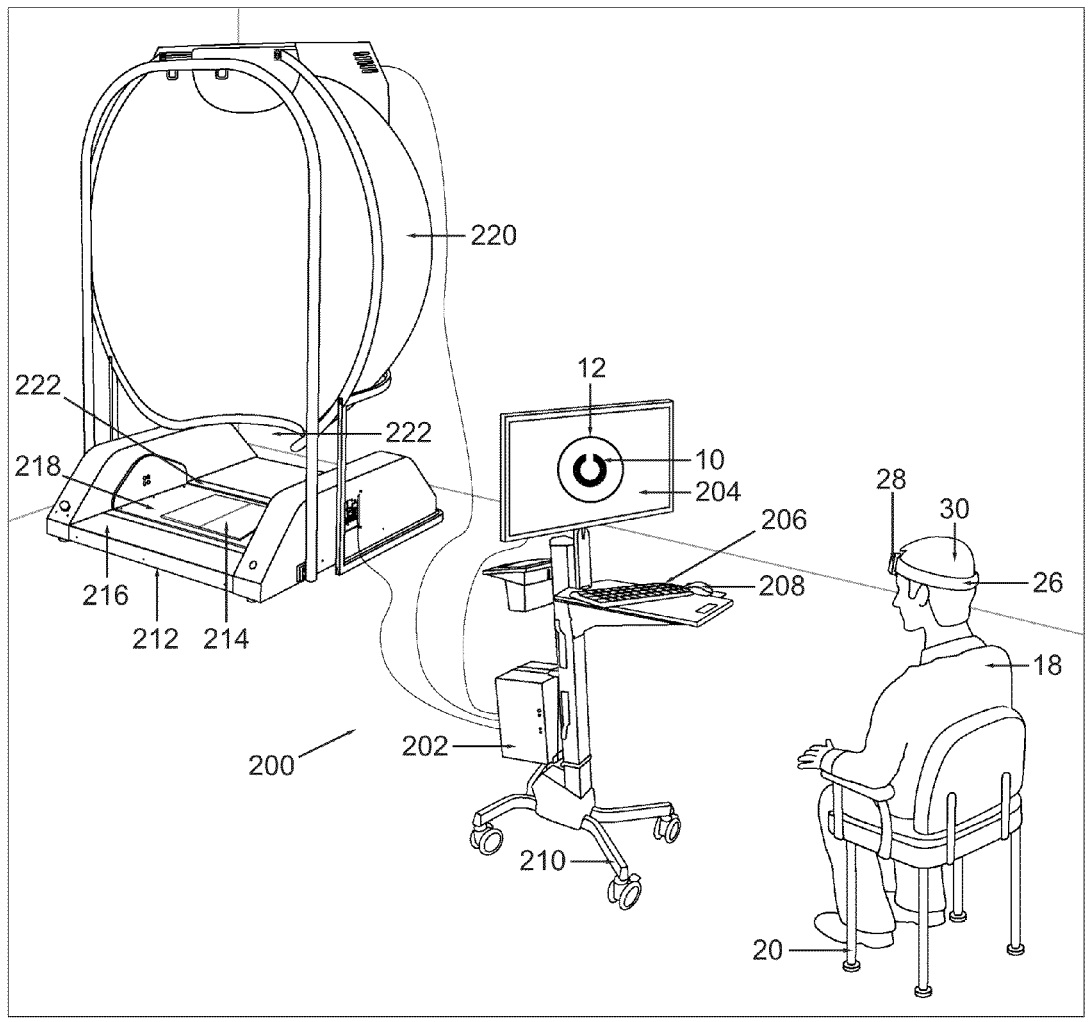
FIG. 2 is a diagrammatic perspective view of a second exemplary vision testing system that utilizes a computing device disposed on a movable cart, according to another embodiment of the invention.

A second exemplary embodiment of a vision testing system is seen generally at 200 in FIG. 2. Referring to this figure, it can be seen that, in some respects, the second exemplary embodiment is similar to that of the first embodiment. Moreover, some elements are common to both such embodiments. For the sake of brevity, the parts that the second embodiment of the vision testing system has in common with the first embodiment will only be briefly mentioned, if at all, because these components have already been explained in detail above. Furthermore, in the interest of clarity, these components will be denoted using the same reference characters that were used in the first embodiment.

In the illustrative embodiment of FIG. 2, the vision testing system 200 generally comprises a computing device 202 (i.e., a data processing device or a data acquisition and processing device that is capable of collecting, storing, and processing data), which in turn, is operatively coupled to a first visual display device 204, a force measurement assembly 212, and a second visual display device 220. In FIG. 2, the first visual display device 204 is disposed on an adjustable height cart 210 so that the height of the first visual display device 204 is selectively adjustable by a user. Similar to that described above in conjunction with the first exemplary embodiment, the height of the cart 210 may be adjusted prior to each test session such that the center of the first visual display device 204, which contains the one or more visual objects 10, is generally horizontally aligned with the eyes of the seated subject 18 (i.e., so the subject 18 is looking straight at the visual object 10 on the visual display device 204 during the testing).

As shown in FIG. 2, the computing device 202 includes a plurality of user input devices 206, 208 connected thereto. Preferably, the user input devices 206, 208 comprise a keyboard 206 and a mouse 208. The first visual display device 204 may also serve as a user input device if it is provided with touch screen capabilities. In addition, a wireless user input device may also be operatively coupled to the computing device 202. The wireless user input device may be in the form of a wireless mouse 24, such as that described above in conjunction with the first illustrative embodiment.

Unlike the first exemplary embodiment of the vision testing system 100, the second exemplary embodiment of the vision testing system 200 further includes a force measurement assembly 212 for measuring the ground reaction forces and/or moments of the subject 18. In particular, the force measurement assembly 212 comprises a dual force plate 214 that is fixedly mounted to a rotatable carriage 218, which in turn is mounted to a translatable sled 222. The dual force plate 214 comprises a plurality of force transducers or load cells for measuring the forces and/or moments generated on the two plate surfaces thereof by respective feet of the subject 18. As such, the center of pressure (COP), center of gravity (COG), and/or sway angle of the subject 18 may be determined while the subject undergoes testing on the force measurement assembly 212. The rotatable carriage 218 with the dual force plate 214 mounted thereto rotates about a transverse rotational axis that generally passes through the ankles of the subject 18 when the subject 18 is disposed on the dual force plate 214. Thus, the transverse rotational axis about which the rotatable carriage 218 rotates is disposed above the surface of the dual force plate 214. The rotatable carriage 218 rotates within, and relative to the translatable sled 222. As such, when the translatable sled 222 is translated backwards-and-forwards relative to the stationary base portion 216, the rotatable carriage 218 and the dual force plate 214 are translated as well. Because the dual force plate 214 of the force measurement assembly 212 is capable of being displaced (i.e., rotated and translated), the force measurement assembly 212 is in the form of a dynamic force measurement assembly that is capable of displacing the subject 18 while he or she stands in a generally stationary position on the top surface of the dual force plate 214. The force measurement assembly 212 is described in detail in U.S. Pat. Nos. 8,704,855 and 8,847,989, the entire disclosures of which are incorporated herein by reference.

In one or more embodiments, the results of the tests performed on the force measurement assembly 212 may be combined with the results of the vision tests performed using the vision testing system 200 to arrive at a combined or composite balance score for the subject 18 (e.g., by using the data processing device 202 to perform the computations). In addition, in some embodiments, the motion sensing device 28 of the vision testing systems 100, 200 may be used to measure the head movement of the subject 18 while he or she undergoes balance testing on the force measurement assembly 212. For example, the head movement of the subject 18 may be determined using the motion sensing device 28 during the performance of a balance assessment protocol, such as the Sensory Organization Test ("SOT").

Referring again to FIG. 2, it can be seen that force measurement assembly 212 is provided with a second visual display device 220 thereabove. As shown in FIG. 2, the second visual display device 220 is generally hemispherical in shape such that it is capable of circumscribing at least three sides of the torso of the subject 18. Specifically, the subject 18 stands in the cutout 222 at the bottom of the second visual display device 220 so that he is able to become completely immersed in a virtual reality scenario that is displayed on the hemispherical projection screen of the second visual display device 220. Also, in one or more other embodiments, the vision testing of the subject 18 may be alternatively performed on the hemispherical visual display device 220, rather than on the generally planar visual display device 204. For example, the chair 20 on which the subject 18 is seated may be moved to a location in front of the second visual display device 220.

Figure 3:
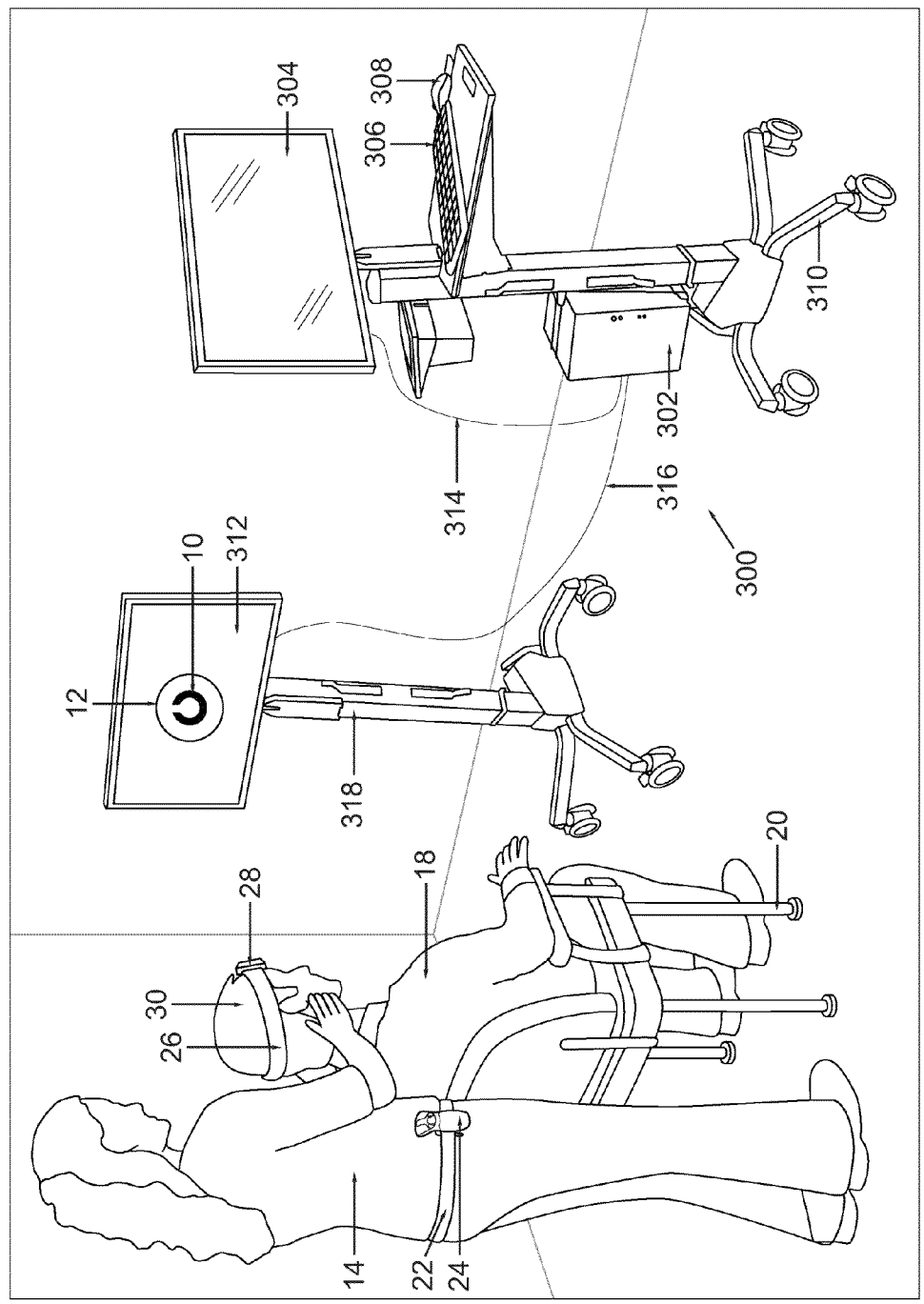
FIG. 3 is a diagrammatic perspective view of a third exemplary vision testing system that utilizes a computing device and first visual display device disposed on a first movable cart and a second visual display disposed on a second movable cart, according to yet another embodiment of the invention.

A third exemplary embodiment of a vision testing system is seen generally at 300 in FIG. 3. Referring to this figure, it can be seen that, in some respects, the third exemplary embodiment is similar to that of the first and second embodiments. Moreover, some elements are common to all of these embodiments. For the sake of brevity, the parts that the third embodiment of the vision testing system has in common with the first and second embodiments will only be briefly mentioned, if at all, because these components have already been explained in detail above. Furthermore, in the interest of clarity, these components will be denoted using the same reference characters that were used in the first two embodiments.

In the illustrative embodiment of FIG. 3, the vision testing system 300 generally comprises a computing device 302 (i.e., a data processing device or a data acquisition and processing device that is capable of collecting, storing, and processing data), which in turn, is operatively coupled to a first visual display device 304 by an electrical cable or wire 314, and to a second visual display device 312 by an electrical cable or wire 316. As shown in FIG. 3, the computing device 302 includes a plurality of user input devices 306, 308 connected thereto. Preferably, the user input devices 306, 308 comprise a keyboard 306 and a mouse 308. The first visual display device 304 may also serve as a user input device if it is provided with touch screen capabilities. In addition, a wireless user input device may also be operatively coupled to the computing device 302. The wireless user input device may be in the form of a wireless mouse 24, such as that described above in conjunction with the first illustrative embodiment.

In FIG. 3, the second visual display device 312 is disposed on an adjustable height cart 318 so that the height of the second visual display device 312 is selectively adjustable by a user. Similar to that described above in conjunction with the preceding two exemplary embodiments, the height of the cart 318 may be adjusted prior to each test session such that the center of the second visual display device 312, which contains the one or more visual objects 10, is generally horizontally aligned with the eyes of the seated subject 18 (i.e., so the subject 18 is looking straight at the visual object 10 on the visual display device 312 during the testing). Also, cart 310, on which the computing device 302, the first visual display device 304, and the user input devices 306, 308 are mounted, may also be provided height adjustment capabilities.

Figure 4:
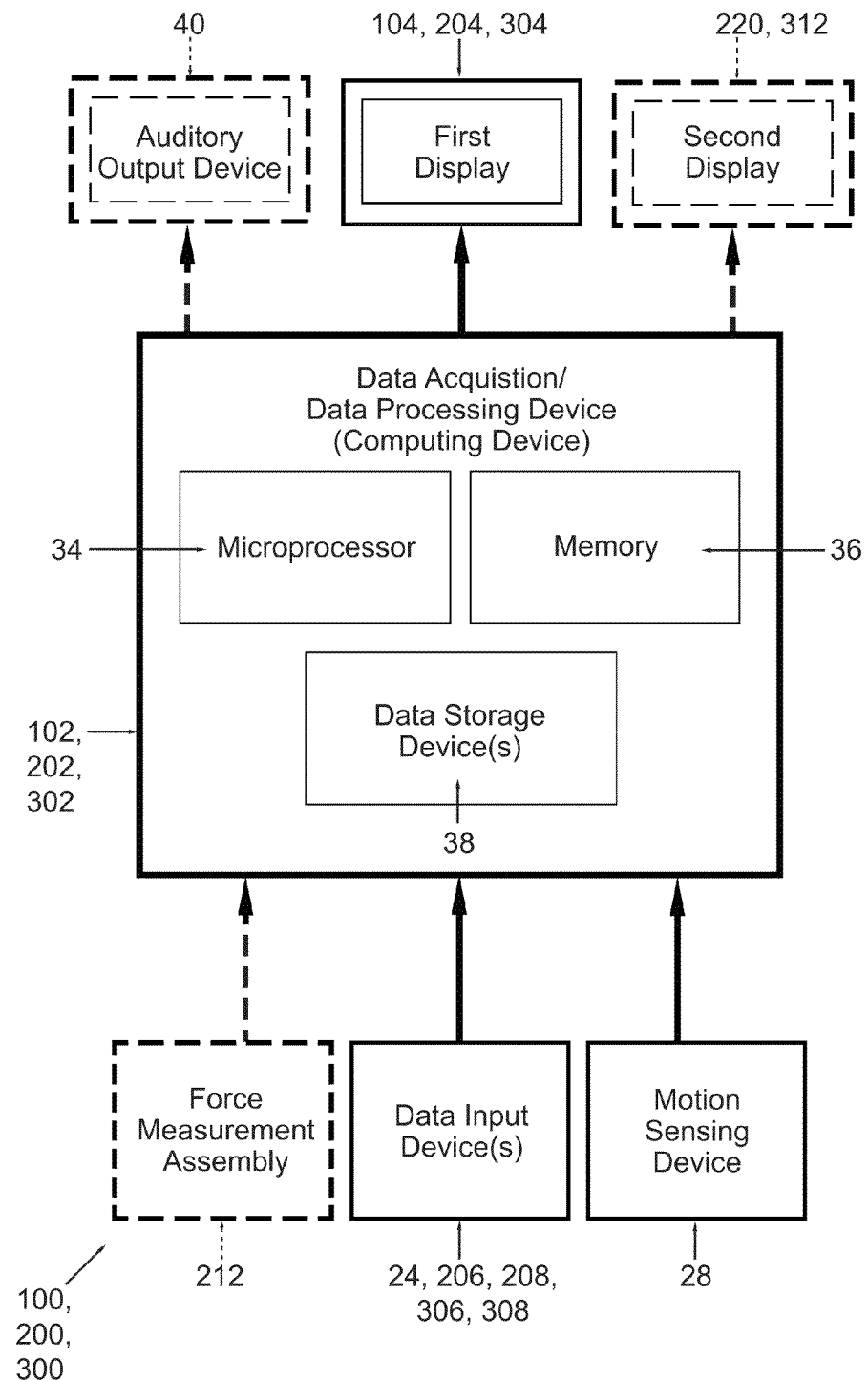
FIG. 4 is a block diagram of constituent components that may be utilized in the embodiments of the vision testing system described herein.

Now, turning to FIG. 4, it can be seen that the data acquisition/data processing devices (i.e., the computing devices 102, 202, 302) of the vision testing systems 100, 200, 300 each comprise a microprocessor 34 for processing data, memory 36 (e.g., random access memory or RAM) for storing data during the processing thereof, and data storage device(s) 38, such as one or more hard drives, compact disk drives, floppy disk drives, flash drives, or any combination thereof. As shown in FIG. 4, the motion sensing device 28 and the first visual display device 104, 204, 304 are operatively coupled to the computing devices 102, 202, 302 such that data is capable of being transferred between these devices. Also, as illustrated in FIG. 4, a plurality of data input devices 24, 206, 208, 306, 308, such as the wireless mouse 24, keyboards 206, 306, and mouse devices 208, 308, are operatively coupled to the computing devices 102, 202, 302 so that a user is able to enter data into the computing devices 102, 202, 302. In some embodiments, computing devices may be in the form of a desktop computer (as illustrated in FIGS. 2 and 3), while in other embodiments, the computing devices may be embodied as a laptop computer (as shown in FIG. 1).

Referring again to FIG. 4, it can be seen that some embodiments of the vision testing system may also include a second visual display 220, 312 that is operatively coupled to the computing device 202, 302 of the system (e.g., refer to FIGS. 2 and 3). Also, as illustrated in FIG. 2, some of the vision testing systems may further include a force measurement assembly 212 operatively coupled to the computing device 202, 302 of the system. While a dynamic-type force measurement assembly 212 is shown in FIG. 2, it is to be understood that static-type force measurement assemblies (e.g., static force plates) may also be operatively coupled to the computing device of the vision testing systems as well. In addition, with reference again to FIG. 4, it can be seen that an auditory output device 40 may also be operatively coupled to the computing device 102, 202, 302 of the vision testing systems 100, 200, 300. The auditory output device 40 may comprise one or more speakers or an audio headset that is configured to be worn by the subject 18. During the latter portion of the vision testing wherein the subject 18 displaces his or her head, the computing device 102, 202, 302 may be specially programmed to generate and output a first audible indicator (e.g., a first series of beeps) via the auditory output device 40 that indicates whether or not the velocity or speed at which the subject 18 is displacing his or her head lies within a predetermined range. Also, during the latter portion of the vision testing wherein the subject 18 displaces his or her head, the computing device 102, 202, 302 may be specially programmed to generate and output a second audible indicator (e.g., a second series of beeps) via the auditory output device 40 that indicates whether or not the subject 18 is displacing his or her head over a prescribed range of motion.

As an alternative to, or in addition to, generating instructional cues for the subject 18 using the auditory output device 40, the computing device 102, 202, 302 may be specially programmed to generate and display a first visual indicator (e.g., a change in the color of a selected area) on the output screen of the visual display device 104, 204, 312 that indicates whether or not the velocity or speed at which the subject 18 is displacing his or her head lies within the predetermined range. Also, as an alternative to, or in addition to, generating instructional cues for the subject 18 using the auditory output device 40, the computing device 102, 202, 302 may be specially programmed to generate and display a second visual indicator (e.g., a displaceable dot indicator) on the output screen of the visual display device that indicates whether or not the subject 18 is displacing his or her head over a prescribed range of motion.

Figure 7:
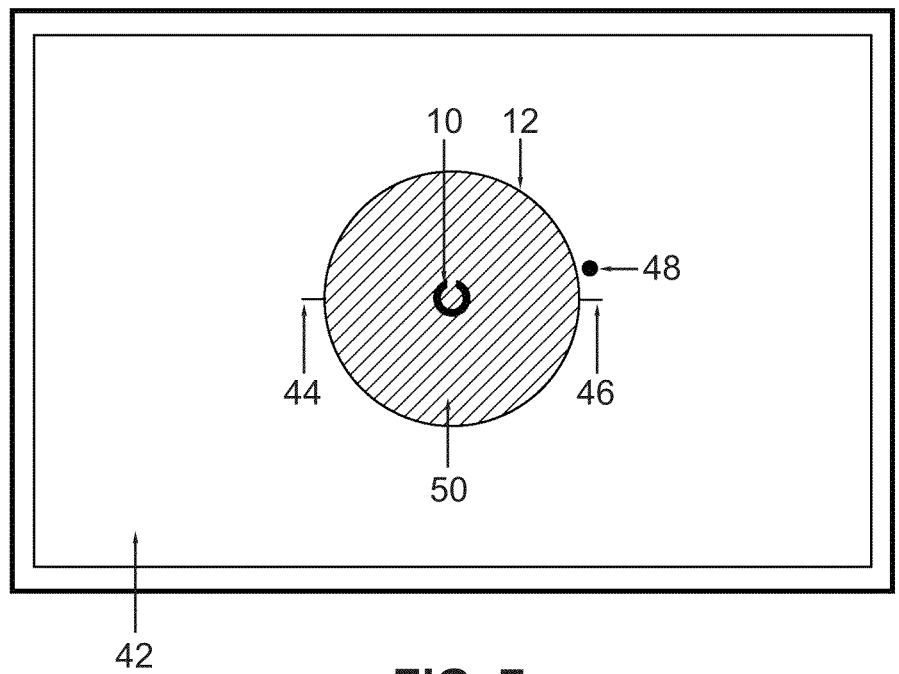
FIG. 7 is a screen image of the visual display device with first exemplary types of visual indicators that may be utilized in the embodiments of the vision testing system described herein.

Several examples of visual indicators that may be used in conjunction with the embodiments of the vision testing system are illustrated in FIGS. 7-9 and 21-24. First, turning to the first screen image 42 in FIG. 7, it can be seen that an optotype 10 in the form of a Landolt C may be provided within a circle 12 in the approximate center of the screen. The interior of the circle 12 may be provided with a first visual indicator 50 for indicating whether or not the velocity or speed at which the subject 18 is displacing his or her head lies within the predetermined range. For example, in one embodiment, the predetermined range for the velocity or speed of the subject's head may be between about 60 degrees per second and about 180 degrees per second (or between 60 degrees per second and 180 degrees per second). As another example, in a further embodiment, the predetermined range for the velocity or speed of the subject's head may be between about 85 degrees per second and about 120 degrees per second (or between 85 degrees per second and 120 degrees per second). In the illustrative embodiment of FIG. 7, the first visual indicator 50 comprises a change in a color of the area circumscribed by the circle 12. More particularly, the change in the color of the area circumscribed by the circle 12 comprises changing the circular region of the screen image 42 from a first color to a second color depending on whether or not the subject 18 is moving his or her head within the predetermined range. In FIG. 7, because this is a black-and-white image, the change in the color of the circular visual indicator 50 is indicated through the use of a hatching pattern (i.e., a diagonal hatching pattern). In one exemplary embodiment, the first color of the circular visual indicator 50 is red (e.g., bright red) when the velocity or speed of the subject's head lies outside of the predetermined range, while the second color of the circular visual indicator 50 is green when the velocity or speed of the subject's head lies within the predetermined range.

Referring again to FIG. 7, the second visual indicator 48 for indicating whether or not the subject is displacing his or her head over a prescribed range of motion will be explained. As shown in the illustrative example of FIG. 7, the second visual indicator 48 generally comprises a dot-like indicator that is displaced between first and second range of motion boundary lines 44, 46. As shown in FIG. 7, the first boundary line 44 extends from the left side of the circle 12, while the second boundary line 46 extends from the right side of the circle 12.

Also, it can be seen that the first and second boundary lines 44, 46 are spaced approximately 180 degrees apart in FIG. 7. The dot-like visual indicator 48 is displaced in accordance with the movement of the head 30 of the subject 18, as detected by the motion sensing device 28. For example, in one embodiment, the first boundary line 44 indicates a 20 degree rotation of the subject's head 30 to the left, while the second boundary line 46 indicates a 20 degree rotation of the subject's head 30 to the right. That is, if the subject 18 displaces his or her head 30 less than 20 degrees to the left, then the dot-like visual indicator 48 would not reach the first boundary line 44. Similarly, if the subject 18 displaces his or her head 30 less than 20 degrees to the right, then the dot-like visual indicator 48 would not reach the second boundary line 46. If the subject's head 30 is facing straight ahead (i.e., not displaced to either the right or left), then dot-like visual indicator 48 is located at the top of the circle 12 (i.e., approximately 90 degrees from the first boundary line 44 and approximately 90 degrees from the second boundary line 46). Advantageously, the second visual indicator 48 provides visual feedback to the subject 18 and the clinician 14 in order to inform the subject 18 and the clinician 14 as to whether or not the subject 18 is sufficiently displacing his or her head 30.

Figure 8A:
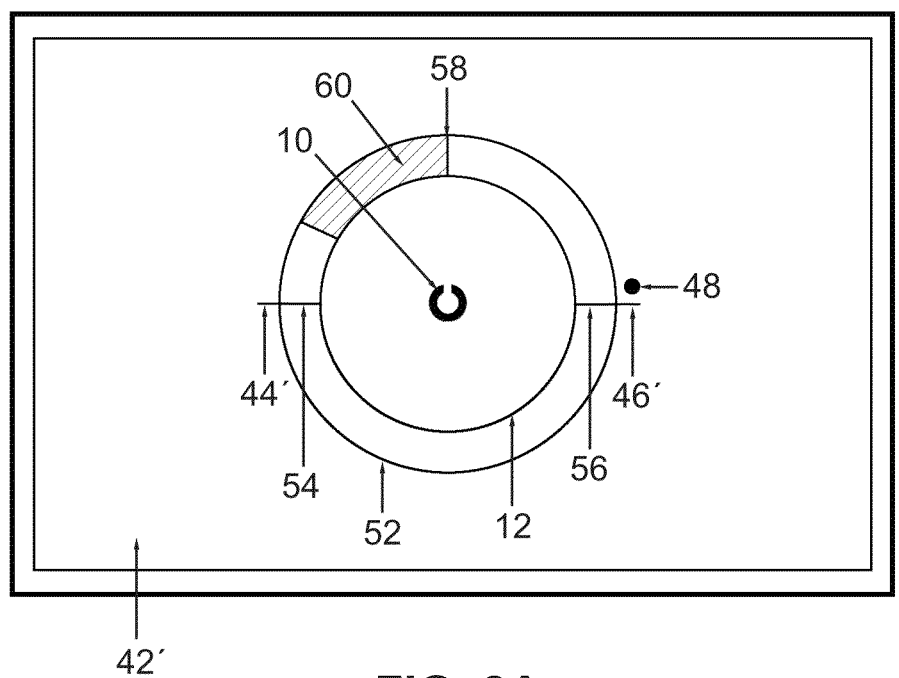
FIG. 8A is a screen image of the visual display device with second exemplary types of visual indicators that may be utilized in the embodiments of the vision testing system described herein, wherein the displacement of the subject's head to the left is shown.
Figure 8B:
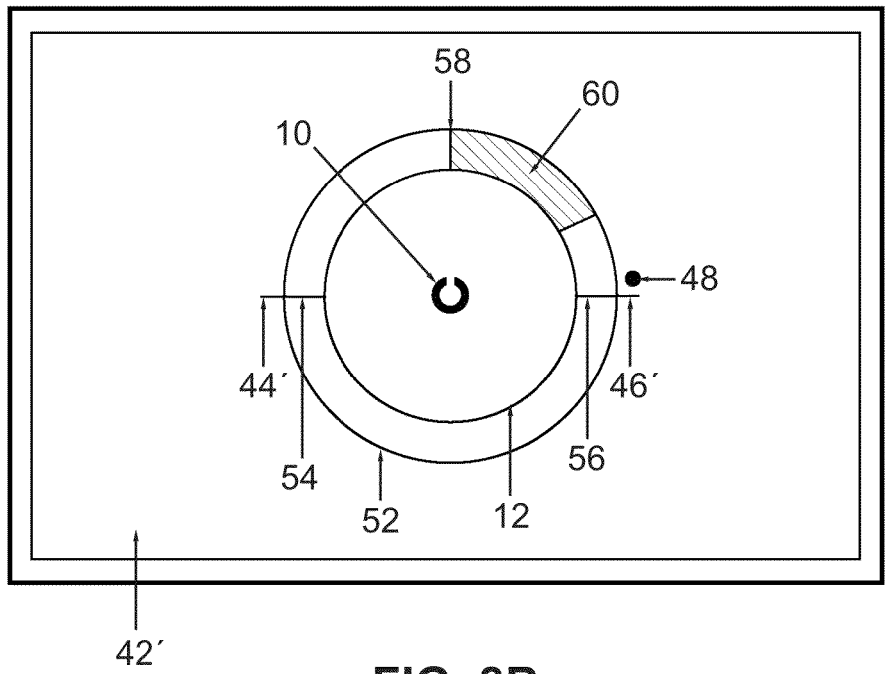
FIG. 8B is another screen image of the visual display device with the second exemplary types of visual indicators illustrated thereon, wherein the displacement of the subject's head to the right is shown.

Next, with reference to the second screen images 42' in FIGS. 8A and 8B, another exemplary type of first visual indicator will be described. Like the screen image 42 of FIG. 7, the screen images 42' comprise an optotype 10 in the form of a Landolt C within a circle 12 in the approximate center of the screen. However, unlike the screen image 42 of FIG. 7, the circle 12 surrounding the optotype 10 in FIGS. 8A and 8B is circumscribed by an outer circle 52, thereby defining an annular space between the inner and outer circles 12, 52. As shown in FIGS. 8A and 8B, the annular space between the inner and outer circles 12, 52 is divided into an upper half and a lower half by first and second boundary lines 54, 56. The upper half of the annular space between the inner and outer circles 12, 52 is further divided into a right and left section by top dividing line 58. The right and left sections of the annular upper half between the inner and outer circles 12, 52 are provided with a sliding bar visual indicator 60 in order to indicate whether or not the velocity or speed at which the subject 18 is displacing his or her head lies within the predetermined range. For example, referring first to FIG. 8A, the displacement of the sliding bar visual indicator 60 is controlled by the velocity or speed of the subject's head 30. That is, if the subject 18 is displacing his or her head 30 at a slow speed, the sliding bar visual indicator 60 will only travel a small distance from the center dividing line 58. In contrast, if the subject 18 is displacing his or her head 30 at a high speed, the sliding bar visual indicator 60 will travel a large distance from the center dividing line 58. Also, because the sliding bar visual indicator 60 is located in the left section of the top annular portion in FIG. 8A, it indicates that the subject's head 30 is being displaced to the left, as detected by the motion sensing device 28. In contrast, when the sliding bar visual indicator 60 is located in the right section of the top annular portion as in FIG. 8B, it indicates that the subject's head 30 is being displaced to the right, rather than the left. In addition, if the subject 18 displaces his or her head 30 at a velocity that is higher than the predetermined range, the sliding bar visual indicator 60 is changed from a first color to a second color to indicate a saturation of the head velocity or speed. In FIG. 8A, because this is a black-and-white image, the change in the color of the sliding bar visual indicator 60 is indicated through the use of a hatching pattern (i.e., a diagonal hatching pattern). In one exemplary embodiment, the first color of the sliding bar visual indicator 60 is red (e.g., bright red) when the velocity or speed of the subject's head exceeds the predetermined range (i.e., when it is saturated), while the second color of the sliding bar visual indicator 60 is green when the velocity or speed of the subject's head lies within the predetermined range (i.e., it is not saturated).

The second visual indicator 48 in FIGS. 8A and 8B, which indicates whether or not the subject is displacing his or her head over a prescribed range of motion, is very similar to that described above in conjunction with FIG. 7. Like the second visual indicator 48 of FIG. 7, the second visual indicator 48 of FIGS. 8A and 8B is also in the form of a dot-like visual indicator. In addition, the first and second boundary lines 44', 46' are generally the same as the first and second boundary lines 44, 46 of FIG. 7, except that each boundary line 44', 46' extends outwardly from the opposed sides of the outer circle 52 in FIGS. 8A and 8B, rather than from the opposed sides of the inner circle 12.

Figure 9:
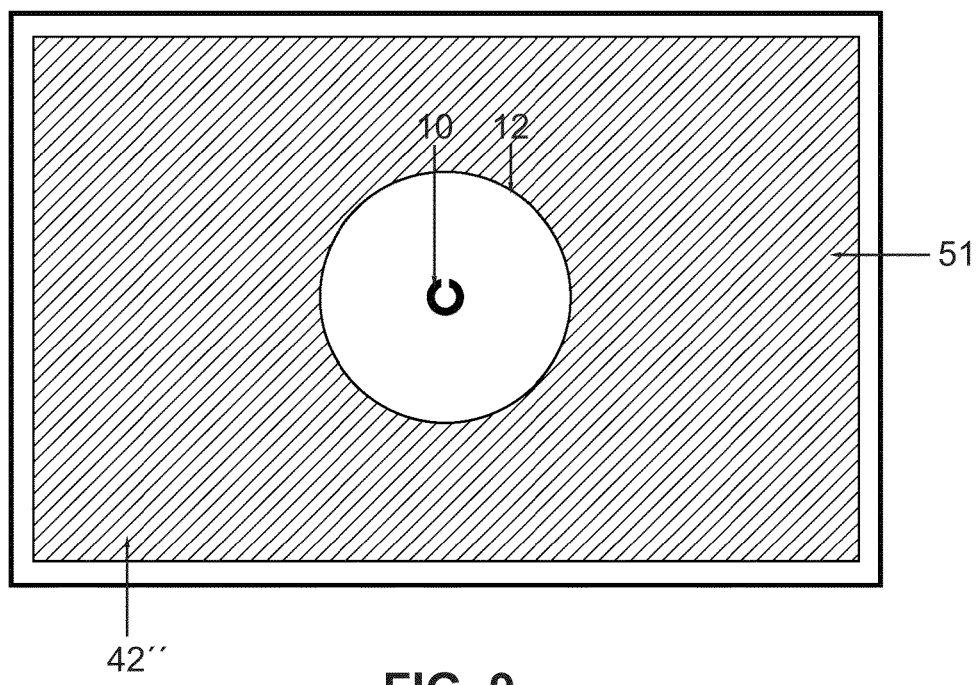
FIG. 9 is a screen image of the visual display device with a third exemplary type of visual indicator that may be utilized in the embodiments of the vision testing system described herein.

Now, referring to third screen image 42" in FIG. 9, yet another exemplary type of first visual indicator will be described. Like the screen images 42, 42' of FIGS. 7 and 8A-8B, the screen image 42" comprises an optotype 10 in the form of a Landolt C within a circle 12 in the approximate center of the screen. However, unlike the screen image 42 of FIG. 7, the circular region within the circle 12 is not provided with changing colors. Rather, the circular region within the circle 12 has a consistent white background (i.e., it does not change during the test), while the color of the background region 51 outside of the circle 12 changes depending upon the sensed velocity or speed of the subject's head 30. More particularly, the change in the color of the background region 51 outside of the circle 12 comprises changing the background region 51 of the screen image 42" from a first color to a second color depending on whether or not the subject 18 is moving his or her head within the predetermined range. In FIG. 9, because this is a black-and-white image, the change in the color of the background region 51 outside of the circle 12 is indicated through the use of a hatching pattern (i.e., a diagonal hatching pattern). In one exemplary embodiment, the first color of the background region 51 is red (e.g., bright red) when the velocity or speed of the subject's head lies outside of the predetermined range, while the second color of the background visual indicator 51 is green when the velocity or speed of the subject's head lies within the predetermined range.

Unlike the screen images 42, 42' of FIGS. 7 and 8A-8B, it can be seen that the screen image 42" does not include a second visual indicator 48 for indicating whether or not the subject 18 is displacing his or her head over a prescribed range of motion. Rather, the screen image 42" only includes the first visual indicator 51 for indicating whether or not the subject 18 is moving his or her head within the predetermined velocity range. Other exemplary visual indicators for indicating whether the subject displaces his or her head within the prescribed velocity range will be described hereinafter in conjunction with the description of the dynamic visual acuity testing procedure.

2. Dynamic Visual Acuity Testing Procedure

Figure 11A:
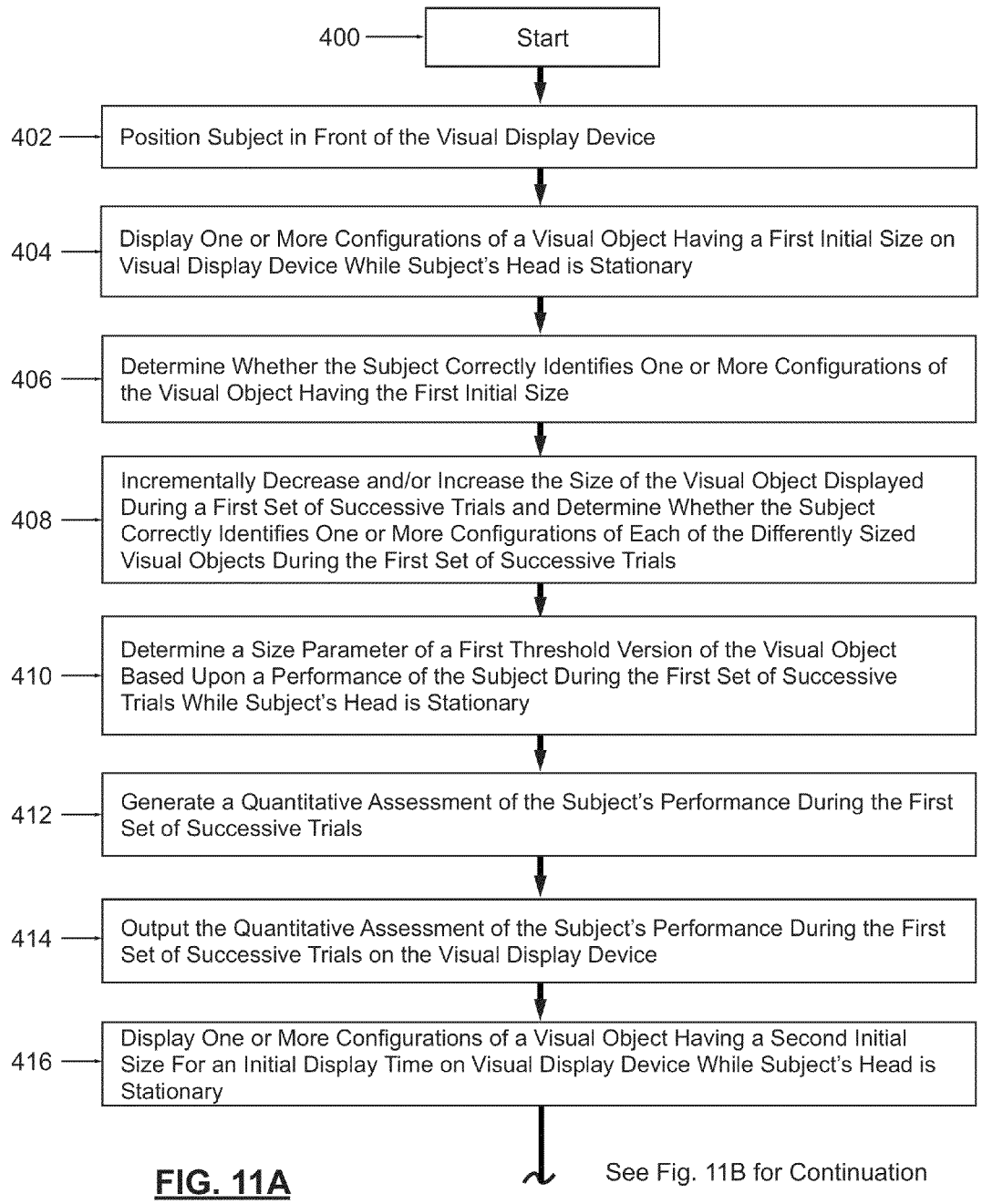
FIG. 11A is a partial flowchart illustrating a procedure for testing the dynamic visual acuity of a subject carried out by the systems illustrated in FIGS. 1-3, according to an embodiment of the invention.
Figure 11B:
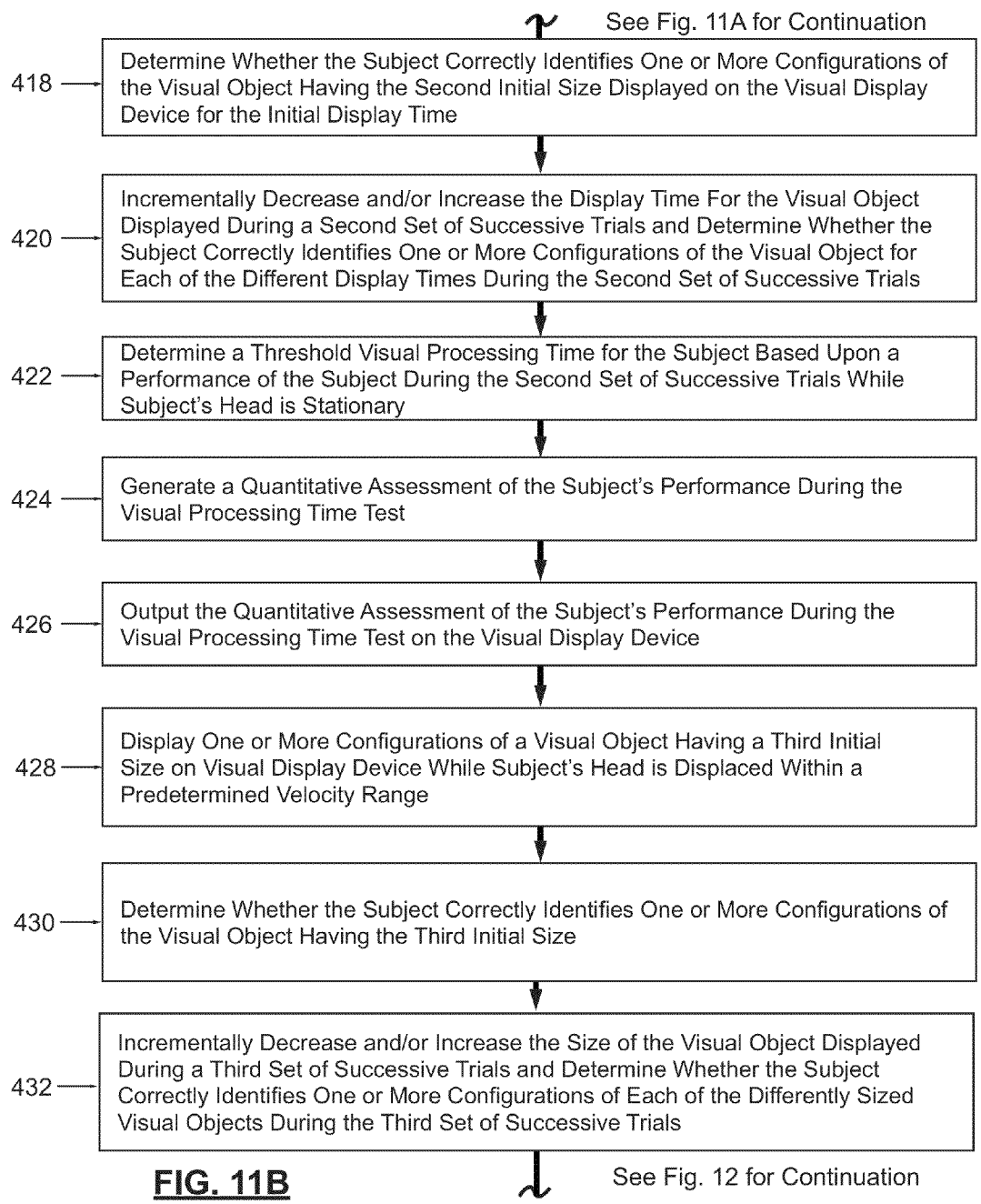
FIG. 11B is a continuation of the flowchart of FIG. 11A, which illustrates additional steps of the procedure for testing the dynamic visual acuity of a subject, according to an embodiment of the invention.
Figure 12:
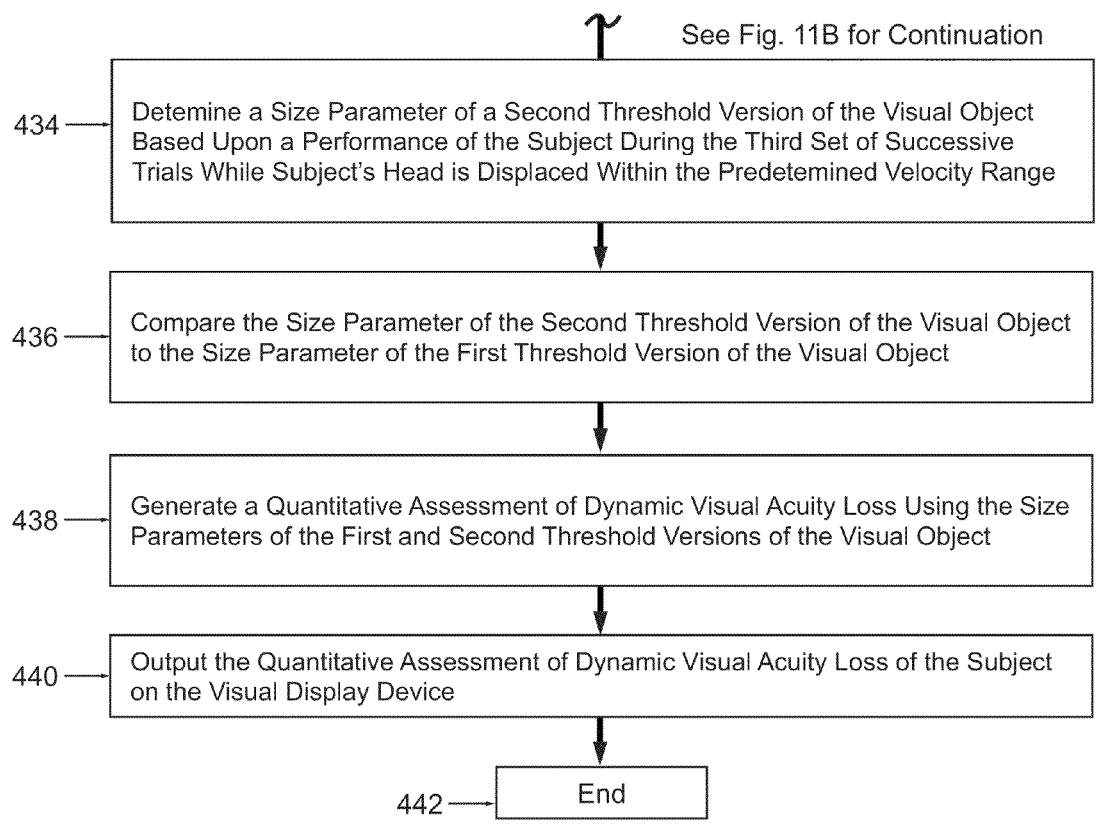
FIG. 12 is a continuation of the flowchart of FIG. 11B, which illustrates yet additional steps of the procedure for testing the dynamic visual acuity of a subject, according to an embodiment of the invention.

In accordance with an embodiment of the invention, a flowchart illustrating a procedure for testing the dynamic visual acuity of a subject carried out by the systems is set forth in FIGS. 11A, 11B, and 12. Referring initially to FIG. 11A, the procedure commences at 400 (e.g., after the operator or clinician enters a start command to the computing device 102, 202, 302 by depressing a particular key on the keyboard), and in step 402, the subject is positioned in front of the output screen of the visual display device 104, 204, 304 such that a visual object 10 (e.g., an optotype) is visible to the subject 18. Then, while the subject 18 maintains a generally fixed position of his or her head 30 (i.e., keeping his or her head 30 as still as possible), one or more configurations of the visual object 10 having a first initial size are displayed on the output screen of the visual display device 104, 204, 304 in step 404. For example, referring to FIG. 5, one or more configurations 10*e*, 10*f*, 10*g*, 10*h* of the Landolt C optotype may be displayed one-at-time on the output screen of the visual display device 104, 204, 304. In an alternative exemplary embodiment, with reference to FIG. 6, one or more configurations 10'*e*, 10'*f*, 10'*g*, 10'*h* of the Tumbling E optotype may be displayed one-at-time on the output screen of the visual display device 104, 204, 304. In other exemplary embodiments, other suitable optotypes may be used in place of the Landolt C or the Tumbling E, such as letters of a recognized alphabet (e.g., the English alphabet). In one or more embodiments, the visual object (i.e., optotype) having the first initial size is displayed within approximately 500 milliseconds after the operator or clinician enters the start command to the computing device 102, 202, 302. The visual object (i.e., optotype) having the first initial size may be sufficiently large so that nearly all of the subjects tested will correctly identify the configuration of the first optotype that is displayed on the screen, and may be displayed for a time duration of approximately 500 milliseconds on the screen. After the visual object (i.e., optotype) disappears from the output screen of the visual display device 104, 204, 304, the computing device 102, 202, 302 may be specially programmed to implement a wait state, wherein the computing device 102, 202, 302 waits for the operator or clinician to record the subject's response.

Figure 15:
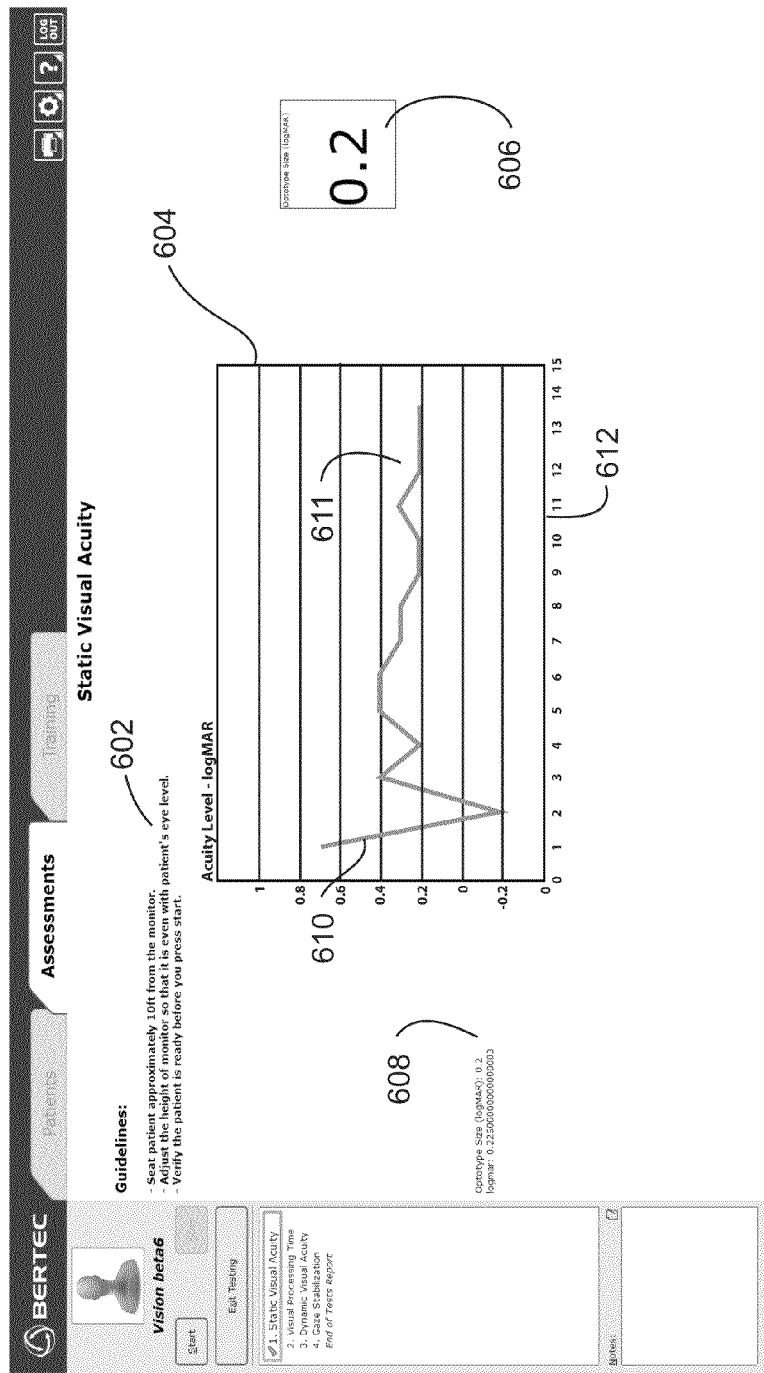
FIG. 15 is a first exemplary operator screen image of the visual display device, which may be displayed during the performance of a static visual acuity test, according to an embodiment of the invention.

An exemplary operator or clinician screen image 600, which may be displayed on the visual display device 104, 204, 304 during the first set of successive trials when the subject 18 maintains the generally fixed position of his or her head 30, is shown in FIG. 15. In one or more embodiments, the computing device 102, 202, 302 may be specially programmed to generate the screen image 600 of FIG. 15 during the performance of this first portion of the test. With reference to FIG. 15, it can be seen that testing guidelines 602 may be displayed at the top of the screen image 600. The testing guidelines may specify a suggested distance or distance range (e.g., approximately ten (10) feet or between eight (8) and sixteen (16) feet) for the placement of the subject 18), visual display device height adjustment instructions, and additional instructions regarding the readiness of the subject. In one or more embodiments, the computing device 102, 202, 302 may be specially programmed to prompt the operator or clinician to input the distance between the forehead of the subject and the front of the visual display device screen (e.g., in feet from the front of the screen). The default test setting for the distance may be ten (10) feet, while the computing device 102, 202, 302 may be specially programmed to accept a range of distances between eight (8) and sixteen (16) feet, inclusive. The computing device 102, 202, 302 also may be specially programmed to generate a checkbox on the output screen of the visual display device screen that may be checked when the subject 18 wears progressive lenses (e.g., glasses or contact lens for vision correction). As additionally shown in FIG. 15, a graph 604 is also displayed in the center of the screen in order to visually illustrate the optotype size for each successive trial while the subject's head 30 remains stationary. That way, the operator or clinician is able to easily view the subject's performance during the progression of the testing. As shown in FIG. 15, the y-axis 610 of the graph 604 is the optotype size (e.g., in log MAR or relative log MAR), while the x-axis 612 of the graph 604 is the trial number of the first set of successive trials (i.e., while the head 30 of the subject 18 remains stationary). In the graph 604 of FIG. 15, it can be seen that, after the highly variable beginning of the test, the stimulus level curve 611 tends to oscillate above and below an optotype size of approximately 0.20. Referring again to FIG. 15, it can be seen that the small box 606 on the right center of the clinician screen image 600 is configured to display the optotype size (e.g., in log MAR or relative log MAR) during the current trial of the testing procedure. Advantageously, the display of the optotype size in the small box 606 allows the clinician to quickly ascertain the subject's current performance level during the execution of the test. In the screen image 600 of FIG. 15, selected test summary data 608 is displayed below, and to the left of the graph 604 on the screen. For example, as shown in FIG. 15, the test summary data 608 may include the optotype size in units of log MAR. In one or more embodiments, some values of the test summary data may be automatically completed as each of the test portions is successively completed (e.g., static visual acuity, visual processing time, dynamic visual acuity, and gaze stabilization).

Figure 16:
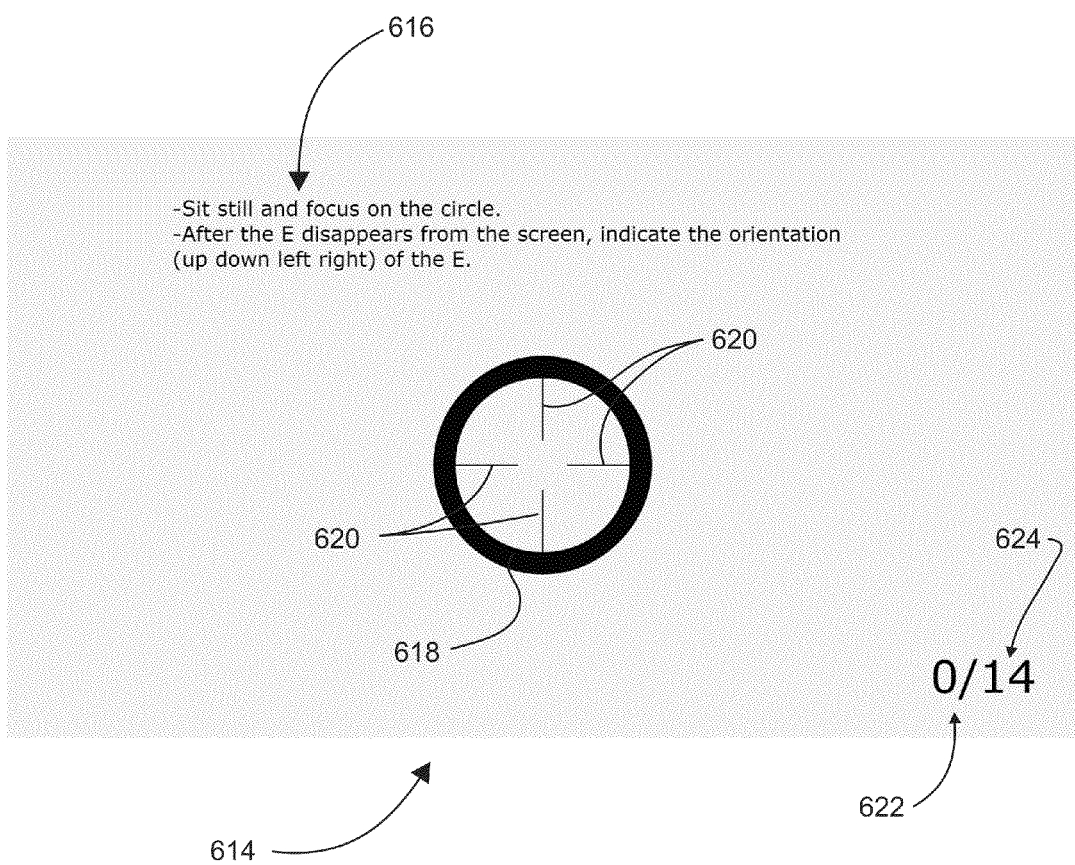
FIG. 16 is a subject screen image of the visual display device with a fourth exemplary type of visual indicator that may be utilized during the performance of the static visual acuity test, according to an embodiment of the invention.
Figure 17:
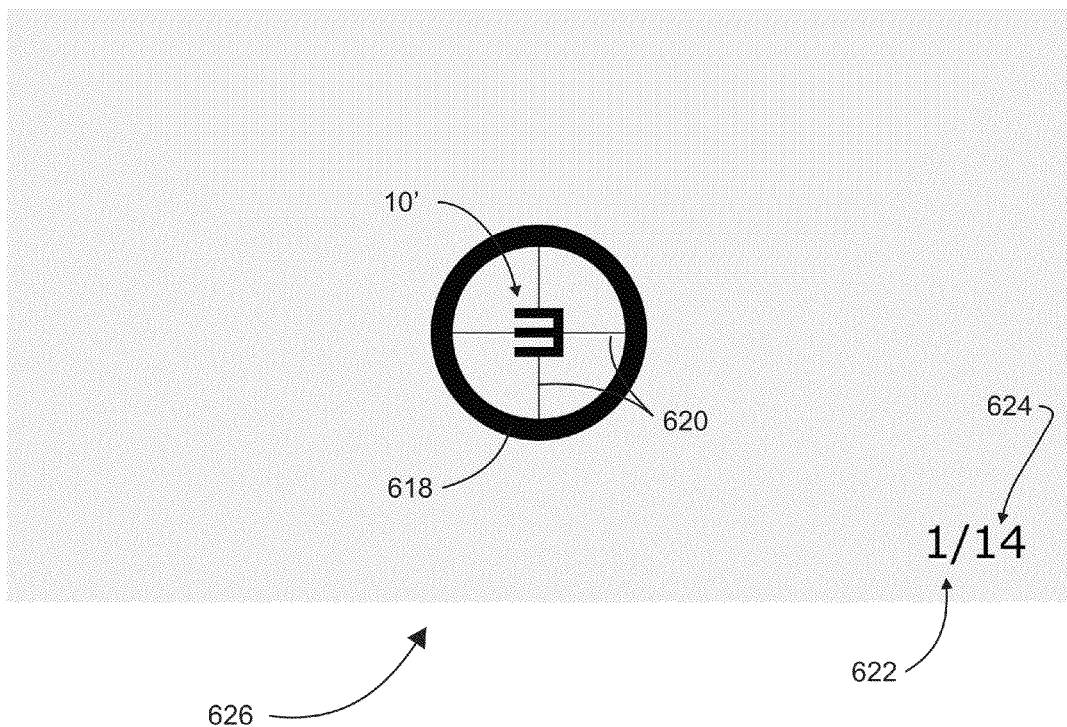
FIG. 17 is a subject test screen image of the visual display device prior to the performance a static visual acuity test or a visual processing time test, wherein the fourth exemplary type of visual indicator is displayed together with the second exemplary type of optotype, according to an embodiment of the invention.

With reference to FIGS. 16 and 17, exemplary subject screen images 614, 626, which may be displayed on the visual display device 104, 204, 304 during the first set of successive trials when the subject 18 maintains the generally fixed position of his or her head 30, will now be explained. Initially, referring to FIG. 16, it can be seen that a set of instructions 616 for the subject or patient may be displayed at the top of the screen image 614. The subject or patient instructions may specify that the manner in which the subject or patient is supposed to carry out the test (e.g., by instructing the patient to sit still and focus on the circle 618, and by instructing the patient to indicate the orientation of the optotype after it disappears from the screen). The set of instructions 616 may be initially displayed on the output screen by the computing device 102, 202, 302, and then subsequently hid from view (i.e., suppressed thereafter) so as not to unnecessarily distract the subject 18 during the testing. As additionally shown in FIG. 16, a solid black circle 618 is displayed in the approximate center of the screen. The solid black circle 618 comprises a plurality of crosshairs 620 disposed therein (e.g., spaced 90 degrees apart from one another, and disposed at 0 degrees, 90 degrees, 180 degrees, and 360 degrees), and extending inwardly towards the center of the circle 618. Referring again to FIG. 16, it can be seen that, in the bottom right-hand corner of the screen, the number of trials 622 completed thus far, together the maximum number of trials 624 that may be completed during the first set of successive trials is displayed. Because FIG. 16 depicts the starting screen image 614 for the first set of successive trials (i.e., when the subject's head is stationary), the number 622 is zero (0) in FIG. 16. In this illustrative embodiment, the maximum number of trials 624 performed in conjunction with the first set of successive trials is fourteen (14). However, it is to be understood that, in other embodiments of the invention, the maximum number of trials 624 performed in conjunction with the first set of successive trials may be higher or lower than fourteen (14). Also, in an alternative embodiment, the small box 606 with the optotype size described above in conjunction with FIG. 15 and the small box 634 with the optotype display time described below in conjunction with FIG. 18 may be placed in the bottom right-hand corner of the screen 614, rather than the number of trials 622 completed thus far, and the maximum number of trials 624. In this alternative embodiment, the number of trials 622 completed thus far, and the maximum number of trials 624 are placed in the test summary data 608 on the operator or clinician screen 600. Turning to FIG. 17, it can be seen that the screen image 626 is generally the same as the screen image 614 of FIG. 16, except that an optotype 10' is displayed in the center of the circle 618.

While a Tumbling E optotype is utilized in the illustrative embodiment of FIG. 17, it is to be understood that, in an alternative embodiment, a Landolt C optotype or another type of optotype may be used in place of the Tumbling E optotype. In the exemplary screen image 626 of FIG. 17, it can be seen that the optotype is pointing to the left, so a correct identification of the optotype by the subject or patient would require that he or she indicates that the optotype is pointing to the left. In addition, as depicted in FIG. 17, the number of trials 622 is equal to one (1) in order to indicate that the subject or patient has completed one trial of the first set of successive trials (i.e., when the subject's head is stationary).

The circle 618 depicted in FIGS. 16 and 17, which is generated by the computing device 102, 202, 302, is large enough to fit the largest size optotype that will be displayed to the subject or patient during the static testing. The crosshairs 620 extend inward in order to prevent the circle 618 from needing to change size. Advantageously, in order to avoid becoming a distraction to the subject during the testing, the size of the circle 618 remains constant (i.e., it is static). Because the size of the circle 618 is constant during the testing, it must be large enough to accommodate the largest optotype that will be displayed to the subject during the testing. Consequently, this results in a circle 618 that is significantly larger than the smallest sized optotypes displayed during the testing, which in turn, makes it difficult for the subject to tell where the small sized optotypes will appear on the screen. The subject's ability to find the optotype on the screen is not something that it is desired to be factored into the testing. Thus, the crosshairs 620 are provided within the circle 618 in order to help direct the gaze of the subject or patient during the display of the optotype, especially that of a small optotype. Like the circle 618, the crosshairs 620 are static during the testing (i.e., they do not undergo changes in size or shape) so as not to distract the subject during the testing. Also, as best shown in FIG. 16, the crosshairs 620 do not extend all the way to the center of the circle 618 so as to prevent them from interfering with the display of the small optotypes. In addition, both the circle 618 and the crosshairs 620 remain on the output screen of the visual display device throughout the duration of the testing.

Now, turning again to FIG. 11A, in step 406, the computing device or data processing device 102, 202, 302 determines whether or not the subject 18 correctly identifies one or more configurations (e.g., 10'e, 10'f, 10'g, 10'h) of the visual object 10' having the first initial size. For example, the subject 18 may be presented with one or more optotypes having the first initial size (e.g. a single optotype 10'g pointing down). This optotype 10'g is of the first initial size, which may be a size scale factor of 0.75. After the optotype is displayed to the subject 18, the subject 18 or the clinician 14 may utilize a user input device 24 (e.g., a wireless mouse) in order to transmit the response of the subject 18 to the computing device 102, 202, 302 (e.g., the wireless mouse may have four buttons, each of which corresponds to one of the four configurations of the optotype). Alternatively, the response of the subject 18 may be entered using the keyboard of the computing device 102, 202, 302 by using the directional arrows and space bar on the keyboard. For example, the "up" arrow key on the keyboard is used to record an optotype pointing up, the "down" arrow key on the keyboard is used to record an optotype pointing down, the "left" arrow key on the keyboard is used to record an optotype pointing to the left, the "right" arrow key on the keyboard is used to record an optotype pointing to the right, and the spacebar is used to record an unknown orientation of the optotype. If the spacebar is depressed on the keyboard, the computing device 102, 202, 302 randomly chooses the response of the subject 18. After receiving the subject's response, the computing device 102, 202, 302 is specially programmed to determine if the subject correctly determined the configuration of the optotype that was displayed on the output screen of the visual display device 104, 204, 304. For example, if the optotype 10'g of FIG. 6 was displayed on the screen, the subject 18 must indicate that optotype is pointing down to get the identification correct. Any other answer would be incorrect for this configuration of the optotype. Once the subject's answer or response is evaluated as to its correctness, the computing device 102, 202, 302 is specially programmed to record whether or not the subject 18 identified the optotype correctly. In one exemplary embodiment, if the subject 18 identifies the configuration of the optotype 10'g correctly, the computing device 102, 202, 302 is specially programmed to display one or more optotypes having a physical size that is smaller than the first optotype (e.g., the second trial may comprise one or more optotypes that have a size scale factor of 0.6875). For example, the second optotype may comprise the optotype 10'j in FIG. 6, which has a smaller size than the optotype 10'g in the middle row of FIG. 6. Conversely, if the subject 18 identifies the configuration of the first optotype 10'g incorrectly, the computing device 102, 202, 302 is specially programmed to display one or more optotypes having a physical size that is larger than the first optotype (e.g., the second optotype may have a size scale factor of 1.0). For example, in this case, the second optotype may comprise the optotype 10'c in the top row of FIG. 6, which has a larger size than the optotype 10'g in the middle row of FIG. 6. In one or more embodiments, as described hereinafter, the computing device 102, 202, 302 is specially programed to execute a parameter estimation algorithm (e.g., Best-PEST algorithm) in order to determine the physical size of the successive optotype that is displayed on the output screen of the visual display device 104, 204, 304. Also, in one or more embodiments, the computing device 102, 202, 302 is specially programmed to display the successive optotype on the screen approximately five-hundred (500) seconds after it receives the subject's response regarding the preceding optotype.

In this manner, as specified in step 408 of FIG. 11A, the computing device 102, 202, 302 is specially programmed to incrementally decrease or increase the size of the visual object on the output screen of the visual display device 104, 204, 304 during a first set of successive trials (e.g., during a maximum number 624 of fourteen (14) trials as indicated in FIGS. 16 and 17). For example, if the subject identifies the configuration of a particular-sized optotype correctly, the optotype size of the next optotype displayed on the screen is generally decreased, while the optotype size of the next optotype displayed on the screen is generally increased if the subject fails to identify the configuration of the optotype correctly. In the exemplary embodiment, after each optotype is displayed on the output screen of the visual display device 104, 204, 304, the computing device 102, 202, 302 is specifically programmed to determine whether or not the subject 18 correctly identified the configuration of the optotype.

In one or more embodiments, the size of the visual object presented to the subject 18 during the first set of successive trials generally changes with each successive trial (e.g., the subject 18 does not receive five (5) optotypes of the same size in consecutive order during the testing). Similarly, the size of the visual object presented to the subject 18 during the dynamic DVA trials, as described hereinafter, generally changes with each successive trial (e.g., the subject 18 does not receive five (5) optotypes of the same size in consecutive order during the DVA testing). Also, during the dynamic series of trials during the GST, which will be described hereinafter, the target angular velocity range generally changes with each successive trial (e.g., the subject 18 does not perform five (5) optotype identifications for the same angular velocity range in consecutive order during the GST).

In step 410 of FIG. 11A, after the subject 18 has completed a predetermined number of trials of optotype identification, the computing device 102, 202, 302 is specifically programmed to determine a size parameter (e.g., a size scale factor) of a first threshold version of the optotype based upon the performance of the subject 18 during the first set of successive trials during which the subject 18 maintained the generally fixed position of his or her head 30. For example, after a particular end condition is reached, the computing device 102, 202, 302 determines that the first threshold version of the optotype has a size scale factor of 0.40. In one embodiment, the size scale factor of the first threshold version of the optotype is a calculated value that is determined using one or more statistical equations or formulas (e.g., using a Best-PEST algorithm as described hereinafter).

The computing device 102, 202, 302 may be specifically programmed with multiple end conditions for determining when to end the first set of successive trials. For example, the computing device 102, 202, 302 may automatically stop the first set of successive trials as soon as any one or combination of the following conditions occur: (i) the subject has completed a total of fourteen (14) trials of optotype identification (i.e., a maximum allowable number of trials is reached), (ii) a predetermined number of reversals has occurred, or (iii) the user has stopped the first set of successive trials (e.g., the operator or clinician initiates the cessation of the successive trials by depressing a particular key on the keyboard).

In one or more embodiments, the computing device 102, 202, 302 may be specially programmed to automatically stop the first set of successive trials when both the computed number of reversals for the test series has exceeded the predetermined number of reversals and the computed number of trials for the test series has exceeded the predetermined number of trials. Initially, the manner in which the total number of reversals is calculated by the computing device 102, 202, 302 will be explained. During the vision testing, a reversal is determined in accordance with the following equation:

$$\text{diff}=[y(i-1)-y(i)]*[y(i)-y(i+1)] \quad (5)$$

where:
diff: product of the slope before and after a stimulus point;
y(i): stimulus value at trial number i;
y(i−1): stimulus value for the trial preceding trial number i;
y(i+1): stimulus value for the trial following trial number i;
i: trial number for which the reversal is being determined.
After computing the difference value determined using equation (5) for a given trial number, if it is determined by the computing device 102, 202, 302 that the difference value is less than or equal to zero, then the reversal counter is incremented using the following equation:

$$\text{rev}=\text{rev}+1 \quad (6)$$

That is, the reversal number counter is incremented by one. Conversely, if it is determined by the computing device 102, 202, 302 that the difference value is greater than zero, then the reversal counter is not incremented and the number of reversals stays the same. Also, if the computed difference value is less than or equal to zero, and thus the reversal counter is incremented, the computing device 102, 202, 302 may be specially programmed to next determine if the total computed number of reversals is greater than or equal to the predetermined number of reversals that has been set (e.g., a total number of eight (8) reversals). After which, the computing device 102, 202, 302 may be specially programmed to further determine if the total number of trials that have been completed (value of i) is greater than or equal to a predetermined number of trials (e.g., fourteen (14) trials of optotype identification). When both the total computed number of reversals is greater than or equal to the predetermined number of reversals (e.g., eight (8) reversals), and the total number of trials that have been completed is greater than or equal to the predetermined number of trials (e.g., fourteen (14) trials), then the computing device 102, 202, 302 may be specially programmed to automatically stop the first set of successive trials of the vision testing. It is to be understood that the abovedescribed procedure may be used to determine the stopping point of the visual processing time, DVA, and GST series of successive trials as well.

Figure 26:
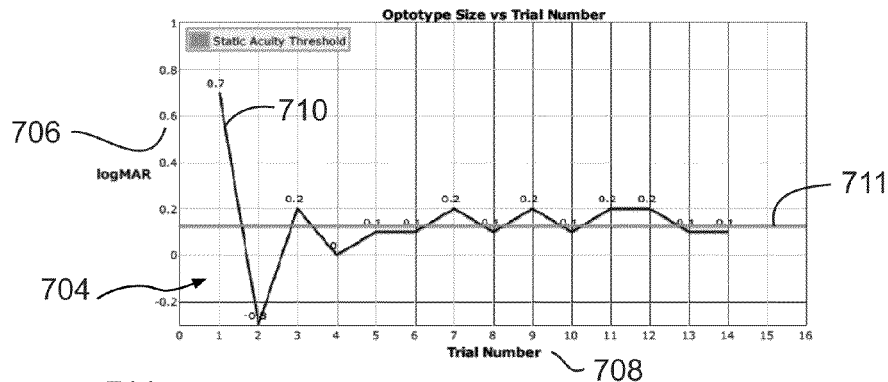
FIG. 26 is a fifth exemplary operator screen image of the visual display device, which illustrates an exemplary report generated by the vision testing system for displaying the results from a static visual acuity test, according to an embodiment of the invention.

For example, referring to the graph 704 in FIG. 26, the computing device 102, 202, 302 would determine that a total number of eleven (11) reversals have occurred during the testing series by using equation (5) above.

Then, in step 412 of FIG. 11A, the computing device 102, 202, 302 is specifically programmed to generate a quantitative assessment of the subject's performance during the first set of successive trials, and finally, in step 414 of FIG. 11A, to output the quantitative assessment of the subject's performance during the first set of successive trials on the output screen of the visual display device 104, 204, 304. For example, in an exemplary embodiment, the computing device 102, 202, 302 may generate a report 700, such as that illustrated in FIG. 26, in order to display the test results from the first set of successive trials.

With reference to FIG. 26, the content of an exemplary test report for the first static set of successive trials will be described. As shown in FIG. 26, it can be seen that selected test parameters 702 may be displayed at the top of the screen image 700. The test parameters 702 may include: (i) the direction of head rotation during dynamic portions of the DVA test (i.e., about the yaw axis 66 of FIG. 10), (ii) the approximate distance (e.g., in feet) between the subject and the visual display device 104, 204, 304, (iii) whether or not progressive or corrective lenses (i.e., glasses or contact lens) are worn by the subject, (iv) the optotype display time (e.g., as determined during the visual processing time test described hereinafter), and (v) the target head angular velocity range for the subject during dynamic portions of the DVA test (e.g., in degrees per second). As additionally shown in FIG. 26, a graph 704 is also displayed in the upper central portion of the screen in order to visually illustrate the optotype size (i.e., in log MAR or relative log MAR) for each successive trial while the subject's head 30 remains stationary. That way, the operator or clinician is able to easily observe any trends that occurred during the testing (i.e., consistent incorrect answers, consistent correct answers, etc.) and to easily assess whether or not the testing results follow a normal trend (e.g., transient response-type curve as explained hereinafter). As shown in FIG. 26, the y-axis 706 of the graph 704 is the optotype size (e.g., in log MAR or relative log MAR), while the x-axis 708 of the graph 704 is the trial number of the first set of successive trials (i.e., while the head 30 of the subject 18 remains stationary). In the graph 704 of FIG. 26, it can be seen that, after the highly variable beginning of the test, the stimulus level curve 710 tends to oscillate above and below an optotype size of approximately 0.15 (i.e., most of the local maximum and minimum points of the curve 710 occur at log MAR values of 0.2 and 0.1, respectively). A horizontal line 711 is drawn at an optotype size of 0.15 log MAR in the graph 704 of FIG. 26 in order to graphically indicate the static acuity of the subject 18 to the clinician. Referring again to FIG. 26, it can be seen that the test results data is provided in tabular form (i.e., table 712) in the lower central portion of the test report 700. The table 712 in FIG. 26 has a total of three (3) columns. The left column 714 of the table 712 lists the trial number (i.e., trials nos. 1 through 14), the middle column 716 of the table 712 lists the optotype size (i.e., in log MAR or relative log MAR), and the right column 718 of the table 712 lists whether or not the patient response was correct or incorrect for each of the trials in the table 712. Advantageously, the table 712 allows the operator or clinician to quickly ascertain the subject's numerical results for the first static set of trials.

After determining the size parameter of the first threshold version of the optotype in step 410 above, and generating and displaying the quantitative results in steps 412 and 414, the visual processing time of the subject 18 may be determined by the computing device 102, 202, 302 in steps 416-422 of FIGS. 11A and 11B. The purpose of this test is determine how long the optotype needs to be displayed on the screen of the visual display device 104, 204, 304 in order for the subject 18 to comprehend the displayed orientation of the optotype. Like the first set of successive trials described above, the visual processing time test is a static-type test, so there are no head movements made by the subject or patient during the performance of the visual processing time test. The size scale factor of the first threshold version of the optotype (e.g., in units of log MAR or relative log MAR) that was determined in conjunction with the first set of successive trials described above is used by the visual processing time test. In particular, the optotype size during the performance of the visual processing time test is determined by increasing the optotype size determined in conjunction with the first set of successive trials by two sizes (e.g., by 0.2 log MAR). This optotype size remains constant for all trials of the visual processing time test. The variable in the visual processing time test is the time duration during which the optotype is displayed on the screen. The stimulus level (i.e., selected display time of the optotype on the screen) may be determined by the computing device 102, 202, 302 using the same parameter estimation algorithm (e.g., Best-PEST algorithm) that selects the optotype size in the first set of successive trials described above and in the dynamic trials during the dynamic visual acuity (DVA) test described hereinafter. The same parameter estimation algorithm (e.g., Best-PEST algorithm) also may be used by the computing device 102, 202, 302 to determine the stimulus level (i.e., target head velocity) in the gaze stabilization test (GST) described hereinafter.

In one or more exemplary embodiments, during the visual processing time test, the shortest amount of time that the optotype is displayed on the screen of the visual display device 104, 204, 304 is twenty (20) milliseconds (i.e., because of the monitor refresh rate), while the maximum amount of time that the optotype is displayed on the screen of the visual display device 104, 204, 304 is seventy (70) milliseconds. The upper limit of seventy (70) milliseconds was selected because, if the subject or patient has a visual processing time greater than 70 milliseconds he or she will be unable to complete the dynamic trials of the dynamic visual acuity (DVA) test and gaze stabilization test (GST). An individual with a visual processing time greater than 70 milliseconds would be unable to complete these dynamic trials because the optotype must be displayed on the visual display device 104, 204, 304 while the head of the subject or patient is being displaced. If the display time of the optotype needed to be much longer than 70 milliseconds, it would not be possible to display the optotype only during the subject's head movement, and conversely, to not display it when the subject's head is at maximum amplitude and head velocity is zero (0).

Figure 18:
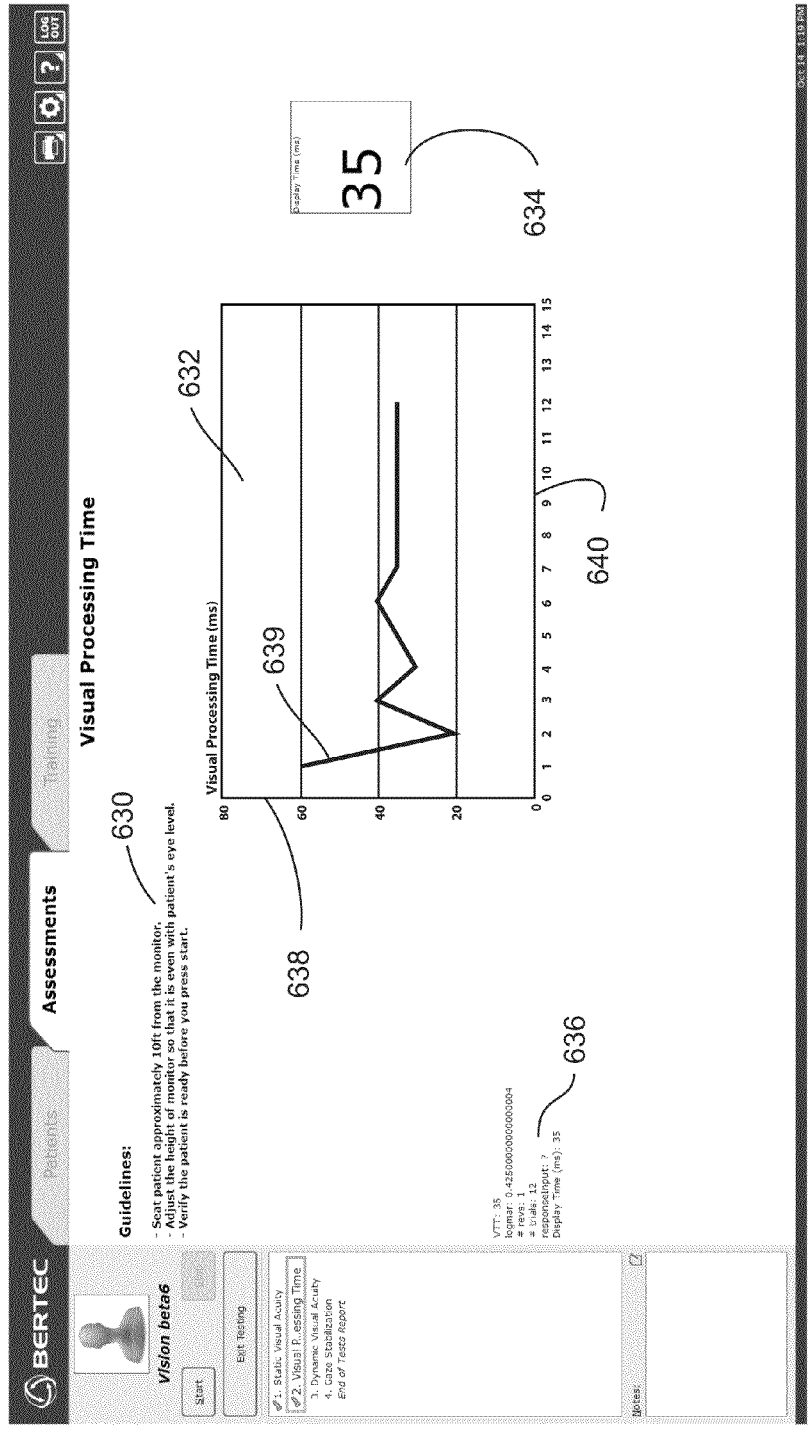
FIG. 18 is a second exemplary operator screen image of the visual display device, which may be displayed during the performance of a visual processing time test, according to an embodiment of the invention.

An exemplary operator or clinician screen image 628, which may be displayed on the visual display device 104, 204, 304 during the performance of the visual processing time test when the subject 18 maintains the generally fixed position of his or her head 30, is shown in FIG. 18. In one or more embodiments, the computing device 102, 202, 302 may be specially programmed to generate the screen image 628 of FIG. 18 during the visual processing time (VPT) test. With reference to FIG. 18, it can be seen that testing guidelines 630 may be displayed at the top of the screen image 628. The testing guidelines may specify a suggested distance or distance range (e.g., approximately ten (10) feet or between eight (8) and sixteen (16) feet) for the placement of the subject 18, visual display device height adjustment instructions, and additional instructions regarding the readiness of the subject. In one or more embodiments, the computing device 102, 202, 302 may be specially programmed to prompt the operator or clinician to input the step change (i.e., resolution) in the visual processing time between trials. The default test setting for the resolution may be ten (10) milliseconds, while the computing device 102, 202, 302 may be specially programmed to accept a resolution range between ten (10) milliseconds and fifty (50) milliseconds, inclusive. As additionally shown in FIG. 18, a graph 632 is also displayed in the center of the screen in order to visually illustrate the visual processing time (e.g., in milliseconds) of the subject 18 for each successive trial while the subject's head 30 remains stationary. That way, the operator or clinician is able to easily view the subject's performance during the progression of the testing. As shown in FIG. 18, the y-axis 638 of the graph 632 is the visual processing time (e.g., in milliseconds) of the subject 18, while the x-axis 640 of the graph 632 is the trial number of the visual processing time test (i.e., while the head 30 of the subject 18 remains stationary). In the graph 632 of FIG. 18, it can be seen that, after several abrupt fluctuations at beginning of the test, the stimulus level curve 639 tends to level out around thirty-five (35) milliseconds. Referring again to FIG. 18, it can be seen that the small box 634 on the right center of the clinician screen image 628 is configured to display the subject's visual processing time (e.g., in milliseconds) during the current trial of the testing procedure. Advantageously, the display of the subject's visual processing time in the small box 634 allows the clinician to quickly ascertain the subject's current performance level during the execution of the test. In the screen image 628 of FIG. 18, test summary data 636 is displayed below, and to the left of the graph 632 on the screen. For example, as shown in FIG. 18, the test summary data 636 may include the visual processing time, optotype size in units of log MAR, the number of reversals, the number of trials, and the display time in milliseconds. In one or more embodiments, some values of the test summary data may be automatically completed as each of the test portions is successively completed (e.g., static visual acuity, visual processing time, dynamic visual acuity, and gaze stabilization).

After the operator or clinician enters a start command to the computing device 102, 202, 302 by depressing a particular key on the keyboard, the visual processing time test begins. Turning again to the flowchart of FIG. 11A, it can be seen in step 416 that, while the subject 18 maintains a generally fixed position of his or her head 30 (i.e., keeping his or her head 30 as still as possible), one or more configurations of the visual object 10 are displayed on the output screen of the visual display device 104, 204, 304 for an initial display time (e.g., the optotype is displayed for ninety (90) milliseconds on the screen). For example, referring to FIG. 5, one or more configurations 10*a*, 10*b*, 10*c*, 10*d* of the Landolt C optotype may be displayed one-at-time on the output screen of the visual display device 104, 204, 304 for an initial display time. In an alternative exemplary embodiment, with reference to FIG. 6, one or more configurations 10'*a*, 10'*b*, 10'*c*, 10'*d* of the Tumbling E optotype may be displayed one-at-time on the output screen of the visual display device 104, 204, 304 for an initial display time. In other exemplary embodiments, other suitable optotypes may be used in place of the Landolt C or the Tumbling E, such as letters of a recognized alphabet (e.g., the English alphabet). In one or more embodiments, the visual object 10 (i.e., optotype) is displayed in approximately 500 milliseconds after the operator or clinician enters the start command to the computing device 102, 202, 302. After the visual object (i.e., optotype) disappears from the output screen of the visual display device 104, 204, 304, the computing device 102, 202, 302 may be specially programmed to implement a wait state, wherein the computing device 102, 202, 302 waits for the operator or clinician to record the subject's response.

During the visual processing time test, the same solid black circle 618 and crosshairs 620, which was described above in conjunction with FIGS. 16 and 17, is used to present the optotype to the subject 18. That is, the patient screen during the visual processing time test is generally the same as the screen images 614, 626 in FIGS. 16 and 17.

Now, with reference to FIG. 11B, in step 418, the computing device or data processing device 102, 202, 302 determines whether or not the subject 18 correctly identifies the one or more configurations (e.g., 10'*a*, 10'*b*, 10'*c*, 10'*d*) of the visual object 10' that is displayed on the visual display device 104, 204, 304 for the initial display time. For example, the subject 18 may be presented with a single optotype 10'*b* pointing down (see FIG. 6). After the optotype is displayed to the subject 18, the subject 18 or the clinician 14 may utilize a user input device 24 (e.g., a wireless mouse) in order to transmit the response of the subject 18 to the computing device 102, 202, 302 (e.g., the wireless mouse may have four buttons, each of which corresponds to one of the four configurations of the optotype). Alternatively, the response of the subject 18 may be entered using the keyboard of the computing device 102, 202, 302 by using the directional arrows and space bar on the keyboard. For example, the "up" arrow key on the keyboard is used to record an optotype pointing up, the "down" arrow key on the keyboard is used to record an optotype pointing down, the "left" arrow key on the keyboard is used to record an optotype pointing to the left, the "right" arrow key on the keyboard is used to record an optotype pointing to the right, and the spacebar is used to record an unknown orientation of the optotype. If the space bar is depressed on the keyboard, the computing device 102, 202, 302 randomly chooses the response of the subject 18. After receiving the subject's response, the computing device 102, 202, 302 is specially programmed to determine if the subject correctly determined the configuration of the optotype that was displayed on the output screen of the visual display device 104, 204, 304. For example, if the optotype 10'*b* of FIG. 6 was displayed on the screen, the subject 18 must indicate that optotype is pointing down to get the identification correct. Any other answer would be incorrect for this configuration of the optotype. Once the subject's answer or response is evaluated as to its correctness, the computing device 102, 202, 302 is specially programmed to record whether or not the subject 18 identified the optotype correctly. In one exemplary embodiment, if the subject 18 identifies the configuration of the optotype 10'*b* correctly, the computing device 102, 202, 302 is specially programmed to display one or more subsequent optotypes for a display time that is shorter than the initial display time (e.g., the second trial may display the subsequent optotype on the screen for a display time of only 50 milliseconds, rather than the 60 milliseconds that was used during the initial trial). Conversely, if the subject 18 identifies the configuration of the first optotype 10'*b* incorrectly, the computing device 102, 202, 302 is specially programmed to display one or more subsequent optotypes for a display time that is longer than the initial display time (e.g., the second trial may display the subsequent optotype on the screen for a display time of 70 milliseconds, rather than the 60 milliseconds that was used during the initial trial). Also, in one or more embodiments, the computing device 102, 202, 302 is specially programmed to display the successive optotype on the screen approximately five-hundred (500) after it receives the subject's response regarding the preceding optotype.

In this manner, as specified in step 420 of FIG. 11B, the computing device 102, 202, 302 is specially programmed to incrementally decrease or increase the display time for the visual object on the output screen of the visual display device 104, 204, 304 during a set of successive trials (e.g., during a maximum number 624 of fourteen (14) trials as indicated in FIGS. 16 and 17). During the set of successive trials, various configurations of the same-sized visual object may be displayed on the output screen of the visual display device 104, 204, 304 for identification by the subject. For example, if the subject identifies a configuration of the same-sized optotype correctly, the screen display time for next-displayed optotype is generally decreased, while the screen display time for next-displayed optotype is generally increased if the subject fails to correctly identify the configuration of the optotype correctly. In the exemplary embodiment, after each optotype is displayed on the output screen of the visual display device 104, 204, 304 for a particular display time, the computing device 102, 202, 302 is specifically programmed to determine whether or not the subject 18 correctly identified the configuration of the optotype. In step 422 of FIG. 11B, after the subject 18 has completed a predetermined number of trials of optotype identification, the computing device 102, 202, 302 is specifically programmed to determine a threshold visual processing time for the subject 18 based upon the performance of the subject 18 during the set of successive trials during which the subject 18 maintained the generally fixed position of his or her head 30. For example, after a particular end condition is reached, the computing device 102, 202, 302 determines that the visual processing time for the subject 18 is fifty-five (55) milliseconds. In one embodiment, the visual processing time for the subject 18 is a calculated value that is determined using one or more statistical equations or formulas (e.g., using a Best-PEST algorithm as described hereinafter).

As described above for the first set of successive trials, the computing device 102, 202, 302 may be specifically programmed with multiple end conditions for determining when to end the second set of successive trials. For example, the computing device 102, 202, 302 may automatically stop the second set of successive trials as soon as any one or combination of the following conditions occur: (i) the subject has completed a total of fourteen (14) trials of optotype identification (i.e., a maximum allowable number of trials is reached), (ii) a predetermined number of reversals has occurred (refer to explanation above), or (iii) the user has stopped the first set of successive trials (e.g., the operator or clinician initiates the cessation of the successive trials by depressing a particular key on the keyboard).

Then, in step 424 of FIG. 11B, the computing device 102, 202, 302 is specifically programmed to generate a quantitative assessment of the subject's performance during the visual processing time test, and finally, in step 426 of FIG. 11B, to output the quantitative assessment of the subject's performance during the visual processing time test on the output screen of the visual display device 104, 204, 304. For example, in an exemplary embodiment, the computing device 102, 202, 302 may generate a report 720, such as that illustrated in FIG. 27, in order to display the test results from the visual processing time test.

Figure 27:
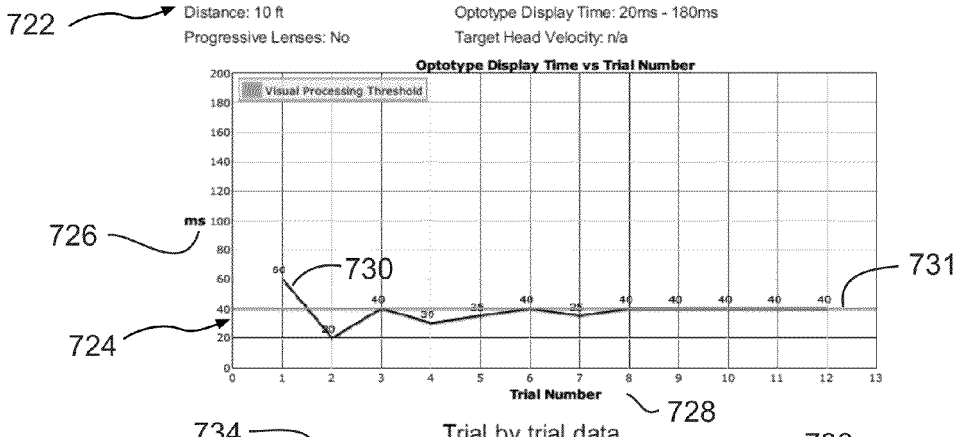
FIG. 27 is a sixth exemplary operator screen image of the visual display device, which illustrates an exemplary report generated by the vision testing system for displaying the results from a visual processing time test, according to an embodiment of the invention.

With reference to FIG. 27, the content of an exemplary test report for the visual processing time test will be described. As shown in FIG. 27, it can be seen that selected test parameters 722 may be displayed at the top of the screen image 720. As described above for the test report 700, the test parameters 722 may include: (i) the direction of head rotation during dynamic portions of the DVA test (i.e., about the yaw axis 66 of FIG. 10), (ii) the approximate distance (e.g., in feet) between the subject and the visual display device 104, 204, 304, (iii) whether or not progressive or corrective lenses (i.e., glasses or contact lens) are worn by the subject, (iv) the optotype size during the visual processing time test (e.g., in log MAR), (v) the optotype display time in milliseconds (e.g., as determined during the visual processing time (VPT) test) or display time range during the VPT test, and (vi) the target head angular velocity range for the subject during dynamic portions of the DVA test (e.g., in degrees per second). As additionally shown in FIG. 27, a graph 724 is also displayed in the upper central portion of the screen in order to visually illustrate the visual processing time (e.g., in milliseconds) of the subject 18 for each successive trial while the subject's head 30 remains stationary. That way, the operator or clinician is able to easily observe any trends that occurred during the testing (i.e., consistent incorrect answers, consistent correct answers, etc.) and to easily assess whether or not the testing results follow a normal trend (e.g., transient response-type curve as explained hereinafter). As shown in FIG. 27, the y-axis 726 of the graph 724 is the visual processing time (e.g., in milliseconds) of the subject 18, while the x-axis 728 of the graph 724 is the trial number of the visual processing time test (i.e., while the head 30 of the subject 18 remains stationary). In the graph 724 of FIG. 27, it can be seen that, after several abrupt fluctuations at beginning of the test, the stimulus level curve 730 tends to level out around forty (40) milliseconds. A horizontal line 731 is drawn at a visual processing time of 40 milliseconds in the graph 724 of FIG. 27 in order to graphically indicate the visual processing threshold time of the subject 18 to the clinician. Referring again to FIG. 27, it can be seen that the test results data is provided in tabular form (i.e., table 732) in the lower central portion of the test report 720. Like the table 712 described above with regard to FIG. 26, the table 732 in FIG. 27 has a total of three (3) columns. The left column 734 of the table 732 lists the trial number (i.e., trials nos. 1 through 12), the middle column 736 of the table 732 lists the display time (i.e., in milliseconds), and the right column 738 of the table 732 lists whether the patient response was correct or incorrect for each of the trials in the table 732. Advantageously, the table 732 allows the operator or clinician to quickly ascertain the subject's numerical results for the second static set of successive trials performed in conjunction with visual processing time test.

Referring again to FIG. 11B, the dynamic portion of the dynamic visual acuity test will be explained in detail. Initially, in step 428 of FIG. 11B, while the subject 18 displaces his or her head 30 at a velocity or speed within a predetermined range (e.g., between 85 and 120 degrees per second) as measured by the motion sensing device 28, one or more configurations of the optotype 10 having a third initial size are displayed on the output screen of the visual display device 104, 204, 304. For example, as explained above for the series of tests when the subject's head remains stationary, different configurations of the Landolt C optotype may be displayed one-at-time on the output screen of the visual display device 104, 204, 304. In one exemplary embodiment, the displacement of the subject's head 30 may comprise rotating the subject's to the right, and to the left, about the yaw axis 66 of FIG. 10 (i.e., approximately in a horizontal plane). The subject 18 may rotate his or head 30 on his or her own, or alternatively, the clinician 14 may rotate the subject's head 30 with his or her hands 32 so that it is easier to maintain the subject's head rotation within the predetermined range (see e.g., FIGS. 1 and 3). In one embodiment, the optotype 10 is only displayed on the output screen of the visual display device 104, 204, 304 when the head 30 of the subject 18 is being rotated within the predetermined angular velocity range (e.g., between 85 and 120 degrees per second) for a requisite number of head sweeps. Initially, the subject 18 may be instructed to slowly begin moving his or her head 30 in the selected direction (i.e., left or right), and to gradually increase the rotational velocity until the grayscale color of the outer circle on the screen matches the grayscale color of the inner circle on the screen. In one or more embodiments, a Tumbling E optotype is displayed after the subject 18 gets the three (3) required head sweeps in a predetermined target velocity range (e.g., 85 deg./sec. to 120 deg./sec.). During the dynamic portion of the DVA test, the computing device 102, 202, 302 may be specially programmed to randomly choose the orientation of the optotype that is displayed on the screen. Also, during the dynamic portion of the DVA test, the computing device 102, 202, 302 may be specially programmed to randomly choose whether to display the optotype on a left head turn or a right head turn. In addition, the first visual indicators 50, 51, and 60 described above in conjunction with FIGS. 7-9 may be used to ensure that the subject's head 30 is rotated within the predetermined velocity range, while the second visual indicator 48 may be used to ensure that the subject's head 30 is rotated within the prescribed range of motion (e.g., between 20 degrees to the left and 20 degrees to the right, or between 30 degrees to the left and 30 degrees to the right). Alternatively, the visual indicators described hereinafter in conjunction with FIGS. 21-24 may be used to ensure that the subject's head 30 is rotated within the predetermined velocity range.

After the optotype disappears during the dynamic portion of the DVA test, the subject 18 continues to shake his or her head, but gives an orientation response to the operator or clinician identifying the orientation of the optotype that appeared on the screen. During the dynamic portion of the DVA test, the subject 18 is also permitted to stop rotating his or her head 30, which results in the DVA test entering into a "pause" state. If the "pause" state is initiated, the computing device 102, 202, 302 is specially programmed to indicate a detected zero (0) head velocity at the bottom of the screen, and to further generate instructions on the screen that instruct the subject to resume rotating his or her head when ready. In one or more embodiments, approximately five-hundred (500) milliseconds after the operator or clinician records the orientation response of the subject 18, the next trial of the DVA test begins, wherein another optotype is displayed after the subject 18 gets the three (3) required head sweeps in the predetermined target velocity range. If a trial of the DVA test lasts for more than eight (8) seconds, the computing device 102, 202, 302 may be specially programmed to interrupt the trial, and to mark the trial as "unable to complete".

Figure 10:
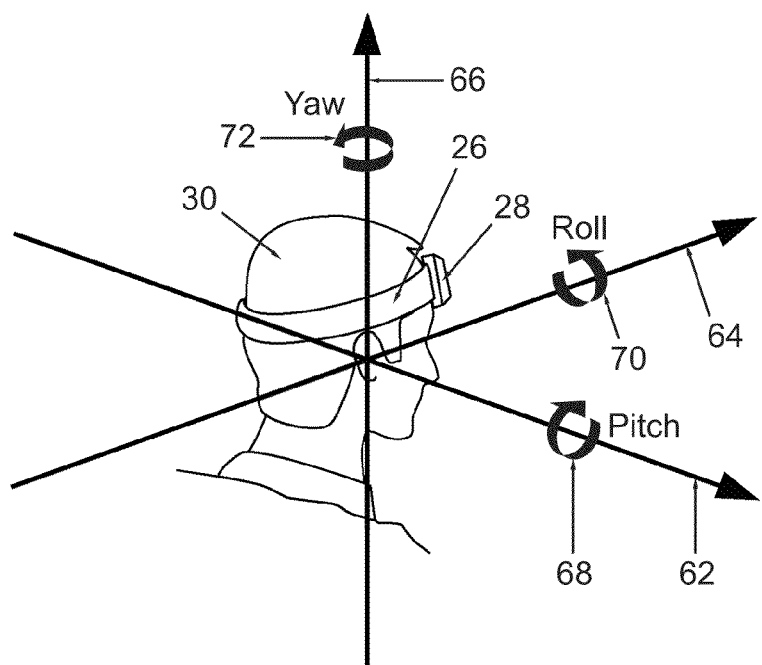
FIG. 10 is a diagrammatic view of the directions of subject head rotation that are capable of being measured with the motion sensing device of the vision testing system described herein.

In alternative exemplary embodiments, rather than rotating his or her head 30 about the yaw axis 66 in FIG. 10, the subject 18 may alternatively rotate his or her head 30 about the pitch axis 62 (i.e., approximately in a vertical plane) or about the roll axis 64 (i.e., in a roll plane). The computing device 102, 202, 302 is specially programmed to allow the user to selectively choose any one of these rotational directions when performing the dynamic portion of the dynamic visual acuity (DVA) test. In one embodiment, when the rotation about the pitch axis 62 is selected the optotype 10 is only displayed on the output screen of the visual display device 104, 204, 304 when the head 30 of the subject 18 is being rotated within a predetermined angular velocity range (e.g., between 60 and 85 degrees per second).

In one or more embodiments, a baseline visual processing time and static visual acuity value must have been previously stored in the computing device 102, 202, 302 in order to permit the subject 18 to perform the dynamic portion of the dynamic visual acuity (DVA) test. For example, if no baseline visual processing time and static visual acuity was previously determined on the day of the DVA test, the subject 18 must first complete the static visual acuity testing and the visual processing time testing prior to performing the dynamic portion of the dynamic visual acuity (DVA) test.

In one or more embodiments, during the dynamic portion of the dynamic visual acuity (DVA) test, as well as during the performance of the gaze stabilization test (GST) that will be described hereinafter, and during the DVA and GST practice modes, the head velocity of the subject 18, as measured by the motion sensing device 28, is used by the computing device 102, 202, 302 in order to determine when to display the optotype so that the optotype will generally be shown at a position centered around the subject's zero position. The subject's zero position is set at the beginning of each trial when the subject 18 is generally still and looking straight ahead at the visual display device 104, 204, 304. During the sweep in which the optotype (e.g., Landolt C optotype or Tumbling E optotype) will be shown, an optimal trigger angle is calculated by the computing device 102, 202, 302 at each sample based on the instantaneous angular velocity of the subject's head 30 and the length of time for which the optotype must be displayed. When the most recent angle calculated is reached, the optotype begins to show on the screen of the visual display device 104, 204, 304. The optimal trigger angle may be calculated by the computing device 102, 202, 302 as follows:

$$\theta_T = \frac{\dot{\theta}[(t)(10^{-3})]}{2} \tag{7}$$

where:

$\dot{\theta}$: instantaneous head velocity in the IMU plane of testing in degrees per second; and t: length of time in milliseconds (ms) that the optotype will be displayed on the screen. In the above equation (7), the optotype display time t may be calculated by adding thirty-five (35) milliseconds to the calculated visual processing speed (VPS) threshold time determined from the visual processing time test. The calculation described in equation (7) is iterated with each sample until the trigger angle $\theta_T$ is reached, in which case, the optotype is triggered to display. Because the subject's zero position is set when the subject 18 is generally still and looking straight ahead at the visual display device 104, 204, 304, the trigger angle $\theta_T$ calculated in equation (7) is divided by two (2). In one or more embodiments, if the visual processing speed (VPS) threshold time determined for the subject 18 is greater than forty (40) milliseconds, a high optotype display time is noted in the subject's report.

In one or more embodiments, the third initial size of the optotype 10 in the dynamic series of trials is larger than the first initial size of the optotype 10 in the first static series of trials. Because it is harder for a subject 18 to identify the optotype 10 during the dynamic series of trials when his or her head 30 is moving, as compared when his or her head is stationary in the first static set of trials, it makes sense to increase the size of the optotype 10 during the second set of trials so that it can be more easily identified by the subject 10. For example, in one embodiment, the third initial size of the optotype 10, 10' in the dynamic series of trials may have a size scale factor of 1.0 (e.g., optotypes 10*a*, 10*b*, 10*c*, 10*d* in FIG. 5 or optotypes 10'*a*, 10'*b*, 10'*c*, 10'*d* in FIG. 6), while the first initial size of the optotype 10, 10' in the first static series of trials may have a size scale factor of 0.75 (e.g., optotypes 10*e*, 10*f*, 10*g*, 10*h* in FIG. 5 or optotypes 10'*e*, 10'*f*, 10'*g*, 10'*h* in FIG. 6).

Figure 19:
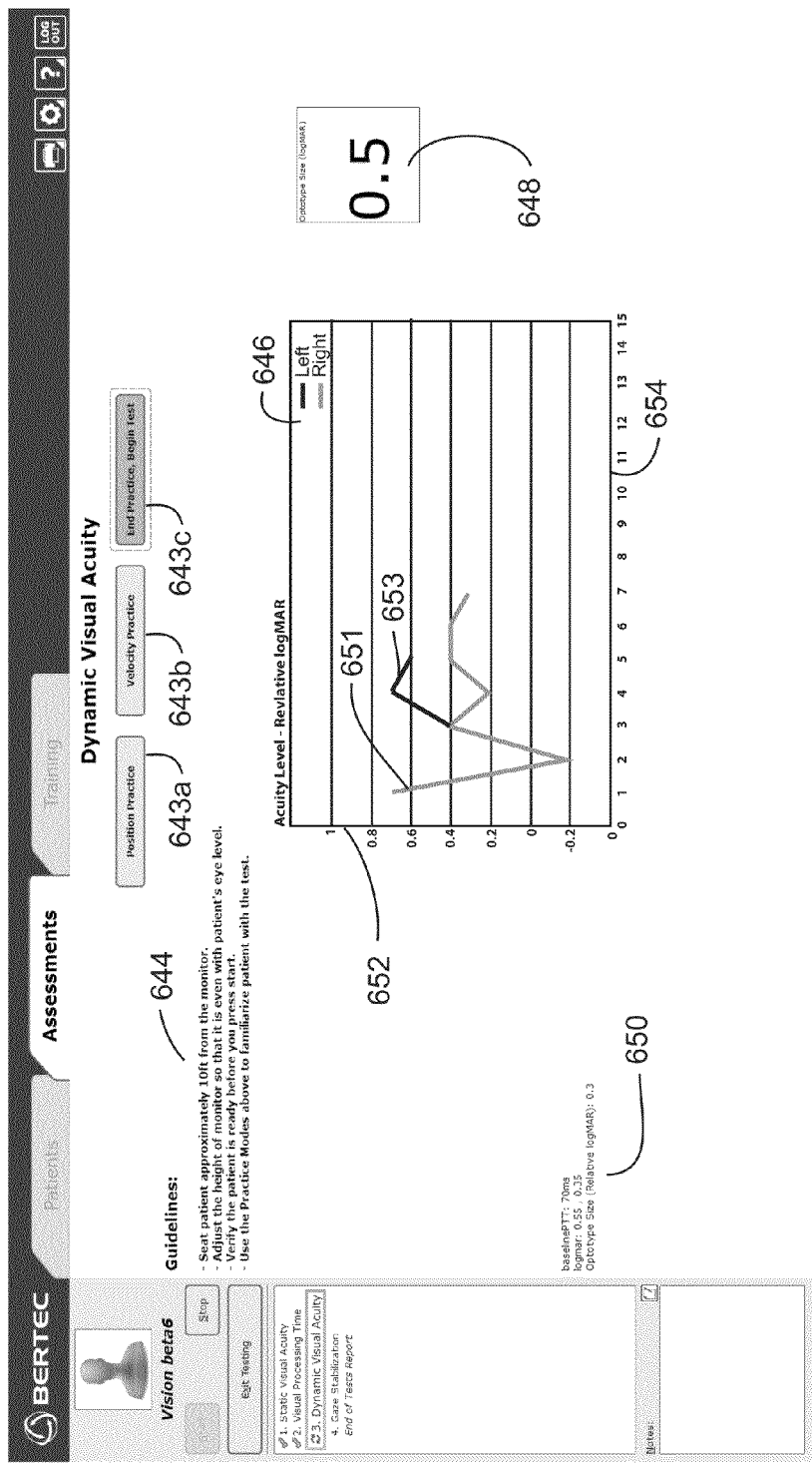
FIG. 19 is a third exemplary operator screen image of the visual display device, which may be displayed during the performance of a dynamic visual acuity test, according to an embodiment of the invention.

An exemplary operator or clinician screen image 642, which may be displayed on the visual display device 104, 204, 304 during the dynamic set of successive trials when the subject 18 rotates his or her head 30 within a predetermined angular velocity range, is shown in FIG. 19. In one or more embodiments, the computing device 102, 202, 302 may be specially programmed to generate the screen image 642 of FIG. 19 during the performance of this latter dynamic portion of the vision testing. As shown in FIG. 19, a set of on-screen virtual selection buttons 643*a*, 643*b*, 643*c* are provided at the top center of the screen for selecting one of: (i) a position practice mode (by clicking on button 643*a*), (ii) a velocity practice mode (by clicking on button 643*b*), and (iii) an actual DVA test mode (by clicking on button 643*c*). With reference again to FIG. 19, it can be seen that testing guidelines 644 may be displayed at the top of the screen image 642. The testing guidelines may specify a distance or distance range (e.g., approximately ten (10) feet or between eight (8) and sixteen (16) feet) for the placement of the subject 18, visual display device height adjustment instructions, instructions regarding the readiness of the subject, and additional instructions regarding the practice modes (the practice modes of the dynamic visual acuity test will be described hereinafter). In one or more embodiments, the computing device 102, 202, 302 may be specially programmed to prompt the operator or clinician to input the distance between the forehead of the subject and the front of the visual display device screen (e.g., in feet from the front of the screen). The default test setting for the distance may be ten (10) feet, while the computing device 102, 202, 302 may be specially programmed to accept a range of distances between eight (8) and sixteen (16) feet, inclusive. As additionally shown in FIG. 19, a graph 646 is also displayed in the center of the screen in order to visually illustrate the optotype size for each successive trial while the subject's head 30 is rotated to the left and right. That way, the operator or clinician is able to easily view the subject's performance during the progression of the testing. As shown in FIG. 19, the y-axis 652 of the graph 646 is the optotype size (e.g., in relative log MAR or log MAR), while the x-axis 654 of the graph 646 is the trial number of the dynamic set of successive trials (i.e., while the head 30 of the subject 18 is rotated to the left and right). In the graph 646 of FIG. 19, it can be seen that stimulus curves 651, 653 are provided for both the right and left directions of head movement. Referring again to FIG. 19, it can be seen that the small box 648 on the right center of the clinician screen image 642 is configured to display the optotype size (e.g., in log MAR or relative log MAR) during the current trial of the dynamic testing procedure. Advantageously, the display of the optotype size in the small box 648 allows the clinician to quickly ascertain the subject's current performance level during the execution of the test. In the screen image 642 of FIG. 19, test summary data 650 is displayed below, and to the left of the graph 646 on the screen. For example, as shown in FIG. 19, the test summary data 650 may include the baseline visual processing time (i.e., baseline PTT in milliseconds), the current DVA optotype size in units of log MAR for both left and right head rotation, and the relative optotype size for the static series of tests in units of realtive log MAR. In one or more embodiments, some values of the test summary data may be automatically completed as each of the test portions is successively completed (e.g., static visual acuity, visual processing time, dynamic visual acuity, and gaze stabilization).

Figure 20:
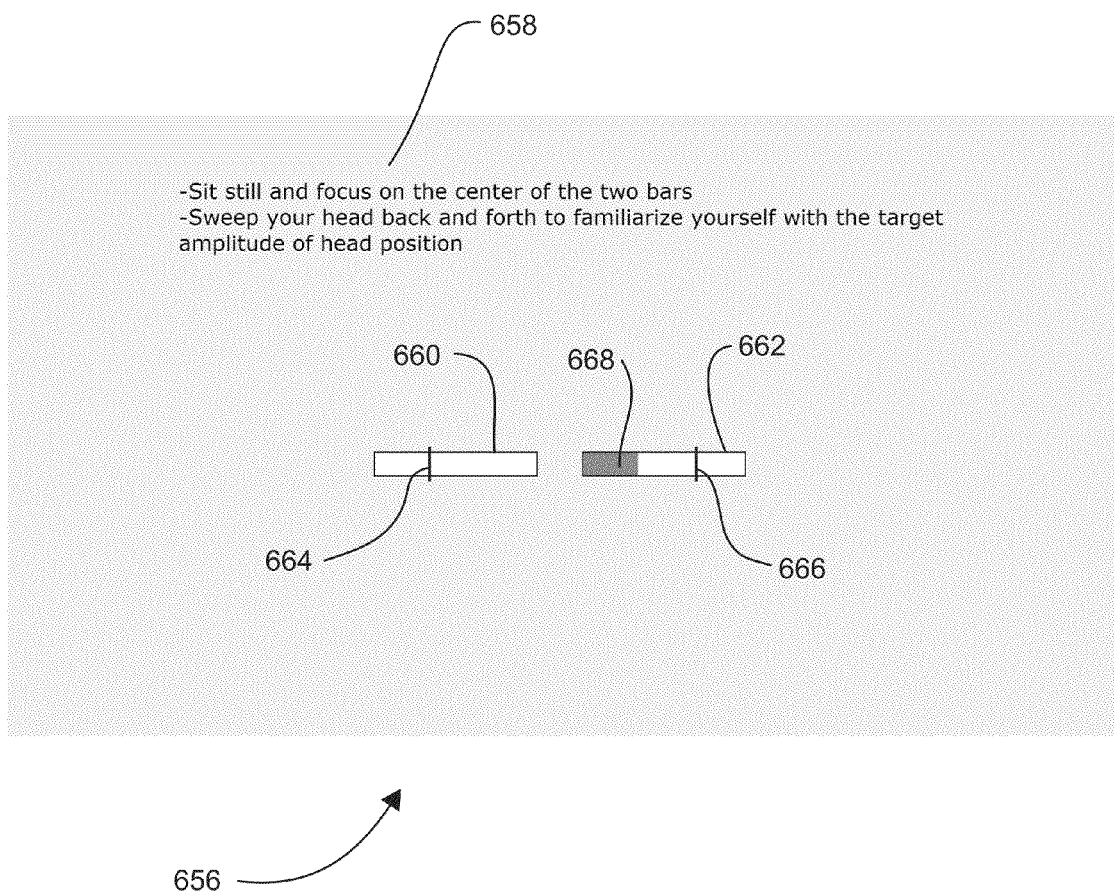
FIG. 20 is a subject practice screen image of the visual display device prior to the performance of a dynamic visual acuity test, which allows a subject to practice his or her amplitude of head displacement, according to an embodiment of the invention.

The practice mode of the dynamic visual acuity (DVA) test will be described in conjunction with FIG. 20. The practice mode walks subjects or patients through the required head movements for the DVA test. The first portion of the practice mode, namely position practice, focuses only on the head position of the subject or patient, allowing him or her to become familiar with the desired amplitude of head movement during the test. Referring to FIG. 20, it can be seen that the computing device 102, 202, 302 may be specially programmed to generate the screen image 656 during the position practice portion of the practice mode. In FIG. 20, it can be seen that practice guidelines 658 may be displayed at the top of the screen image 656. The practice guidelines may specify instructions regarding the focus direction of the subject 18, and additional instructions regarding the manner in which the practice exercise is to be performed by the subject 18. As additionally shown in FIG. 20, two rectangular boxes 660, 662 are also displayed in the center of the screen in order to visually illustrate the amplitude of head displacement to the subject 18. That way, the subject is able to easily determine if he or she is rotating his or her head using the proper amplitude. As shown in FIG. 20, each of the rectangular boxes 660, 662 is intersected by a respective vertical line 664, 666. The vertical lines 664, 666 are used to indicate the proper amplitude of the head displacement for the subject 18 during the position practice. The rectangular box 660 and its intersecting amplitude line 664 correspond to the left directional rotation of the subject's head 30, while the rectangular box 662 and its intersecting amplitude line 666 correspond to the right directional rotation of the subject's head 30. In FIG. 20, it can be seen that a displaceable indicator bar 668 is used to represent the rotational position of the subject's head 30. The displaceable indicator bar 668 in FIG. 20 indicates that the subject 18 is displacing his or her head to the right. Alternatively, if the subject 18 were displacing his or her head to the left, a displaceable indicator bar, which is similar to the bar 668 of FIG. 20, would appear within the rectangular box 660 on the left side of the screen image 656. During the position practice, the subject 18 is instructed to displace the visual indicator bar 668 between each of the amplitude lines 664, 666 (i.e., the subject 18 is instructed to displace the visual indicator bar 668 up to, but not past, each of the amplitude lines 664, 666 in succession, as he or she rotates his or her head 30 to the left, and to the right). For example, if the subject 18 displaces his or her head 30 with the proper amplitude to the right, the visual indicator bar 668 would reach the amplitude line 666, but not go past the amplitude line 666. However, if the amplitude of the subject's head displacement to the right is too large, the visual indicator bar 668 would go past the amplitude line 666 (i.e., the right edge of the visual indicator bar 668 would be displaced to the right of the amplitude line 666 on the screen). Conversely, if the amplitude of the subject's head displacement to the right is too small, the visual indicator bar 668 would not reach the amplitude line 666 (i.e., the right edge of the visual indicator bar 668 would lie to the left of the amplitude line 666 on the screen).

The second portion of the DVA practice mode, namely velocity practice, focuses on the head velocity of the patient. The second portion of the practice mode allows the patient to become familiar with the gray circle setup of the test, which will be explained hereinafter in conjunction with FIGS. 21-24. That is, during velocity practice, the subject 18 is able to practice matching the color of the outer circle to the target gray of the inner circle. Initially, the subject 18 may be instructed to slowly begin moving his or her head 30 in the selected direction (i.e., left or right), and to gradually increase the rotational velocity until the grayscale color of the outer circle on the screen matches the grayscale color of the inner circle on the screen. In one or more embodiments, a Tumbling E optotype is displayed after the subject 18 gets the three (3) required head sweeps in a predetermined target velocity range (e.g., 85 deg./sec. to 120 deg./sec.). During the velocity practice, the Tumbling E optotype is of a large size, it is always in the upright direction (pointing right), and it is displayed for a few hundred milliseconds to allow the subject 18 to focus on head velocity. Alternatively, the computing device 102, 202, 302 may be specially programmed to randomly choose the orientation of the optotype during the practice mode. Also, during the velocity practice mode, the computing device 102, 202, 302 may be specially programmed to randomly choose whether to display the optotype on a left head turn or a right head turn. After the optotype disappears during the practice mode, the subject 18 continues to shake his or her head, but gives an orientation response to the operator or clinician identifying the orientation of the optotype that appeared on the screen. During the practice mode, the subject 18 is also permitted to stop rotating his or her head 30, which results in the practice mode entering into a "pause" state. In one or more embodiments, approximately five-hundred (500) milliseconds after the operator or clinician records the orientation response of the subject 18, the next trial of the practice mode begins, wherein another optotype is displayed after the subject 18 gets the three (3) required head sweeps in the predetermined target velocity range. The practice mode may be continued until the subject 18 clearly understands the task that is being performed during the testing. The computing device 102, 202, 302 may be specially programmed to stop the practice mode when either the subject 18 or the operator presses the "ESC" key on the keyboard of the computing device 102, 202, 302.

Figure 21:
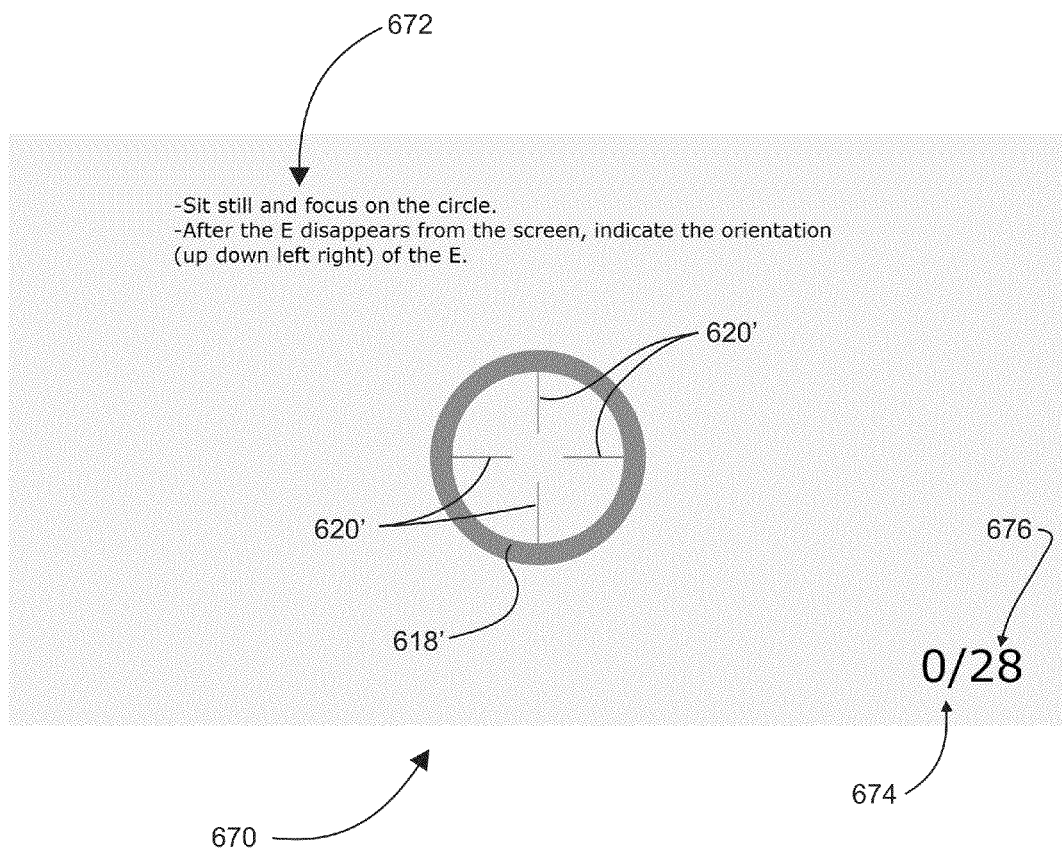
FIG. 21 is an initial subject screen image of the visual display device at the start of a dynamic visual acuity test or a gaze stabilization test, according to an embodiment of the invention.

With reference to FIGS. 21-24, exemplary subject screen images 670, 678, 682, 684 which may be displayed on the visual display device 104, 204, 304 and generated by the computing device 102, 202, 302 during the dynamic set of successive trials when the subject 18 rotates his or her head 30 within a predetermined angular velocity range, will now be described. Initially, referring to FIG. 21, it can be seen that a set of instructions 672 for the subject or patient may be displayed at the top of the screen image 670. The subject or patient instructions 672 may specify the manner in which the subject or patient is supposed to carry out the test (e.g., by instructing the patient to sit still and focus on the circle 618, and by instructing the patient to indicate the orientation of the optotype after it disappears from the screen). The set of instructions 672 may be initially displayed on the output screen by the computing device 102, 202, 302, and then subsequently hid from view (i.e., suppressed thereafter) so as not to unnecessarily distract the subject 18 during the testing. As additionally shown in FIG. 21, a solid gray circle 618' is displayed in the center of the screen. The circle 618' is generally the same as the circle 618 described above in conjunction with FIG. 16, except that it is gray in color rather than black. Like the circle 618 described above, the circle 618' of FIG. 21 also comprises a plurality of crosshairs 620' disposed therein, and extending inwardly towards the center of the circle 618'. The crosshairs 620' are generally the same as the crosshairs 620 described above in conjunction with FIG. 16, except that they are gray in color rather than black. Referring again to FIG. 21, it can be seen that, in the bottom right-hand corner of the screen, the number of trials 674 completed thus far, together with the maximum number of trials 676 that may be completed during the dynamic set of successive trials is displayed. Because FIG. 21 depicts the starting screen image 670 for the dynamic set of successive trials (i.e., when the subject's head is rotated to the left and to the right), the number 674 is zero (0) in FIG. 21. In this illustrative embodiment, the maximum number of trials 676 performed in conjunction with the dynamic set of successive trials is twenty-eight (28). However, it is to be understood that, in other embodiments of the invention, the maximum number of trials 676 performed in conjunction with the dynamic set of successive trials may be higher or lower than twenty-eight (28). Also, in an alternative embodiment, the small box 648 with the optotype size described above in conjunction with FIG. 19 and the small box 692 with the target head velocity described below in conjunction with FIG. 25 may be placed in the bottom right-hand corner of the screens 670, 678, 682, 684, rather than the number of trials 674 completed thus far, and the maximum number of trials 676. In this alternative embodiment, the number of trials 674 completed thus far, and the maximum number of trials 676 are placed in the test summary data 650, 694 on the respective operator or clinician screens 642, 686.

Figure 22:
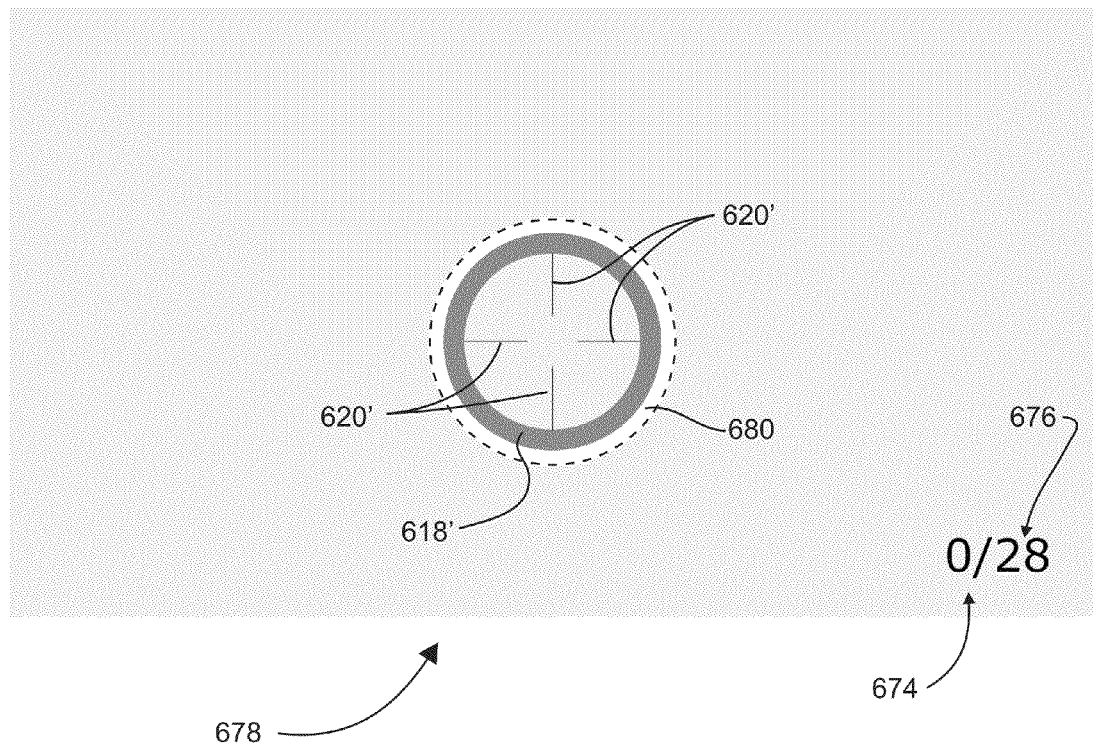
FIG. 22 is a subject test screen image of the visual display device at the start of a dynamic visual acuity test or a gaze stabilization test, wherein the subject is moving his or her head at an angular velocity that exceeds the desired range, according to an embodiment of the invention.
Figure 23:
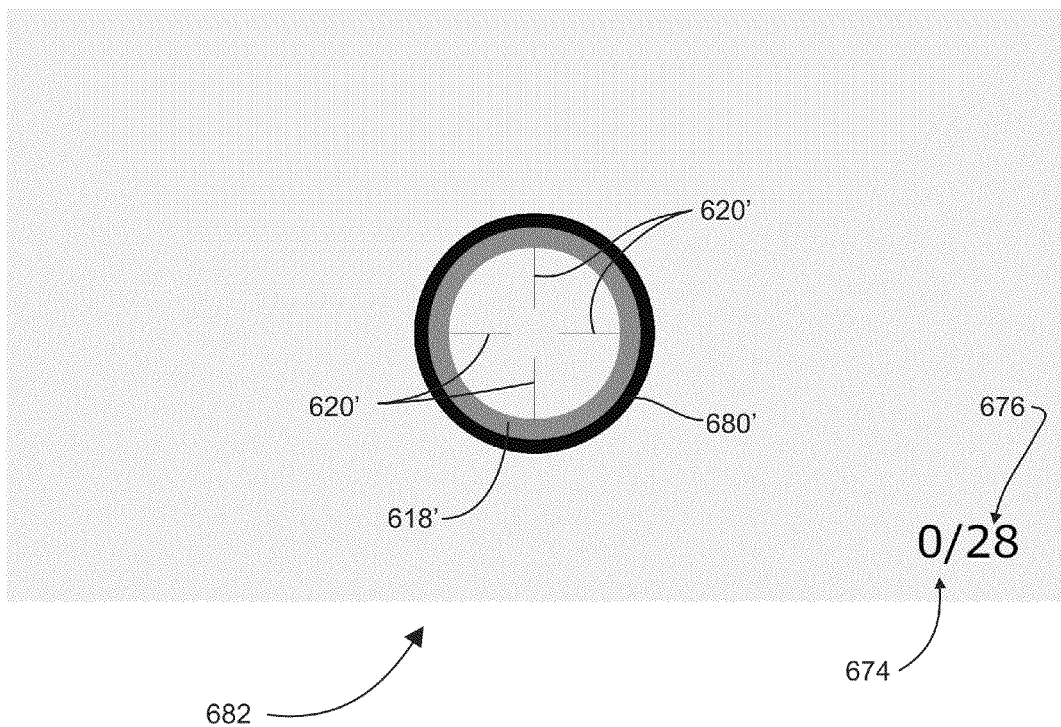
FIG. 23 is a subject test screen image of the visual display device at the start of a dynamic visual acuity test or a gaze stabilization test, wherein the subject is moving his or her head at an angular velocity that is less than the desired range, according to an embodiment of the invention.

Next, referring to FIG. 22, it can be seen that the screen image 678 is generally the same as the screen image 670 of FIG. 21, except that an outer white circle 680 is shown circumscribing the inner gray circle 618'. In FIG. 22, the outer white circle 680 is displayed on the visual display device 104, 204, 304 in order to indicate that the subject 18 is rotating his or her head at an angular velocity that exceeds the prescribed angular velocity range (i.e., the subject 18 is rotating his or her head 30 too fast). Conversely, the screen image 682 illustrated in FIG. 23 depicts a scenario wherein the subject 18 is rotating his or her head 30 at a velocity that is too slow. In FIG. 23, it can be seen that the screen image 682 is generally the same as the screen images 670, 678 of FIGS. 21 and 22, except that an outer black circle 680' is shown circumscribing the inner gray circle 618'. In FIG. 23, the outer black circle 680' is displayed on the visual display device 104, 204, 304 in order to indicate that the subject 18 is rotating his or her head at an angular velocity that is lower than the prescribed angular velocity range (i.e., the subject 18 is rotating his or her head 30 too slow).

Figure 24:
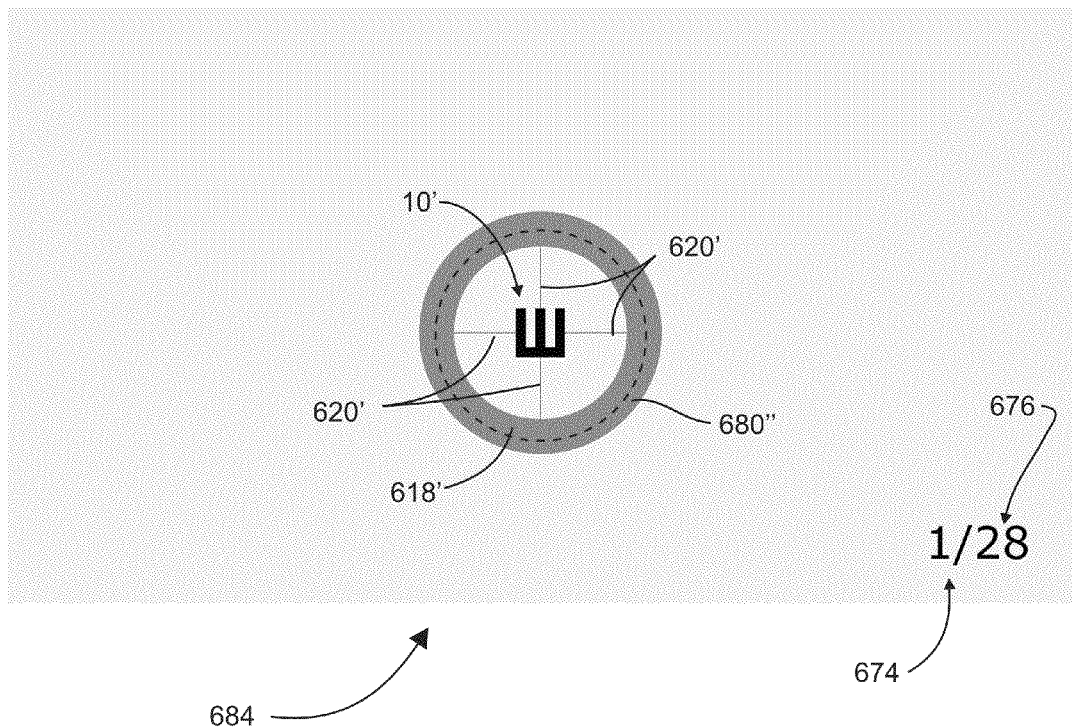
FIG. 24 is a subject test screen image of the visual display device during a dynamic visual acuity test or a gaze stabilization test, wherein the subject is moving his or her head at an angular velocity within the desired range, according to an embodiment of the invention.

Turning to FIG. 24, it can be seen that the screen image 684 is generally the same as the screen images 670, 678, 682 of FIGS. 21-23, except that an optotype 10' is displayed in the center of the circle 618', and the outer circle 680" of FIG. 24 is the same gray color as the inner circle 618'. While a Tumbling E optotype is utilized in the illustrative embodiment of FIG. 24, it is to be understood that, in an alternative embodiment, a Landolt C optotype or another type of optotype may be used in place of the Tumbling E optotype. In the exemplary screen image 684 of FIG. 24, it can be seen that the optotype is pointing up, so a correct identification of the optotype by the subject or patient would require that he or she indicates that the optotype is pointing up. As also depicted in FIG. 24, the number of trials 674 is equal to one (1) in order to indicate that the subject or patient has completed one trial of the dynamic set of successive trials (i.e., when the subject's head 30 is rotated to the left and to the right). In FIG. 24, because the outer circle 680" matches the same gray color as the inner circle 618', the subject 18 is rotating his or her head 30 within the prescribed angular velocity range for head movement during the test.

During the performance of the dynamic visual acuity (DVA) test, as well as during the performance of the gaze stabilization test (GST) that will be described hereinafter, the subject or patient needs information about their instantaneous head velocity while executing these tests. However, moving objects on the screen are visually distracting and increase the cognitive complexity of the test. In FIGS. 21-24, the inner circle 618' and crosshairs 620' are set to a "target" shade of gray, which corresponds to the target head velocity for the trial. The outer circle 680, 680', 680" changes to different shades of gray based on the instantaneous head velocity of the subject 18, with black being too slow and white being too fast. Therefore, the subject 18 must try to match the color of the outer circle 680, 680', 680" to the inner circle 618'. Grayscale was chosen instead of using different colors (e.g., red and green) for the inner and outer circles 618', 680 to further reduce the cognitive complexity of the test. It also eliminates the difficulties that would occur for subjects or patients with colorblindness.

After the subject or patient gets three (3) head sweeps that match the target head velocity range, the optotype 10' will appear in the center of the circle and crosshairs design (e.g., as shown in FIG. 24). This overall setup keeps the patient's gaze on one part of the screen (i.e., the center of the screen). Advantageously, the patient does not need to look to different parts of the screen for feedback on his or her head velocity and for the optotype display, which minimizes the impact of the patient's cognitive ability on the test results.

In one or more embodiments, the subject or patient screen images 670, 678, 682, 684 of FIGS. 21-24 may comprise a consistent background color throughout the testing (e.g., the background screen color may comprise a light blue color during all of the trials of the DVA test and the GST). However, in one or more alternative embodiments, the computing device 102, 202, 302 may be specially programmed to vary the contrast between the optotype (e.g., Tumbling E) displayed on the output screen of the visual display device 104, 204, 304 and the background of the output screen. For example, at the beginning of the varying contrast test, a black optotype may be displayed on a white or light blue background. However, during the performance of the test, the white or light blue background may be changed to a grey color or another color or grayscale that is closer to the color of the optotype itself. It is to be understood that, during the test, a plurality of different background colors or grayscale shades may be used in order to present the subject 18 with varying degrees of contrast between the optotype and the screen background. The contrast between the optotype and the screen background has a direct relationship to the subject's performance during the test. In one or more illustrative embodiments, the background color or shade of grayscale may be changed after the optotype is identified by the subject 18. The abovedescribed varying contrast test may be provided as another, separate test that is conducted in conjunction with the other tests described herein (e.g., the varying contrast test may be used in conjunction with a test series that includes both the DVA test and the GST).

In one or more embodiments, during the performance of the dynamic visual acuity (DVA) test and its practice modes, as well as during the performance of the gaze stabilization test (GST) and its practice modes that will be described hereinafter, the computing device 102, 202, 302 is specially programmed to generate an audio output signal that corresponds to the proper head sweeping of the subject 18, and to output that audio output signal to the speakers of the computing device 102 in order to assist the subject 18 with the proper head sweep timing that is required for the DVA and GST tests (i.e., a metronome plays from the speakers to assist the subject 18 with the execution of the head sweep timing). During the GST test, the metronome changes the beats per minute with each trial, based on the target head velocity of that trial. The metronome provides an audible indicator of the pace at which the subject's head should be rotated during the DVA and GST tests. As such, the metronome supplements the visual indicators (i.e., the change in the grayscale coloration of the outer circle 680, 680', 680" that was described above in conjunction with FIGS. 21-24) that is provided on the screen of the visual display device 104, 204, 304. The exact timing of the metronome will vary based upon the particular subject or patient being tested.

Referring again to the flowchart of FIG. 11B, the computing device or data processing device 102, 202, 302 determines whether or not the subject 18 correctly identifies one or more configurations (e.g., 10'a, 10'b, 10'c, 10'd) of the visual object 10' having the third initial size in step 430. For example, as described above with regard to the first static series of trials, the subject 18 may be presented with one or more optotypes having the third initial size (e.g. a single optotype 10'a pointing up). This optotype 10'a is of the third initial size, which may be a size scale factor of 1.0. After the optotype is displayed to the subject 18, the subject 18 or the clinician 14 may utilize a user input device 24 (e.g., a wireless mouse) in order to transmit the response of the subject 18 to the computing device 102, 202, 302 (e.g., the wireless mouse may have four buttons, each of which corresponds to one of the four configurations of the optotype). After receiving each of the subject's responses, the computing device 102, 202, 302 is specially programmed to determine if the subject correctly determined the configuration of the optotype that was displayed on the output screen of the visual display device 104, 204, 304. For example, if the optotype 10'a of FIG. 6 was displayed on the screen, the subject 18 must indicate that optotype is pointing up to get the identification correct. Any other answer would be incorrect for this configuration of the optotype. Once the subject's answer or response is evaluated as to its correctness, the computing device 102, 202, 302 is specially programmed to record whether or not the subject 18 identified the optotype correctly. As explained above with regard to the first static series of trials, in one exemplary embodiment, if the subject 18 identifies the configuration of the optotype 10'a correctly, the computing device 102, 202, 302 is specially programmed to display one or more optotypes having a physical size that is smaller than the first optotype (e.g., the second trial may comprise one or more optotypes that have a size scale factor of 0.75). For example, the second optotype may comprise the optotype 10'h in FIG. 6, which has a smaller size than the optotype 10'a in the top row of FIG. 6. Conversely, if the subject 18 identifies the configuration of the first optotype 10'a incorrectly, the computing device 102, 202, 302 is specially programmed to display one or more optotypes having a physical size that is larger than the first optotype (e.g., the second optotypes may have a size scale factor of 1.25).

In this manner, as set forth in step 432 of FIG. 11B, the computing device 102, 202, 302 is specially programmed to incrementally decrease or increase the size of the visual object (i.e., the optotype) on the output screen of the visual display device 104, 204, 304 during a third set of successive trials while the subject 18 displaces his or her head at a velocity or speed within the predetermined range as measured by the motion sensing device 28 (e.g., during a maximum number 676 of twenty-eight (28) trials as indicated in FIGS. 21-24). For example, if the subject identifies the configuration of a particular-sized optotype correctly, the optotype size of the next optotype displayed on the screen is generally decreased, while the optotype size of the next optotype displayed on the screen is generally increased if the subject fails to correctly identify the configuration of the optotype correctly. In the exemplary embodiment, after each optotype is displayed on the output screen of the visual display device 104, 204, 304, the computing device 102, 202, 302 is specifically programmed to determine whether or not the subject 18 correctly identified the configuration of the optotype.

In step 434 of FIG. 12, after the subject 18 has completed a predetermined number of trials of optotype identification, the computing device 102, 202, 302 is specifically programmed to determine a size parameter (e.g., a size scale factor) of a second threshold version of the optotype based upon the performance of the subject 18 during the third set of successive trials during which the subject 18 displaces his or her head 30. For example, after the subject completes a series of twenty-eight (28) trials of optotype identification, the computing device 102, 202, 302 determines that the second threshold version of the optotype has a size scale factor of 0.60.

In one or more embodiments, during the third set of successive trials during which the head 30 of the subject 18 is displaced, a second threshold version of the optotype is determined by the computing device 102, 202, 302 for both the right and left directions of head movement about the yaw axis 66 of the FIG. 10. That is, a second threshold version of the optotype is determined for the left rotation of the subject's head 30 about the yaw axis 66, and another second threshold version of the optotype is determined for the right rotation of the subject's head 30 about the yaw axis 66. For example, the second threshold version of the optotype for left rotation of the subject's head 30 may have a size scale factor of 0.60, while the second threshold version of the optotype for right rotation of the subject's head 30 may have a size scale factor of 0.80.

Next, in step 436 of FIG. 12, the computing device 102, 202, 302 is specifically programmed to compare the size parameter of the second threshold version of the visual object (i.e., the optotype) to the size parameter of the first threshold version of the visual object. In the illustrated embodiment, the computing device 102, 202, 302 compares the second threshold version of the optotype determined for both the right and left directions of head movement of the subject 18 to the size parameter of the first threshold version of the visual object. Then, in step 438 of FIG. 12, the computing device 102, 202, 302 is specifically programmed to generate a quantitative assessment of dynamic visual acuity loss using the size parameters of the first and second threshold versions of the visual object and finally, in step 440 of FIG. 12, to output the quantitative assessment of dynamic visual acuity loss of the subject 18 on the output screen of the visual display device 104, 204, 304. For example, in an exemplary embodiment, the computing device 102, 202, 302 may generate a report 740*a*, 740*b*, such as that illustrated in FIGS. 28A and 28B, in order to display the test results from the third dynamic set of successive trials. The dynamic visual acuity (DVA) testing procedure concludes at step 442 in FIG. 12.

Figure 28A:
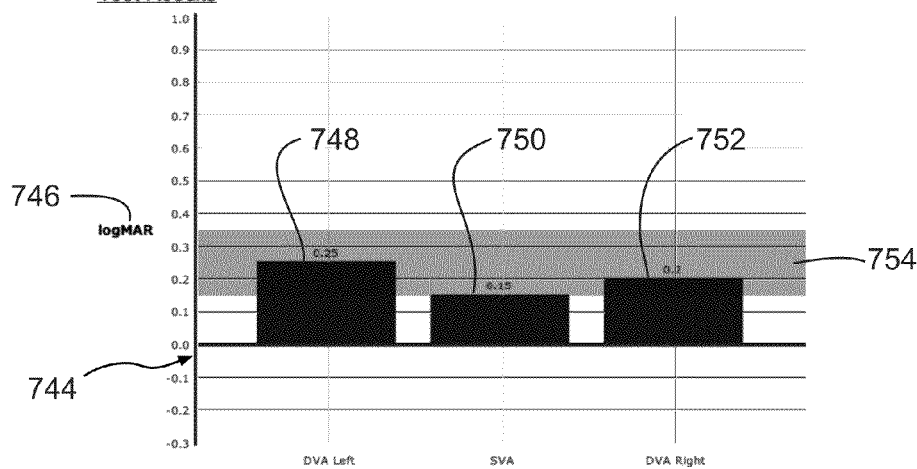
FIG. 28A is a seventh exemplary operator screen image of the visual display device, which illustrates a first part of an exemplary report generated by the vision testing system for displaying the results from a dynamic visual acuity test, according to an embodiment of the invention.
Figure 28B:
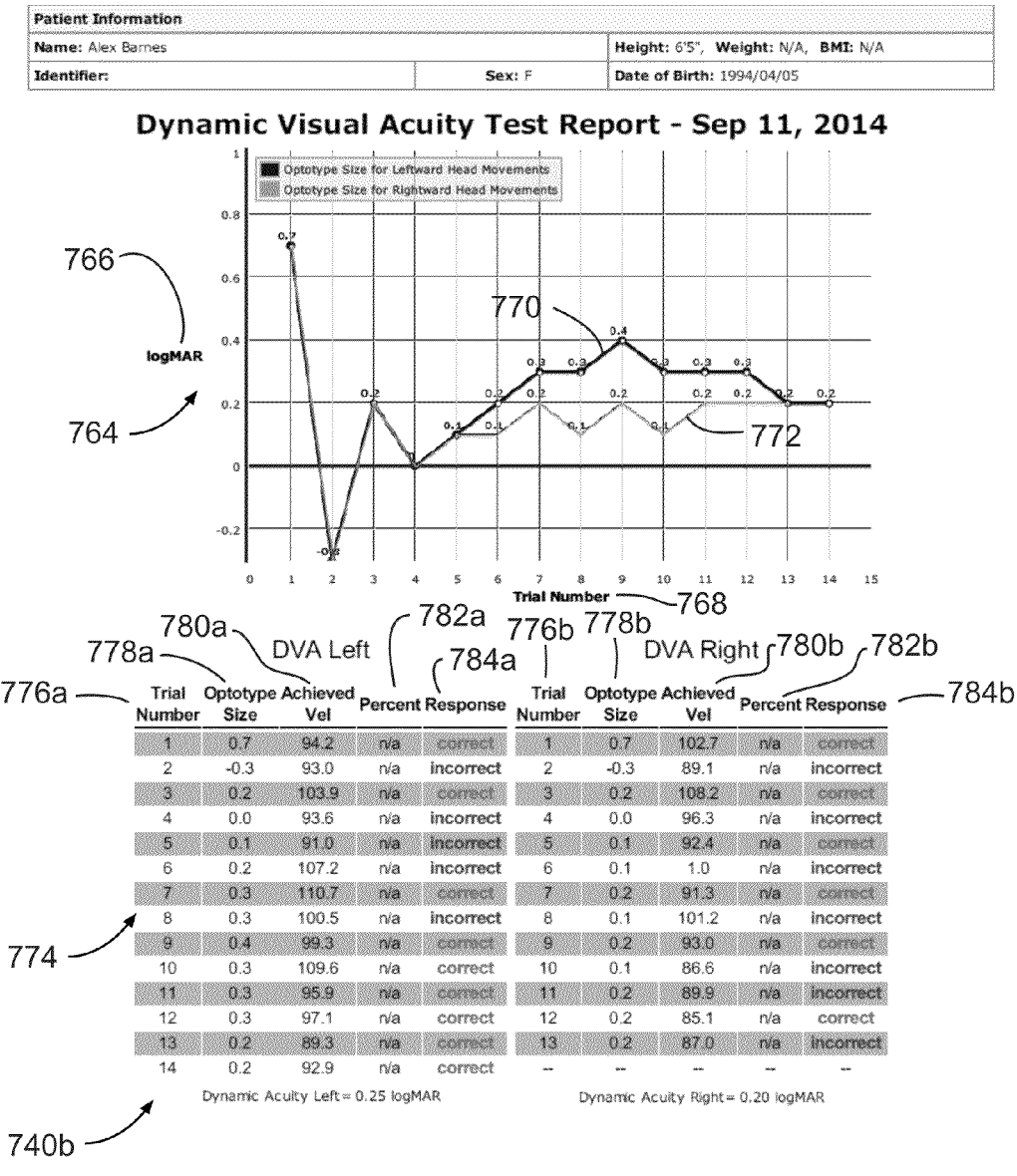
FIG. 28B is a seventh exemplary operator screen image of the visual display device, which illustrates a second part of an exemplary report generated by the vision testing system for displaying the results from a dynamic visual acuity test, according to an embodiment of the invention.

With reference to FIGS. 28A and 28B, the content of an exemplary test report for the third dynamic set of successive trials will be described. As shown in FIG. 28A, it can be seen that selected test parameters 742 may be displayed at the top of the screen image 740*a*. The test parameters 742 may include: (i) the direction of head rotation during dynamic portions of the DVA test (i.e., about the yaw axis 66 of FIG. 10), (ii) the approximate distance (e.g., in feet) between the subject and the visual display device 104, 204, 304, (iii) whether or not progressive or corrective lenses (i.e., glasses or contact lens) are worn by the subject, (iv) the optotype size range presented during the DVA test, (v) the optotype display time (e.g., as determined during the visual processing time test described above), and (vi) the target head angular velocity range for the subject during dynamic portions of the DVA test (e.g., in degrees per second). As additionally shown in FIG. 28A, a bar graph 744 is also displayed in the upper central portion of the screen in order to compare the optotype size parameters determined for the dynamic testing of the subject 18 to the optotype size parameter determined for the static testing of the subject 18. As shown in FIG. 28A, the y-axis 746 of the bar graph 744 is the optotype size (e.g., in log MAR or relative log MAR). The left bar 748 in the bar graph 744 corresponds to the size parameter that was determined for the second threshold version of the visual object (i.e., optotype) for a left rotational movement of the subject's head 30, namely 0.25 log MAR. The center bar 750 in the bar graph 744 corresponds to the size parameter that was determined for the first threshold version of the visual object (i.e., optotype) during the first static set of successive trials, namely 0.15 log MAR. The right bar 752 in the bar graph 744 corresponds to the size parameter that was determined for the second threshold version of the visual object (i.e., optotype) for a right rotational movement of the subject's head 30, namely 0.2 log MAR. The gray-colored horizontal band 754 that is superimposed on the bar graph 744 of FIG. 28A represents two lines of vision loss on the Snellen chart so that any abnormalities can be readily ascertained. A normal individual typically has no more than two lines of vision loss when the dynamic vision testing results of that individual are compared to the static testing results of that individual. As such, in FIG. 28A, the bottom edge of the gray-colored horizontal band 754 is aligned with the top edge of the static vision test bar 750 in order to clearly denote the "normal" range of values for the optotype size parameters determined during the dynamic portion of the vision testing. Thus, for the test results displayed in FIG. 28A, it can be seen that the subject's size parameters for both left and right head rotation (i.e., 0.25 log MAR and 0.20 log MAR, respectively) both lie within the normal range that is indicated by the gray-colored horizontal band 754. That is, the subject 18 who achieved the results displayed in FIG. 28A had less than two lines of vision loss for her dynamic vision testing results as compared to her static testing results. Consequently, the subject 18 who achieved the results displayed in FIG. 28A has normal or better than normal dynamic visual acuity as compared to the baseline population.

Referring again to FIG. 28A, it can be seen that the test results data is provided in tabular form (i.e., table 756) in the lower central portion of the test report 740*a*. The table 756 in FIG. 28A has a total of three (3) rows. The first row 758 of the table 756 lists the optotype size parameter (i.e., in log MAR) for DVA left head rotation, no head rotation (static baseline condition), and for DVA right head rotation. The second row 760 of the table 756 lists the average achieved head velocity (i.e., in degrees per second) for DVA left head rotation and for DVA right head rotation. The third row 762 of the table 756 lists the lines lost (i.e., in the Snellen chart) for DVA left head rotation and for DVA right head rotation.

Now turning to FIG. 28B, it can be seen that a graph 764 may be displayed in the top half of the screen image 740b, while a table 774 with the DVA test results in tabular form may be displayed in the bottom half of the screen image 740b. The graph 764 displayed in the top half of the screen image visually illustrates the optotype size (i.e., in log MAR or relative log MAR) for each successive trial while the subject's head 30 is rotated to the left and to the right. That way, the operator or clinician is able to easily observe any trends that occurred during the testing (i.e., consistent incorrect answers, consistent correct answers, etc.) and to easily assess whether or not the testing results follow a normal trend (e.g., transient response-type curve as explained hereinafter). As shown in FIG. 28B, the y-axis 766 of the graph 764 is the optotype size (e.g., in log MAR or relative log MAR), while the x-axis 768 of the graph 764 is the trial number of the dynamic set of successive of trials while the subject's head 30 is rotated to the left and to the right. In FIG. 28B, it can be seen that two curves 770, 772 are plotted on the graph 764. The first curve 770 is a plot of the test results for the left rotation of the head 30 of the subject 18, while the second curve 772 is a plot of the test results for the right rotation of the head 30 of the subject 18. At the beginning of the test, it can be seen that the two curves 770, 772 coincide with another (i.e., up to the fifth trial). However, after the fifth trial for both left and right head movement of the subject 18, the curves 770, 772 begin to deviate from one another (i.e., the tested optotype size is generally greater for the left head rotation between the fifth trial and thirteenth trial as compared to that tested for right head rotation). At the end of the dynamic set of successive trials, the curves 770, 772 generally coincide with one another in the same manner that they did at the beginning of the DVA test.

Next, with reference again to FIG. 28B, it can be seen that the test data, which is plotted in graph 764, is presented in tabular form (i.e., table 774) in the bottom half of the screen image 740b. The table 774 in FIG. 28B generally comprises a set of five (5) columns 776a, 778a, 780a, 782a, 784a on the left-hand side thereof, and another set of five (5) columns 776b, 778b, 780b, 782b, 784b on the right-hand side thereof. The five (5) columns 776a, 778a, 780a, 782a, 784a on the left-hand side correspond to the test results for the left rotation of the subject's head 30, while the five (5) columns 776b, 778b, 780b, 782b, 784b on the right-hand side correspond to the test results for the right rotation of the subject's head 30. The leftmost column 776a of the table 774 lists the trial number (i.e., trials nos. 1 through 14) for left head rotation, the next column 778a to the right lists the optotype size (i.e., in log MAR or relative log MAR) for left head rotation, the next column 780a to the right lists the angular velocity achieved during the left head rotation trial, the next column 782a to the right lists the percentage of the velocity that was in the plane of movement (i.e., about the yaw axis 66) for left head rotation, and the final column 784a corresponding to left head rotation lists whether or not the subject or patient response was correct or incorrect for each of the left rotation trials in the table 774. Similarly, the leftmost column 776b corresponding to right head rotation in the table 774 lists the trial number (i.e., trials nos. 1 through 13) for right head rotation, the next column 778b to the right lists the optotype size (i.e., in log MAR or relative log MAR) for right head rotation, the next column 780b to the right lists the angular velocity achieved during the right head rotation trial, the next column 782b to the right lists the percentage of the velocity that was in the plane of movement (i.e., about the yaw axis 66) for right head rotation, and the rightmost column 784b of the table 774 lists whether or not the subject or patient response was correct or incorrect for each of the right rotation trials in the table 774. Advantageously, the table 774 allows the operator or clinician to quickly ascertain the subject's numerical results for the dynamic set of trials performed during the DVA test.

In an alternative embodiment, prior to the step 438, wherein the computing device 102, 202, 302 generates a quantitative assessment of dynamic visual acuity loss using the size parameters of the first and second threshold versions of the visual object, the computing device 102, 202, 302 is further specifically programmed to determine a ratio of the size parameter of the second threshold version of the visual object (i.e., the optotype) to the size parameter of the first threshold version of the visual object. For example, the ratio $R_{SP}$ of the size parameter of the second threshold version of the optotype to the size parameter of the first threshold version of the optotype may be expressed by the following equation:

$$R_{SP} = \frac{SF_2}{SF_1} \quad (8)$$

where:

$SF_1$: size parameter or scale factor of the first threshold version of the optotype; and $SF_2$: size parameter or scale factor of the second threshold version of the optotype.

In these one or more alternative embodiments, the computing device 102, 202, 302 determines the ratio $R_{SP}$ of the size parameter for both the right and left directions of head movement of the subject 18. After the ratio of the size parameters between the first and second threshold versions of the visual object or optotype are determined, the computing device 102, 202, 302 further computes the base 10 logarithm of the ratio as follows to determine the dynamic visual acuity (DVA) loss using the following equation:

$$DVA_{loss} = \log_{10}(R_{SP}) \quad (9)$$

In these one or more alternative embodiments, the computing device 102, 202, 302 determines the dynamic visual acuity loss $DVA_{loss}$ for both the right and left directions of head movement of the subject 18.

In these one or more alternative embodiments, after the computing device 102, 202, 302 performs the calculations described above, the computing device 102, 202, 302 performs step 438 of FIG. 12, wherein the quantitative assessment of dynamic visual acuity loss $DVA_{loss}$ is generated thereby. In these one or more alternative embodiments, the quantitative assessment of dynamic visual acuity loss $DVA_{loss}$ generated by the computing device 102, 202, 302 is based upon the computed ratio of the size parameters of the first and second threshold versions of the visual object. Then, the process proceeds with step 440 of FIG. 12, wherein the computing device 102, 202, 302 outputs the quantitative assessment of dynamic visual acuity loss of the subject 18 on the output screen of the visual display device 104, 204, 304. For example, in these one or more alternative embodiments, the computing device 102, 202, 302 may generate a graph or chart that graphically depicts the computed dynamic visual acuity loss $DVA_{loss}$ value or values. In the alternative embodiments wherein the dynamic visual acuity loss $DVA_{loss}$ is determined for both the right and left directions of head movement of the subject 18, the graph or chart may graphically depicts the computed dynamic visual acuity loss for both the right and left movement directions. Advantageously, the graph or chart generated by the computing device 102, 202, 302 allows the clinician 14 to easily assess the amount of visual acuity loss that is realized when the subject 18 is moving his or her head 30, as compared to when the subject's head 30 is stationary. The computing device 102, 202, 302 may additionally generate another graph or chart that displays the dynamic visual acuity loss symmetry for the left and right directions of movement in terms of a percentage difference between the right and left directions of movement. For example, the percentage difference between the right and left directions of movement may be computed using the following equation:

$$\%_{Difference} = \left( \frac{DVA_{loss\_L} - DVA_{loss\_R}}{DVA_{loss\_L} + DVA_{loss\_R}} \right) \quad (10)$$

where:

$DVA_{loss\_L}$: dynamic visual acuity loss for the left direction of head movement; and $DVA_{loss\_R}$: dynamic visual acuity loss for the right direction of head movement.

Then, after computing the percentage difference between the right and left directions of movement, the computing device 102, 202, 302 is specially programmed to output the graph or chart that graphically displays the percentage difference between the right and left directions of movement on the output screen of the visual display device 104, 204, 304. In these one or more alternative embodiments, the dynamic visual acuity (DVA) testing procedure concludes at step 442 in FIG. 12.

In one or more embodiments, the size parameters of the first and second threshold versions of the visual object (e.g., the optotype 10) do not comprise a Snellen fraction. Because a Snellen fraction is not used for these size parameters, the subject 18 is capable of being tested using the vision testing systems 100, 200, 300 without the determination of the exact distance between the subject 18 and the visual display device 104, 204, 304. In these one or more embodiments, neither a Snellen fraction nor a distance between the subject 18 and the visual display device 104, 204, 304 is determined in carrying out the steps of the dynamic visual acuity (DVA) testing procedure and the gaze stabilization testing procedure. Advantageously, in these one or more embodiments, the dynamic visual acuity (DVA) testing procedure and the gaze stabilization testing procedure are capable of being flexibly performed in a plurality of different site locations without a need to determine the distance between the subject 18 and the visual display device 104, 204, 304.

Advantageously, in these one or more embodiments, the exact distance between the subject or patient and the visual display device 104, 204, 304 does not need to be measured in order to run the test. That is, as long as the distance between the subject or patient and the visual display device 104, 204, 304 is approximated within plus or minus 25% of ten (10) feet, the exact distance need not be measured. Rather, the computing device 102, 202, 302 of the vision testing system 100 is specially programmed to utilize one, non-changing set of optotypes for all tests, regardless of the distance within the range of plus or minus 25% of ten (10) feet. In these one or more embodiments, this set of optotypes are the log MAR scale for ten (10) feet, but this distance does not matter because the difference between sizes (the ratio of the letters) is on the log MAR scale.

In these one or more embodiments, the exact distance between the subject or patient and the visual display device 104, 204, 304 does not need to be measured, and there is no need to change the size of the optotype based upon the distance, because the test carried out by the vision testing system 100, 200, 300 is only interested in the ratio of the letters. As illustrated in one or more of the exemplary screenshots depicted in the figures (e.g., in FIG. 19), a "relative log MAR" scale may be used to label all of the optotype sizes in order to emphasize the true log MAR difference between letter sizes, but to acknowledge that the absolute value is not absolute log MAR (i.e., when the distance between the subject 18 and the screen is not determined before the testing). Conversely, when the distance between the subject 18 and the screen is determined or measured before the testing, then the optotype size listed in the screenshots is denoted using a "log MAR" scale, rather than a "relative log MAR" scale, in order to signify that the actual visual acuity value is listed for the subject (e.g., during the static series of trials during the testing, a value denoted using a "log MAR" scale indicates that the actual static visual acuity of the subject is listed). As such, when the distance between the subject 18 and the screen is measured before the testing and the "log MAR" scale is used, the set of optotype sizes that are used during the testing are automatically adjusted by the specially-programmed computing device 102, 202, 302 in accordance with the measured distance (e.g., if the measured distance is eight (8) feet, a smaller set of optotypes are used as compared to those used for a measured distance of twelve (12) feet). That is, the greater the distance between the subject 18 and the screen, the larger the size of the optotypes that are used during the testing so as to account for the increased distance.

As one example of the manner in which relative log MAR values are used, suppose that a subject or patient is sitting at a distance of nine (9) feet from the output screen of the visual display device 104, 204, 304. The size parameter of the first threshold version of the visual display object during the first static series of trials (i.e., the threshold optotype during the SVA test) is 0.2 relative log MAR. The size parameter of the second threshold version of the visual display object during the third dynamic series of trials for both left and right rotation (i.e., the threshold optotype for both DVA left and right) is 0.5 relative log MAR. Thus, for both directions of head sweep, the subject or patient lost three (3) lines on the Snellen chart (or 0.3 log MAR of visual acuity).

As another example of the manner in which relative log MAR values are used, suppose that a subject or patient is sitting at a distance of five (5) feet from the output screen of the visual display device 104, 204, 304. The size parameter of the first threshold version of the visual display object during the first static series of trials (i.e., the threshold optotype during the SVA test) is −0.2 relative log MAR. The size parameter of the second threshold version of the visual display object during the third dynamic series of trials for both left and right rotation (i.e., the threshold optotype for both DVA left and right) is −0.1 relative log MAR. Thus, for both directions of head sweep, the subject or patient lost only one (1) line on the Snellen chart (or 0.1 log MAR of visual acuity).

3. Gaze Stabilization Testing Procedure

Figure 13A:
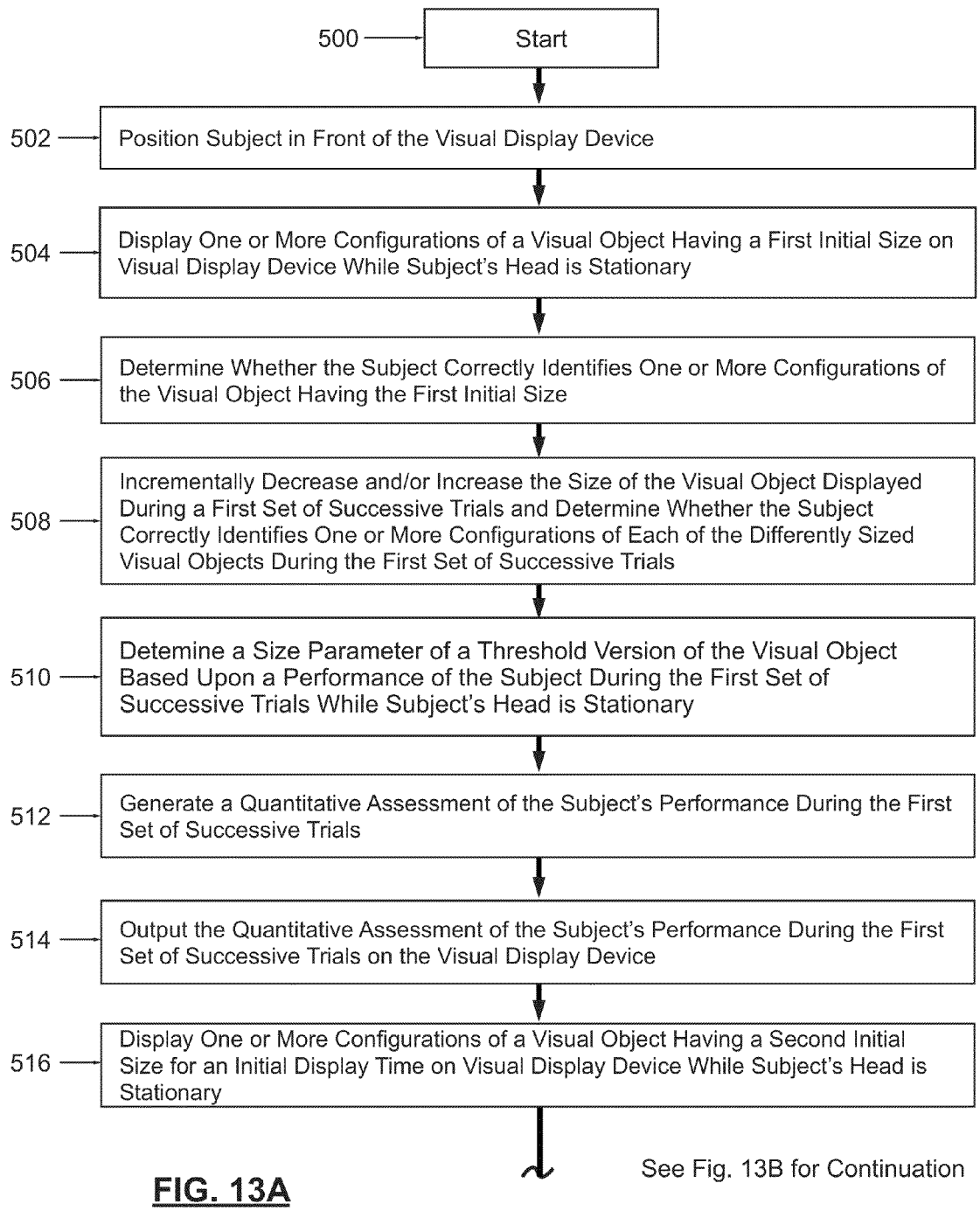
FIG. 13A is a partial flowchart illustrating a procedure for testing the gaze stabilization of a subject carried out by the systems illustrated in FIGS. 1-3, according to an embodiment of the invention.
Figure 13B:
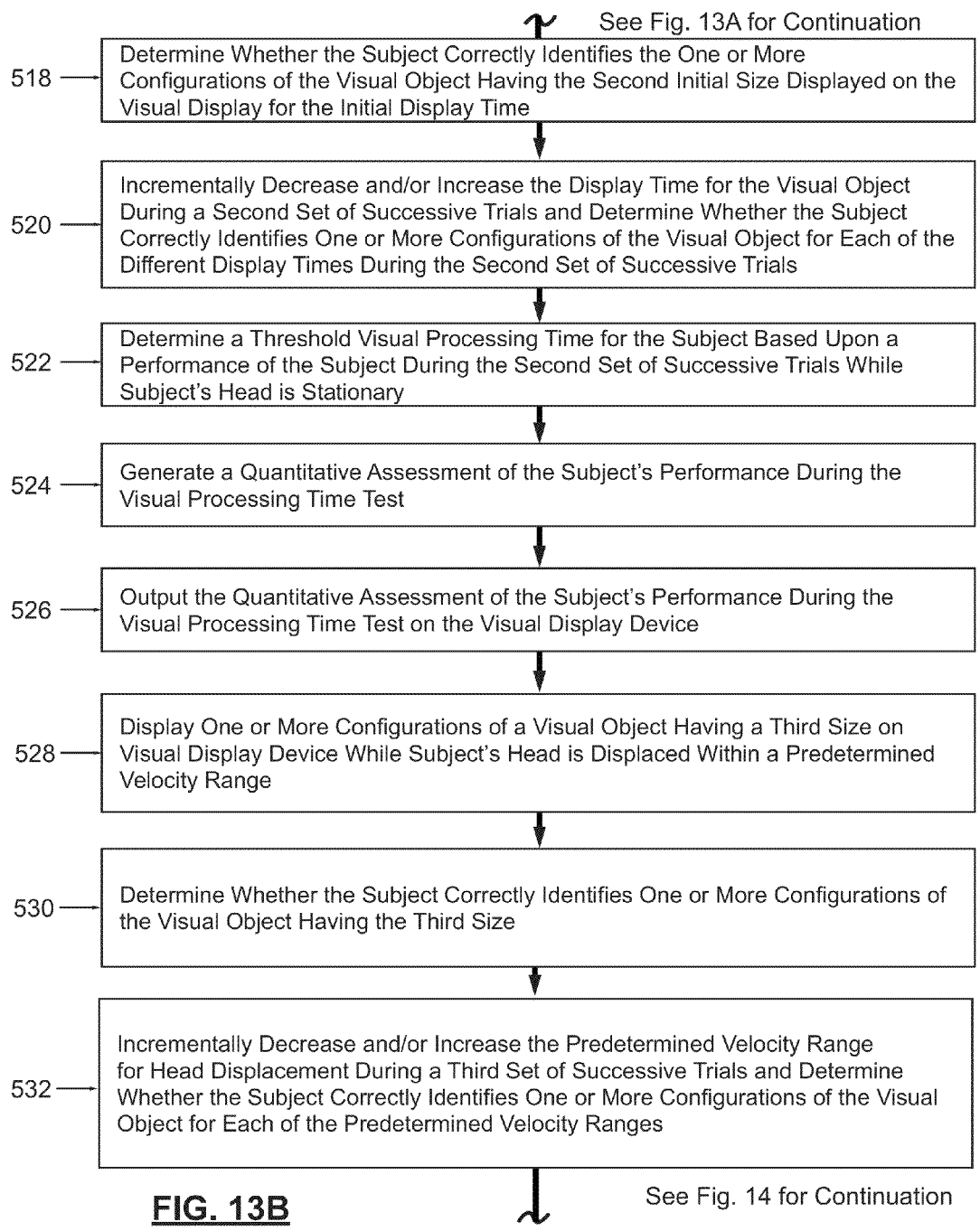
FIG. 13B is a continuation of the flowchart of FIG. 13A, which illustrates additional steps of the procedure for testing the gaze stabilization of a subject, according to an embodiment of the invention.
Figure 14:
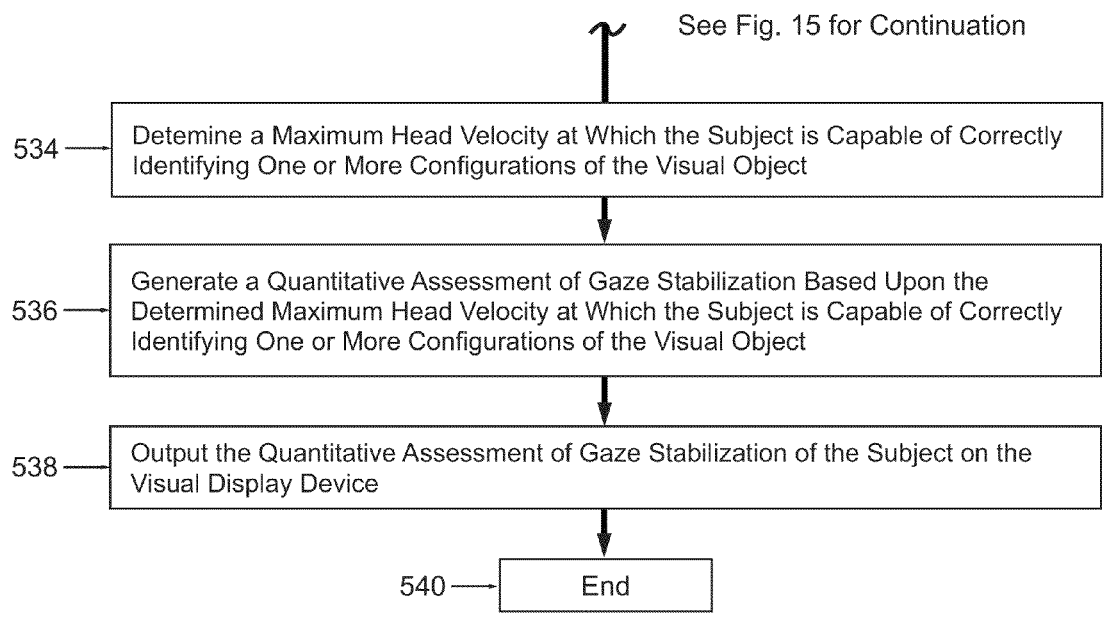
FIG. 14 is a continuation of the flowchart of FIG. 13B, which illustrates yet additional steps of the procedure for testing the gaze stabilization of a subject, according to an embodiment of the invention.

In accordance with an illustrative embodiment of the invention, a flowchart illustrating a procedure for testing the gaze stabilization of a subject carried out by the vision testing system 100, 200, 300 is set forth in FIGS. 13A, 13B, and 14. Referring initially to FIG. 13A, the procedure commences at 500, and in step 502, the subject is positioned in front of the output screen of the visual display device 104, 204, 304 such that a visual object 10 (e.g., an optotype) is visible to the subject 18. Then, while the subject 18 maintains a generally fixed position of his or her head 30 (i.e., keeping his or her head 30 as still as possible), one or more configurations of the visual object 10 having a first initial size are displayed on the output screen of the visual display device 104, 204, 304 in step 504 of FIG. 13A. As explained above with regard to dynamic visual acuity testing procedure, different configurations 10e, 10f, 10g, 10h of the Landolt C optotype may be displayed one-at-time on the output screen of the visual display device 104, 204, 304 (refer to FIG. 5). In an alternative exemplary embodiment, with reference to FIG. 6, different configurations 10'e, 10'f, 10'g, 10'h of the Tumbling E optotype may be displayed one-at-time on the output screen of the visual display device 104, 204, 304. In other exemplary embodiments, other suitable optotypes may be used in place of the Landolt C or the Tumbling E, such as letters of a recognized alphabet (e.g., the English alphabet).

During the first successive set of trials when the subject 18 maintains the generally fixed position of his or her head 30, the same exemplary operator screen image 600 of FIG. 15 and the same exemplary subject screen images 614, 626 of FIGS. 16 and 17, which were described above in conjunction with the dynamic visual acuity (DVA) test, may be used in conjunction with the first static set of successive set of trials during the gaze stabilization test (GST).

Now, turning again to FIG. 13A, in step 506 of FIG. 13A, the computing device or data processing device 102, 202, 302 determines whether or not the subject 18 correctly identifies one or more configurations (e.g., 10'e, 10'f, 10'g, 10'h) of the visual object 10 having the first initial size. For example, the subject 18 may be presented with one or more optotypes having the first initial size (e.g., a single optotype 10'g pointing down). This optotype 10'g is of the first initial size, which may be a size scale factor of 0.75. After the optotype is displayed to the subject 18, the subject 18 or the clinician 14 may utilize a user input device 24 (e.g., a wireless mouse) in order to transmit the response of the subject 18 to the computing device 102, 202, 302 (e.g., the wireless mouse may have four buttons, each of which corresponds to one of the four configurations of the optotype). After receiving the subject's responses, the computing device 102, 202, 302 is specially programmed to determine if the subject correctly determined the configuration of the optotype that was displayed on the output screen of the visual display device 104, 204, 304. For example, if the optotype 10'g of FIG. 6 was displayed on the screen, the subject 18 must indicate that optotype is pointing down to get the identification correct. Any other answer would be incorrect for this configuration of the optotype. Once the subject's answer or response is evaluated as to its correctness, the computing device 102, 202, 302 is specially programmed to record whether or not the subject 18 identified the optotype correctly. In one exemplary embodiment, if the subject 18 identifies the configuration of the optotype 10'g correctly, the computing device 102, 202, 302 is specially programmed to display one or more optotypes having a physical size that is smaller than the first optotype (e.g., the second trial may comprise one or more optotypes that have a size scale factor of 0.6875). For example, the second optotype may comprise the optotype 10'j in FIG. 6, which has a smaller size than the optotype 10'g in the middle row of FIG. 6. Conversely, if the subject 18 identifies the configuration of the first optotype 10'g incorrectly, the computing device 102, 202, 302 is specially programmed to display one or more optotypes having a physical size that is larger than the first optotype (e.g., the second optotype may have a size scale factor of 1.0). For example, in this case, the second optotype may comprise the optotype 10'c in the top row of FIG. 6, which has a larger size than the optotype 10'g, in the middle row of FIG. 6.

In this manner, as specified in step 508 of FIG. 13A, the computing device 102, 202, 302 is specially programmed to incrementally decrease or increase the size of the visual object on the output screen of the visual display device 104, 204, 304 during a first set of successive trials (e.g., during a maximum number 624 of fourteen (14) trials as indicated in FIGS. 16 and 17). For example, if the subject identifies the configuration of a particular-sized optotype correctly, the optotype size of the next optotype displayed on the screen is generally decreased, while the optotype size of the next optotype displayed on the screen is generally increased if the subject fails to correctly identify the configuration of the optotype correctly. In the illustrative embodiment, after each optotype is displayed on the output screen of the visual display device 104, 204, 304, the computing device 102, 202, 302 is specifically programmed to determine whether or not the subject 18 correctly identified the configuration of the optotype.

In step 510 of FIG. 13A, after the subject 18 has completed a predetermined number of trials of optotype identification, the computing device 102, 202, 302 is specifically programmed to determine a size parameter (e.g., a size scale factor) of a threshold version of the optotype based upon the performance of the subject 18 during the first set of successive trials during which the subject 18 maintained the generally fixed position of his or her head 30. For example, after the subject completes a series of fourteen (14) trials of optotype identification, the computing device 102, 202, 302 determines that the threshold version of the optotype has a size scale factor of 0.40. In one embodiment, the size scale factor of the first threshold version of the optotype is a calculated value that is determined using one or more statistical equations or formulas (e.g., using a Best-PEST algorithm as described hereinafter).

Then, in step 512 of FIG. 13A, the computing device 102, 202, 302 is specifically programmed to generate a quantitative assessment of the subject's performance during the first set of successive trials, and finally, in step 514 of FIG. 13A, to output the quantitative assessment of the subject's performance during the first set of successive trials on the output screen of the visual display device 104, 204, 304. For example, in an exemplary embodiment, the computing device 102, 202, 302 may generate a report 700, such as that explained above with regard to FIG. 26, in order to display the test results from the first set of successive trials.

After determining the size parameter of the first threshold version of the optotype in step 510 above, and generating and displaying the quantitative results in steps 512 and 514, the visual processing time of the subject 18 may be determined by the computing device 102, 202, 302 in steps 516-522 of FIGS. 13A and 13B. Because the purpose of determining visual processing time and the details regarding its determination were described above in conjunction with the steps of the dynamic visual acuity (DVA) procedure, these details of the visual processing time test need not be reiterated here. During the gaze stabilization procedure, the steps associated with the determination of the subject's processing time are performed in the same manner as explained above with regard to the dynamic visual acuity (DVA) test.

During the second successive set of trials when the visual processing time of the subject 18 is determined, the same exemplary operator screen image 628 of FIG. 18, and the same exemplary subject screen images 614, 626 of FIGS. 16 and 17, which were described above in conjunction with the dynamic visual acuity (DVA) test, may be used in conjunction with the second static set of successive set of trials during the gaze stabilization test (GST).

Turning again to the flowchart of FIG. 13A, it can be seen in step 516 that, while the subject 18 maintains a generally fixed position of his or her head 30 (i.e., keeping his or her head 30 as still as possible), one or more configurations of the visual object 10 are displayed on the output screen of the visual display device 104, 204, 304 for an initial display time (e.g., the optotype is displayed for sixty (60) milliseconds on the screen). For example, referring to FIG. 5, one or more configurations 10a, 10b, 10c, 10d of the Landolt C optotype may be displayed one-at-time on the output screen of the visual display device 104, 204, 304 for an initial display time. In an alternative exemplary embodiment, with reference to FIG. 6, one or more configurations 10'a, 10'b, 10'c, 10'd of the Tumbling E optotype may be displayed one-at-time on the output screen of the visual display device 104, 204, 304 for an initial display time. In other exemplary embodiments, other suitable optotypes may be used in place of the Landolt C or the Tumbling E, such as letters of a recognized alphabet (e.g., the English alphabet).

Now, with reference to FIG. 13B, in step 518, the computing device or data processing device 102, 202, 302 determines whether or not the subject 18 correctly identifies the one or more configurations (e.g., 10'a, 10'b, 10'c, 10'd) of the visual object 10' that is displayed on the visual display device 104, 204, 304 for the initial display time. For example, the subject 18 may be presented with a single optotype 10'b pointing down (see FIG. 6). After the optotype is displayed to the subject 18, the subject 18 or the clinician 14 may utilize a user input device 24 (e.g., a wireless mouse) in order to transmit the response of the subject 18 to the computing device 102, 202, 302 (e.g., the wireless mouse may have four buttons, each of which corresponds to one of the four configurations of the optotype). After receiving the subject's response, the computing device 102, 202, 302 is specially programmed to determine if the subject correctly determined the configuration of the optotype that was displayed on the output screen of the visual display device 104, 204, 304. For example, if the optotype 10'b of FIG. 6 was displayed on the screen, the subject 18 must indicate that optotype is pointing down to get the identification correct. Any other answer would be incorrect for this configuration of the optotype. Once the subject's answer or response is evaluated as to its correctness, the computing device 102, 202, 302 is specially programmed to record whether or not the subject 18 identified the optotype correctly. In one exemplary embodiment, if the subject 18 identifies the configuration of the optotype 10'b correctly, the computing device 102, 202, 302 is specially programmed to display one or more subsequent optotypes for a display time that is shorter than the initial display time (e.g., the second trial may display the subsequent optotype on the screen for a display time of only 50 milliseconds, rather than the 60 milliseconds that was used during the initial trial). Conversely, if the subject 18 identifies the configuration of the first optotype 10'b incorrectly, the computing device 102, 202, 302 is specially programmed to display one or more subsequent optotypes for a display time that is longer than the initial display time (e.g., the second trial may display the subsequent optotype on the screen for a display time of 70 milliseconds, rather than the 60 milliseconds that was used during the initial trial).

In this manner, as specified in step 520 of FIG. 13B, the computing device 102, 202, 302 is specially programmed to incrementally decrease or increase the display time for the visual object on the output screen of the visual display device 104, 204, 304 during a set of successive trials (e.g., during a maximum number 624 of fourteen (14) trials as indicated in FIGS. 16 and 17). During the set of successive trials, various configurations of the same-sized visual object may be displayed on the output screen of the visual display device 104, 204, 304 for identification by the subject. For example, if the subject identifies a configuration of the same-sized optotype correctly, the screen display time for next-displayed optotype is generally decreased, while the screen display time for next-displayed optotype is generally increased if the subject fails to correctly identify the configuration of the optotype correctly. In the exemplary embodiment, after each optotype is displayed on the output screen of the visual display device 104, 204, 304 for a particular display time, the computing device 102, 202, 302 is specifically programmed to determine whether or not the subject 18 correctly identified the configuration of the optotype. In step 522 of FIG. 13B, after the subject 18 has completed a predetermined number of trials of optotype identification, the computing device 102, 202, 302 is specifically programmed to determine a threshold visual processing time for the subject 18 based upon the performance of the subject 18 during the set of successive trials during which the subject 18 maintained the generally fixed position of his or her head 30. For example, after the subject completes a series of fourteen (14) trials of optotype identification, the computing device 102, 202, 302 determines that the visual processing time for the subject 18 is fifty-five (55) milliseconds. In one embodiment, the visual processing time for the subject 18 is a calculated value that is determined using one or more statistical equations or formulas (e.g., using a Best-PEST algorithm as described hereinafter).

Then, in step 524 of FIG. 13B, the computing device 102, 202, 302 is specifically programmed to generate a quantitative assessment of the subject's performance during the visual processing time test, and finally, in step 526 of FIG. 13B, to output the quantitative assessment of the subject's performance during the visual processing time test on the output screen of the visual display device 104, 204, 304. For example, in an exemplary embodiment, the computing device 102, 202, 302 may generate a report 720, such as that explained above with regard to FIG. 27, in order to display the test results from the visual processing time test.

In one or more embodiments, the dynamic visual acuity (DVA) test is performed together with the gaze stabilization test. In this case, when the two tests are performed as part of a consecutive series, the optotype identification trials performed while the subject's head 30 is in a generally fixed position (i.e., a static head condition) only need to be performed once. That is, these optotype identification trials performed during the first static set of successive trials and the second static set of successive trials performed in conjunction with the visual processing time test do not need to be repeated for both the dynamic visual acuity (DVA) test and the gaze stabilization test (GST). Thus, if steps 400 through 426 of the dynamic visual acuity (DVA) test were performed prior to the gaze stabilization test for a particular subject 18, there would be no need to perform steps 500 through 526 described above. Rather, after finishing the dynamic visual acuity (DVA) test, the testing procedure would immediately proceed with step 528 of the gaze stabilization test, as will be described hereinafter.

Referring again to FIG. 13B, the dynamic portion of the gaze stabilization test (GST) will be explained in detail. Initially, in step 528 of FIG. 13B, while the subject 18 displaces his or her head 30 at a velocity or speed within a predetermined range (e.g., between 85 and 120 degrees per second) as measured by the motion sensing device 28, one or more configurations of the optotype 10 having a third size are displayed in succession on the output screen of the visual display device 104, 204, 304. In one or more embodiments, the optotype of step 528 has a third size that is greater than the size of the threshold version of the optotype determined in step 510. In these embodiments, the size of the threshold version of the optotype determined in step 510 may be multiplied by a scale factor (e.g., 1.5 or 1.75) to arrive at the third size (i.e., the increased size) of the optotype to be used in step 528. For example, during this step, different configurations of the Landolt C optotype or tumbling E optotype having the third size may be displayed one-at-time on the output screen of the visual display device 104, 204, 304. In one exemplary embodiment, the displacement of the subject's head 30 may comprise rotating the subject's to the right, and to the left, about the yaw axis 66 of FIG. 10 (i.e., approximately in a horizontal plane). As described above, the subject 18 may rotate his or head 30 on his or her own, or alternatively, the clinician 14 may rotate the subject's head 30 with his or her hands 32 so that it is easier to maintain the subject's head rotation within the predetermined range (see e.g., FIGS. 1 and 3). In one embodiment, the optotype 10 is only displayed on the output screen of the visual display device 104, 204, 304 when the head 30 of the subject 18 is being rotated within an initial predetermined velocity range (e.g., between 40 and 60 degrees per second). In one or more embodiments, a Tumbling E optotype is displayed after the subject 18 gets the three (3) required head sweeps in a predetermined target velocity range (e.g., 40 deg./sec. to 60 deg./sec.). During the dynamic portion of the gaze stabilization test (GST), the computing device 102, 202, 302 may be specially programmed to randomly choose whether to display the optotype on a left head turn or a right head turn. Also, during the dynamic portion of the GST, the computing device 102, 202, 302 may be specially programmed to randomly choose the orientation of the optotype that is displayed on the screen. In one or more embodiments, the optotype size during the performance of the GST is determined by increasing the optotype size determined in conjunction with the first set of successive trials by two sizes (e.g., by adding 0.2 log MAR to the static visual acuity determined during the first set of successive trials). In addition, the first visual indicators 50, 51, and 60 described above in conjunction with FIGS. 7-9 may be used to ensure that the subject's head 30 is rotated within the predetermined velocity range, while the second visual indicator 48 may be used to ensure that the subject's head 30 is rotated within the prescribed range of motion (e.g., between 20 degrees to the left and 20 degrees to the right, or between 30 degrees to the left and 30 degrees to the right). Alternatively, the visual indicators described above in conjunction with FIGS. 21-24 may be displayed on the subject screen to ensure that the subject's head 30 is rotated within the predetermined velocity range.

After the optotype disappears during the dynamic portion of the gaze stabilization test (GST), the subject 18 stops shaking his or her head, and gives an orientation response to the operator or clinician identifying the orientation of the optotype that appeared on the screen. In one or more embodiments, approximately five-hundred (500) milliseconds after the operator or clinician records the orientation response of the subject 18, the next trial of the DVA test begins, wherein another optotype is displayed after the subject 18 gets the three (3) required head sweeps in the predetermined target velocity range. In one or more embodiments, if a trial of the dynamic portion of the GST lasts for more than eight (8) seconds, the computing device 102, 202, 302 may be specially programmed to interrupt the trial, and to automatically reduce the tested velocity to make the test trial easier to complete. Also, if the subject is unable to maintain the target head velocity for three (3) consecutive head sweeps, the computing device 102, 202, 302 may be specially programmed to automatically reduce the tested velocity, or to mark the trial as "unable to complete" or a "failed trial".

In alternative exemplary embodiments, rather than rotating his or her head 30 about the yaw axis 66 in FIG. 10, the subject 18 may alternatively rotate his or her head 30 about the pitch axis 62 (i.e., approximately in a vertical plane) or about the roll axis 64 (i.e., in a roll plane). The computing device 102, 202, 302 is specially programmed to allow the user to selectively choose any one of these rotational directions when performing the dynamic portion of the gaze stabilization test (GST).

Figure 25:
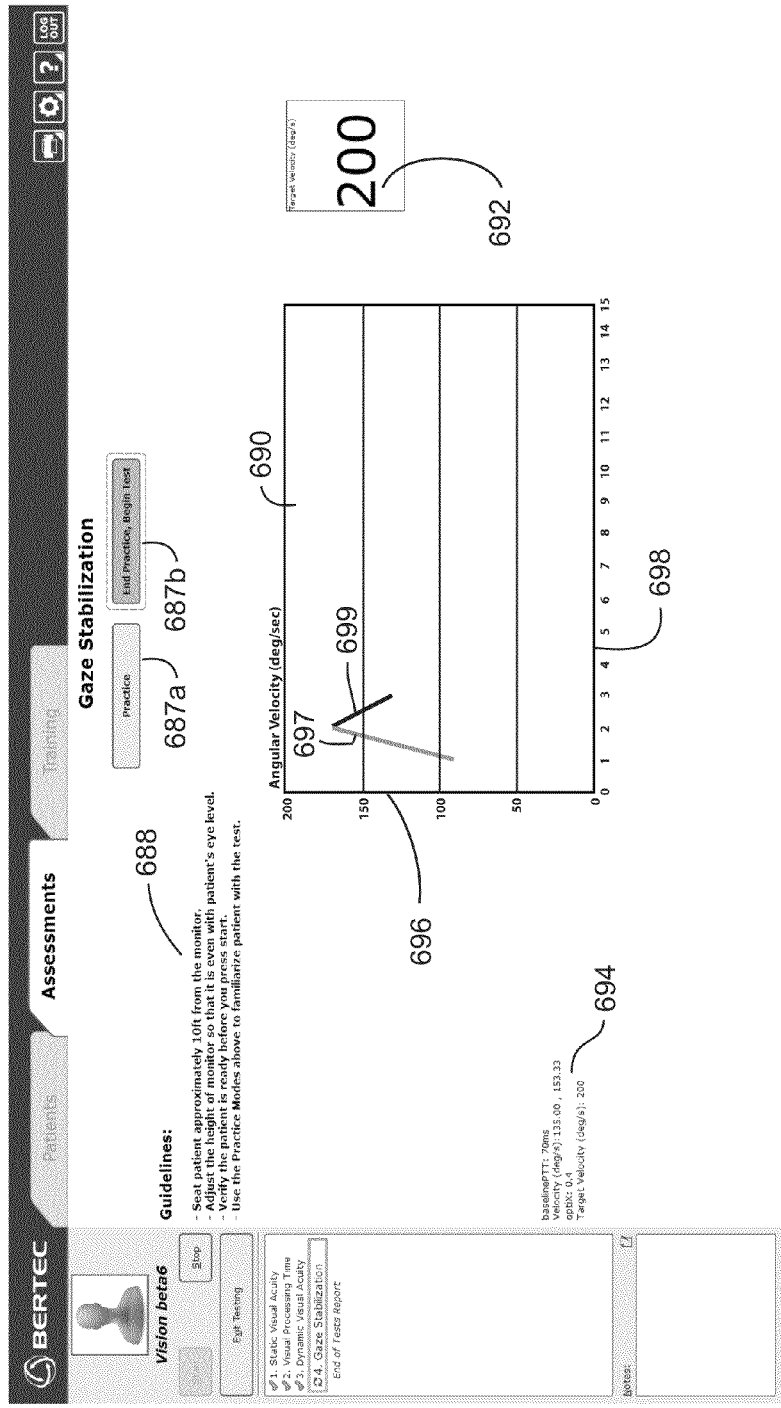
FIG. 25 is a fourth exemplary operator screen image of the visual display device, which may be displayed during the performance of a gaze stabilization test, according to an embodiment of the invention.

An exemplary operator or clinician screen image 686, which may be displayed on the visual display device 104, 204, 304 during the dynamic set of successive trials of the GST when the subject 18 rotates his or her head 30 within a predetermined angular velocity range, is shown in FIG. 25. In one or more embodiments, the computing device 102, 202, 302 may be specially programmed to generate the screen image 686 of FIG. 25 during the performance of this latter dynamic portion of the GST. As shown in FIG. 25, a set of on-screen virtual selection buttons 687a, 687b are provided at the top center of the screen for selecting one of: (i) a practice mode (by clicking on button 687a), and (ii) an actual GST test mode (by clicking on button 687b). With reference again to FIG. 25, it can be seen that testing guidelines 688 may be displayed at the top of the screen image 686. The testing guidelines may specify a distance or distance range (e.g., approximately ten (10) feet or between eight (8) and sixteen (16) feet) for the placement of the subject 18, visual display device height adjustment instructions, instructions regarding the readiness of the subject, and additional instructions regarding the practice modes (the practice modes of the gaze stabilization test will be described hereinafter). As additionally shown in FIG. 25, a graph 690 is also displayed in the center of the screen in order to visually illustrate the target angular velocity level for each successive trial while the subject's head 30 is rotated to the left and right. That way, the operator or clinician is able to easily view the subject's performance during the progression of the testing. As shown in FIG. 25, the y-axis 696 of the graph 690 is the target angular velocity (e.g., in degrees per second), while the x-axis 698 of the graph 690 is the trial number of the dynamic set of successive trials of the GST (i.e., while the head 30 of the subject 18 is rotated to the left and right). In the graph 690 of FIG. 25, it can be seen that stimulus curves 697, 699 are provided for both the right and left directions of head movement. Referring again to FIG. 25, it can be seen that the small box 692 on the right center of the clinician screen image 686 is configured to display the target angular velocity (e.g., in degrees per second) during the current trial of the dynamic GST testing procedure. Advantageously, the display of the target angular velocity in the small box 692 allows the clinician to quickly ascertain the subject's current performance level during the execution of the test. In one or more embodiments, after the optotype disappears from the subject screen, the computing device 102, 202, 302 is specially programmed to display the average head velocity for the trial in the small box 692. In the screen image 686 of FIG. 25, test summary data 694 is displayed below, and to the left of the graph 690 on the screen. For example, as shown in FIG. 25, the test summary data 694 may include the baseline visual processing time (i.e., baseline PTT in milliseconds), the current angular velocity threshold in degrees per second for both left and right head rotation, the optotype display size during the GST, and the current target angular velocity in degrees per second for the subject 18. In one or more embodiments, some values of the test summary data may be automatically completed as each of the test portions is successively completed (e.g., static visual acuity, visual processing time, dynamic visual acuity, and gaze stabilization).

Now, the practice mode of the gaze stabilization test (GST) will be described. In one or more embodiments, if the subject has not performed the dynamic visual acuity test prior to the gaze stabilization test, the subject may initially perform the position practice described above in conjunction with FIG. 20, and the velocity practice described above in conjunction with FIGS. 21-24. Alternatively, if the subject has already performed the dynamic visual acuity test prior to the gaze stabilization test, the practice for the GST may comprise only a single mode, namely the gaze stabilization test (GST) practice. In such a case, it is not necessary to repeat the position practice and the velocity practice because the subject will have just completed the DVA test and be familiar with the required head movement. The purpose of the GST practice is to allow the subject 18 to become familiar with varying his or her head velocity between trials. The GST practice mode is very similar to the DVA velocity practice described above in that the optotype 10 is always displayed at a large size in the same direction for an extended amount of time. However, during the GST practice mode, the computing device 102, 202, 302 may be specially programmed to vary the target head velocity for the subject 18 among the following three head velocities: (i) 120 degrees per second, (ii) 50 degrees per second, and (iii) 160 degrees per second to give the subject 18 an idea of a medium, slow, and fast target head velocity. Initially, during the GST practice mode, the subject 18 may be instructed to slowly begin moving his or her head 30 in the selected direction (i.e., left or right) with an initial head velocity of approximately twenty (20) degrees per second. Once, the subject becomes comfortable with rotating his or her head at a velocity of approximately twenty (20) degrees per second, the subject is instructed to gradually increase his or her rotational head velocity until the grayscale color of the outer circle on the screen matches the grayscale color of the inner circle on the screen. After the initial velocity of twenty (20) degrees per second, the subject rotates his or her head at an approximate practice velocity of fifty (50) degrees per second (i.e., in a range between 40 degrees per second and 60 degrees per second). During the GST practice mode, the computing device 102, 202, 302 may be specially programmed to randomly choose whether to display the optotype on a left head turn or a right head turn. Also, during the GST practice mode, the computing device 102, 202, 302 may be specially programmed to randomly choose the orientation of the optotype. In one or more embodiments, the optotype size during the performance of the GST practice mode is determined by increasing the optotype size determined in conjunction with the first set of successive trials by two sizes (e.g., by adding 0.2 log MAR to the static visual acuity determined during the first set of successive trials). Similar to the DVA practice mode described above, in one or more embodiments of the GST practice mode, approximately five-hundred (500) milliseconds after the operator or clinician records the orientation response of the subject 18, the next trial of the practice mode begins, wherein another optotype is displayed after the subject 18 gets the three (3) required head sweeps in the predetermined target velocity range. The practice mode may be continued until the subject 18 clearly understands the task that is being performed during the testing. The computing device 102, 202, 302 may be specially programmed to stop the practice mode when either the subject 18 or the operator presses the "ESC" key on the keyboard of the computing device 102, 202, 302.

Referring again to the flowchart of FIG. 13B, the computing device or data processing device 102, 202, 302 determines whether or not the subject 18 correctly identifies one or more configurations (e.g., 10'a, 10'b, 10'c, 10'd) of the visual object 10' having the third size in step 530. For example, the subject 18 may be presented with one or more optotypes have the third size (e.g., a single optotype 10'a pointing up). Unlike the dynamic set of trials performed during the dynamic visual acuity (DVA) test, each of the optotypes in the dynamic set of trials performed during the gaze stabilization test has the same physical size (i.e., each optotype has the same increased third size that is determined based upon the threshold size computed for the first series of trials carried out in steps 500-510 above). After each optotype in the trial is displayed to the subject 18, the subject 18 or the clinician 14 may utilize a user input device 24 (e.g., a wireless mouse) in order to transmit the response of the subject 18 to the computing device 102, 202, 302 (e.g., the wireless mouse may have four buttons, each of which corresponds to one of the four configurations of the optotype). After receiving each of the subject's responses, the computing device 102, 202, 302 is specially programmed to determine if the subject correctly determined the configuration of the optotype that was displayed on the output screen of the visual display device 104, 204, 304. For example, if the optotype 10'a of FIG. 6 was displayed on the screen, the subject 18 must indicate that optotype is pointing up to get the identification correct. Any other answer would be incorrect for this configuration of the optotype. Once the subject's answer or response is evaluated as to its correctness, the computing device 102, 202, 302 is specially programmed to record whether or not the subject 18 identified the optotype correctly. In one exemplary embodiment, if the subject 18 identifies the configuration of the optotype 10'a correctly, the computing device 102, 202, 302 is specially programmed to display a next optotype 10' while requiring the subject 18 to displace his or her within an increased velocity range (e.g., in a velocity range from 60 degrees per second to 80 degrees per second). Conversely, if the subject 18 identifies the configuration of the optotype 10'a incorrectly, the computing device 102, 202, 302 is specially programmed to display a next optotype 10' while requiring the subject 18 to displace his or her head 30 within a decreased velocity range (e.g., in a velocity range from 30 degrees per second to 40 degrees per second). While the velocity range in which the subject 18 is required to maintain his or her head 30 varies depending on whether the subject 18 correctly identifies the configuration of the optotype, the size of the optotype does not change. Rather, the same optotype size is used throughout the dynamic series of trials of the gaze stabilization test.

In this manner, as set forth in step 532 of FIG. 13B, the computing device 102, 202, 302 is specially programmed to incrementally decrease or increase the predetermined angular velocity or speed range within which the subject 18 is to displace his or her head 30 while identifying one or more configurations of the visual object (e.g., the optotype 10') on the output screen of the visual display device 104, 204, 304 during a third set of successive trials, the angular velocity or speed of the head 30 of the subject 18 being measured by the motion sensing device 28 (e.g., during a maximum number 676 of twenty-eight (28) trials as indicated in FIGS. 21-24). In one exemplary embodiment, the lower limit for the angular velocity or speed is 30 degrees per second, while the upper limit for the angular velocity or speed is 200 degrees per second (i.e., during the gaze stabilization testing procedure, the angular velocity or speed may be decreased down to 30 degrees per second and may be increased up to 200 degrees per second). For example, if the subject identifies the configuration of an optotype correctly, the predetermined velocity or speed range is generally increased, while the predetermined velocity or speed range is generally decreased if the subject fails to correctly identify the configuration of the optotype correctly. In the exemplary embodiment, after each optotype is displayed on the output screen of the visual display device 104, 204, 304, the computing device 102, 202, 302 is specifically programmed to determine whether or not the subject 18 correctly identified the configuration of the optotype.

In one or more embodiments, the computing device 102, 202, 302 is specially programmed with a high performance gaze stabilization testing mode to challenge subjects 18 having heightened dynamic vision capabilities (e.g., young, experienced athletes, etc.). When testing in the yaw direction (i.e., rotation 72 about the yaw axis 66—see FIG. 10), a user is able to select a high performance mode for the gaze stabilization test (GST). In the normal mode, the GST tests target head velocities ranging from thirty (30) degrees per second to two-hundred (200) degrees per second, inclusive. In contrast, the high performance GST mode increases this range from between seventy (70) degrees per second and three-hundred (300) degrees per second, inclusive. For example, the high performance GST mode should be selected for athlete testing and training. In the normal mode, thirty (30) degrees per second was selected as the lower limit of the range because it was found that thirty (30) degrees per second was lowest reasonable head velocity that an individual could maintain. In the normal mode, two-hundred (200) degrees per second was selected as the upper limit of the range because it was found that the ability of a "normal" person lies very close to a one-hundred and fifty (150) degrees per second limit. Therefore, in order to prevent the typical subject or patient from "maxing out" the normal GST test and having to spend time redoing the GST by performing a test using the high performance GST mode, an upper limit of two-hundred (200) degrees per second was selected to provide a "cushion" above one-hundred and fifty (150) degrees per second. During the performance of GST test, the computing device 102, 202, 302 may be specially programmed with a default resolution of ten (10) degrees per second for the angular velocity range. Although, the computing device 102, 202, 302 may be specially programmed to allow a user to adjust the resolution within the range of between ten (10) degrees per second and fifty (50) degrees per second in increments of ten (10) degrees per second. For example, with the default resolution setting, when performing the GST test, the angular velocity that is presented to the subject may be 30 degrees per second, 40 degrees per second, 50 degrees per second, 60 degrees per second, etc.

Also, in these one or more embodiments, the computing device 102, 202, 302 may be specially programmed with an option that allows a user (e.g., the operator or clinician) to switch to the high performance GST mode if a subject or patient has maxed out the normal GST test. For example, while a test is being performed in the normal GST mode, and a subject or patient gets two correct answers at the target head velocity level of 200 degrees per second, the computing device 102, 202, 302 may be specially programmed to generate a dialogue box that appears on the output screen of the visual display device 104, 204, 304 informing the operator or clinician that the subject or patient may be better suited for the high performance GST mode, and by giving the operator or clinician the option to end the normal GST early and switch to the high performance mode GST. If the operator or clinician chooses to switch the mode, the computing device 102, 202, 302 is specially programmed to restart the test in the high performance GST mode with the extended velocity range (i.e., between seventy (70) degrees per second and three-hundred (300) degrees per second). In contrast, if the operator or clinician declines to switch the mode, the test will continue where it left off in the normal GST mode.

In step 534 of FIG. 14, after the subject 18 has completed a predetermined number of trials of optotype identification (e.g., twenty-eight (28) total trials), the computing device 102, 202, 302 is specifically programmed to determine a maximum head velocity or head speed at which the subject is capable of correctly identifying one or more configurations of the visual object (i.e., the optotype). For example, after the subject 18 completes a series of twenty-eight (28) trials of optotype identification, the computing device 102, 202, 302 determines that the maximum angular velocity or head speed at which the subject is capable of correctly identifying one or more configurations of the optotype is 80 degrees per second.

In one or more embodiments, during the third set of successive trials during which the head 30 of the subject 18 is displaced, the maximum head velocity or head speed is determined by the computing device 102, 202, 302 for both the right and left directions of head movement about the yaw axis 66 of the FIG. 10 (e.g., fourteen (14) total trials are performed for left head rotation and fourteen (14) total trials are performed for right head rotation). That is, a first maximum head velocity or head speed is determined for the left rotation of the subject's head 30 about the yaw axis 66, and a second maximum head velocity or head speed is determined for the right rotation of the subject's head 30 about the yaw axis 66. For example, the maximum angular velocity or head speed for left rotation of the subject's head 30 may be 160 degrees per second, while the maximum angular velocity or head speed for right rotation of the subject's head 30 may be 140 degrees per second.

Next, in step 536 of FIG. 14, the computing device 102, 202, 302 is specifically programmed to generate a quantitative assessment of gaze stabilization based upon the computed maximum head velocity or head speed at which the subject 18 is capable of correctly identifying one or more configurations of the visual object (i.e., the optotype) on the output screen of the visual display device 104, 204, 304. Then, in step 538 of FIG. 14, the computing device 102, 202, 302 is specifically programmed to output the quantitative assessment of the gaze stabilization of the subject 18 on the output screen of the visual display device 104, 204, 304. The gaze stabilization testing procedure concludes at step 540 in FIG. 14.

Figure 29A:
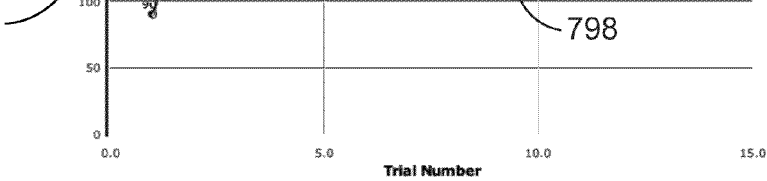
FIG. 29A is an eighth exemplary operator screen image of the visual display device, which illustrates a first part of an exemplary report generated by the vision testing system for displaying the results from a gaze stabilization test, according to an embodiment of the invention.

With reference to FIGS. 29A and 29B, the content of an exemplary test report for the third dynamic set of successive trials of the gaze stabilization test (GST) will be described. As shown in FIG. 29A, it can be seen that selected test parameters 788 may be displayed at the top of the screen image 786a. The test parameters 788 may include: (i) the direction of head rotation during dynamic portions of the DVA test (i.e., about the yaw axis 66 of FIG. 10), (ii) the approximate distance (e.g., in feet) between the subject and the visual display device 104, 204, 304, (iii) the optotype threshold sizes determined during the dynamic visual acuity (DVA) test (e.g., in log MAR or relative log MAR), (iv) optotype size during the GST test (e.g., in log MAR), (v) the optotype display time (e.g., as determined during the visual processing time test described above), (vi) the head velocity range used for the gaze stabilization test (e.g., in degrees per second), (vii)

whether or not progressive or corrective lenses (i.e., glasses or contact lens) are worn by the subject, and (viii) the maximum head velocities or head speeds (e.g., in degrees per second) that were computed for the left and right head movement directions of the subject 18 based upon his or her performance of the gaze stabilization test. As additionally shown in FIG. 29A, a patient results summary may also be displayed at the top of the screen image 786a, just below the test parameters summary. The patient results summary may include: (i) the static visual acuity of the subject (e.g., in log MAR or relative log MAR), (ii) the visual processing time of the subject (e.g., in milliseconds), (iii) the optoype threshold sizes for the left and right head rotational directions (e.g., in log MAR or relative log MAR) determined during the dynamic visual acuity (DVA) test, and (iv) the maximum or threshold head velocities for the left and right head rotational directions (e.g., in degrees per second) determined during the gaze stabilization test (GST).

Referring again to FIG. 29A, it can be seen that a graph 792 is displayed in the central portion of the screen in order to visually illustrate the subject's head rotational velocity for each successive trial while the subject's head 30 is rotated to the left and to the right. That way, the operator or clinician is able to easily observe any trends that occurred during the testing (i.e., consistent incorrect answers, consistent correct answers, etc.) and to easily assess whether or not the testing results follow a normal trend (e.g., transient response-type curve as explained hereinafter). Also, the graph 792 enables the operator or clinician to quickly and easily determine if the subject 18 achieved normal results during the gaze stabilization test (e.g., if the test results of the GST are normal, then each of the curves 796, 798 should resemble a typical transient response curve (e.g., a damped oscillation curve) where the amplitude at the beginning of the curve is relative large and oscillatory, but then settles down to a curve of much smaller amplitude and minimum oscillations (e.g., the latter portion of the curve approximates a straight line)). As shown in FIG. 29A, the y-axis 794 of the graph 792 is the target head velocity (e.g., in degrees per second), while the x-axis 795 of the graph 792 is the trial number of the dynamic set of successive of trials during the gaze stabilization test (GST) while the subject's head 30 is rotated to the left and to the right. In FIG. 29A, it can be seen that two curves 796, 798 are plotted on the graph 792. The first curve 796 is a plot of the test results for the left rotation of the head 30 of the subject 18, while the second curve 798 is a plot of the test results for the right rotation of the head 30 of the subject 18. At the beginning of the test, it can be seen that the two curves 796, 798 coincide with another (i.e., up to the fourth trial). However, after the fourth trial for both left and right head movement of the subject 18, the curves 796, 798 begin to deviate from one another (i.e., the target head velocity is generally greater for the left head rotation between the fourth trial and twelfth trial as compared to that tested for right head rotation). At the end of the dynamic set of successive trials of the GST, the curves 796, 796 are generally spaced apart from one another by a constant distance.

Now turning to FIG. 29B, it can be seen that a table 800 with the GST test results in tabular form may be displayed in the top half of the screen image 786b. As shown in FIG. 29B, the test data, which is plotted in the graph 792 of FIG. 29A, is presented in tabular form in table 800. The table 800 in FIG. 29B generally comprises a set of five (5) columns 802a, 804a, 806a, 808a, 810a on the left-hand side thereof, and another set of five (5) columns 802b, 804b, 806b, 808b, 810b on the right-hand side thereof. The five (5) columns 802a, 804a, 806a, 808a, 810a on the left-hand side correspond to the test results for the left rotation of the subject's head 30, while the five (5) columns 802b, 804b, 806b, 808b, 810b on the right-hand side correspond to the test results for the right rotation of the subject's head 30. The leftmost column 802a of the table 800 lists the trial number (i.e., trials nos. 1 through 12) for left head rotation, the next column 804a to the right lists the target angular head velocity (i.e., in degrees per second) for left head rotation, the next column 806a to the right lists the angular velocity achieved during the left head rotation trial, the next column 808a to the right lists the percentage of the velocity that was in the plane of movement (i.e., about the yaw axis 66) for left head rotation, and the final column 810a corresponding to left head rotation lists whether or not the subject or patient response was correct or incorrect for each of the left rotation trials in the table 800. Similarly, the leftmost column 802b corresponding to right head rotation in the table 800 lists the trial number (i.e., trials nos. 1 through 14) for right head rotation, the next column 804b to the right lists the target angular head velocity (i.e., in degrees per second) for right head rotation, the next column 806b to the right lists the angular velocity achieved during the right head rotation trial, the next column 808b to the right lists the percentage of the velocity that was in the plane of movement (i.e., about the yaw axis 66) for right head rotation, and the rightmost column 810b of the table 800 lists whether or not the subject or patient response was correct or incorrect for each of the right rotation trials in the table 800. Advantageously, the table 800 allows the operator or clinician to quickly ascertain the subject's numerical results for the dynamic set of trials performed during the GST test.

In one or more embodiments, a baseline visual processing time and static visual acuity value must have been previously stored in the computing device 102, 202, 302 in order to permit the subject 18 to perform the dynamic portion of the gaze stabilization test (GST). For example, if no baseline visual processing time and static visual acuity was previously determined on the day of the GST test, the subject 18 must first complete the static visual acuity testing and the visual processing time testing prior to performing the dynamic portion of the gaze stabilization test (GST).

In an alternative embodiment, in conjunction with steps 536 and 538 of FIG. 14, the computing device 102, 202, 302 may generate a graph or chart that graphically depicts the computed maximum angular velocity or head speed value or values. In the embodiments wherein the maximum angular velocity or head speed is determined for both the right and left directions of head movement of the subject 18, the graph or chart may graphically depict the computed maximum angular velocity or head speed for both the right and left movement directions. Advantageously, the graph or chart generated by the computing device 102, 202, 302 allows the clinician 14 to easily assess the maximum gaze stabilization (GST) velocity for both the right and left directions of movement. The computing device 102, 202, 302 may additionally generate another graph or chart that displays the maximum angular velocity or head speed symmetry for the left and right directions of movement in terms of a percentage difference between the right and left directions of movement. For example, the percentage difference between the right and left directions of movement may be computed using the following equation:

$$\%_{Difference} = \left( \frac{V_{max\_L} - V_{max\_R}}{V_{max\_L} + V_{max\_R}} \right) \quad (11)$$

where:

$V_{max\_L}$: maximum angular velocity for the left direction of head movement; and $V_{max\_R}$: maximum angular velocity for the right direction of head movement.

Then, after computing the percentage difference between the right and left directions of movement, the computing device 102, 202, 302 is specially programmed to output the graph or chart that graphically displays the percentage difference between the right and left directions of movement on the output screen of the visual display device 104, 204, 304. The gaze stabilization testing procedure concludes at step 540 in FIG. 14.

As briefly mentioned above, the stimulus levels during the successive trials of the vision testing may be determined by the computing device 102, 202, 302 by means of executing a parameter estimation algorithm (e.g., Best-PEST algorithm). In particular, during the first static set of successive trials during the dynamic visual acuity (DVA) test and the gaze stabilization test (GST), the optotype size selected for each trial, and the threshold optotype size computed in steps 410 and 510, may be computed using the parameter estimation algorithm (e.g., the Best-PEST algorithm). In one or more embodiments, the threshold optotype size of steps 410 and 510 may be computed by taking an average of the stimulus levels (i.e., optotype sizes) determined for a predetermined number of the final trials in the series (e.g., the optotype sizes determined for the last three or four trials in the series may be averaged to obtain the threshold optotype size). Similarly, during the visual processing time test performed in conjunction with DVA test and the GST, the optotype display time selected for each trial, and the threshold visual processing time computed in steps 422 and 522, may be computed using the parameter estimation algorithm (e.g., the Best-PEST algorithm). In one or more embodiments, the threshold visual processing time of steps 422 and 522 may be computed by taking an average of the stimulus levels (i.e., optotype display times) determined for a predetermined number of the final trials in the series (e.g., the optotype display times determined for the last three or four trials in the series may be averaged to obtain the threshold visual processing time). Also, during the dynamic set of successive trials performed in conjunction with the dynamic visual acuity (DVA) test, the optotype size selected for each trial, and the threshold optotype size computed in step 434, may be computed using the parameter estimation algorithm (e.g., the Best-PEST algorithm). In one or more embodiments, the threshold optotype size of step 434 may be computed by taking an average of the stimulus levels (i.e., optotype sizes) determined for a predetermined number of the final trials in the series (e.g., the optotype sizes determined for the last three or four trials in the series may be averaged to obtain the threshold optotype size). In addition, during the dynamic set of successive trials performed in conjunction with the gaze stabilization test (GST), the target head velocity range selected for each trial, and the maximum head velocity computed in step 534, may be computed using the parameter estimation algorithm (e.g., the Best-PEST algorithm). In one or more embodiments, the maximum head velocity in step 534 may be computed by taking an average of the stimulus levels (i.e., target velocities) determined for a predetermined number of the final trials in the series (e.g., the target velocities determined for the last three or four trials in the series may be averaged to obtain the maximum head velocity). As such, the parameter estimation computations performed by the computing device 102, 202, 302 will be explained in detail hereinafter.

Initially, the computing device 102, 202, 302 determines the psychometric function of the subject 18 as a function of the subject's stimulus level. In general terms, this psychometric function represents the relationship between the subject's visual acuity and the likelihood of the subject correctly identifying the optotype, which can be expressed by the following equation:

$$\Psi(x;\alpha,\beta,\gamma,\lambda)=\gamma+(1-\gamma-\lambda)f(x;\alpha,\beta) \qquad (12)$$

where:

ƒ(x): sigmoid function representing the probability of the subject correctly identifying the optotype as a function of the parameters: x, β, and β.

x: stimulus level presented to the subject (i.e., the optotype size, display time, or velocity);

α: determines the displacement of the sigmoid function along the abscissa;

β: determines the slope of the sigmoid function;

γ: represents the false alarm tendency of the subject (i.e., the chance level); and λ: represents the rate of attention lapses of the subject.

In the illustrative embodiment, the computing device 102, 202, 302 utilizes a logistic sigmoid function for the function ƒ(x), which is given by the following equation:

$$f(x) = \frac{1}{1 + e^{\beta(\alpha-x)}} \qquad (13)$$

As such, the computing device 102, 202, 302 utilizes the following logistic psychometric function in the vision testing threshold computations:

$$\Psi = \gamma + (1 - \gamma - \lambda)\left[\frac{1}{1 + e^{\beta(\alpha-x)}}\right] \qquad (14)$$

In above equation (14), α (which is often referred to as the midpoint) enables the displacement of the function along the stimulus-level axis. The α value corresponds to the average between γ and λ (i.e., $\Psi(\alpha)=(\gamma+\lambda)/2$). The β value is the function slope (i.e., the rate of change in the subject's performance with changes in stimulus level). As such, the greater the absolute value of β, the greater resultant steepness of the psychometric function. In addition, the function increases for positive values of β, while the function decreases for negative values of β.

In the vision tests described above, the computing device 102, 202, 302 determines the subject's threshold based upon a single point of the psychometric function. In the illustrative embodiment, the computational procedure executed by the computing device 102, 202, 302 is adaptive (i.e., the stimulus levels for the subject 18 are selected at the same time the testing is being performed, and the next stimulus level that is presented to the subject 18 is dependent on the subject's previous answer). Also, in the illustrative embodiment, the computational procedure executed by the computing device 102, 202, 302 is a parametric procedure.

In the illustrative embodiment, the computing device 102, 202, 302 executes a maximum likelihood procedure in order to determine the next stimulus level that is presented to the subject. The maximum likelihood procedure comprises two independent processes, namely a maximum likelihood estimation and a stimulus selection policy.

Initially, the maximum likelihood estimation process that is carried out by the computing device 102, 202, 302 will be explained. Prior to the commencement of the vision testing, several psychometric functions (i.e., hypotheses) are established. In the illustrative embodiment, the hypotheses have the same slope β, attentional lapse rate λ, and chance level γ, but differ in midpoint α so as to cover the range of stimulus levels at which subject's threshold is expected to lie within. In the illustrative embodiment, each of the vision tests begins with presenting the subject with a stimulus level that is above threshold. The subject's response is then collected and utilized by the computing device 102, 202, 302 to calculate the likelihood of each hypothesis. In particular, the likelihood is calculated by using the following equation:

$$L(H_j) = \prod_{i=1}^{n} H(x_i)^C [1 - H(x_i)]^W \tag{15}$$

where:
$L(H_j)$: is the likelihood of the jth hypothesized function; and
i: is the trial number.

The exponents C and W in equation (15) are equal to 1 and 0, respectively, when subject's response is correct, and to 0 and 1 otherwise (i.e., when subject's response is incorrect). The product in equation (15) can be simplified into a sum by means of a logarithmic transformation in the following manner:

$$L(H_j) = \sum_{i=1}^{n} C \log H(x_i) + W \log[1 - H(x_i)] \tag{16}$$

After the likelihood of each hypothesis has been calculated by the computing device 102, 202, 302, the highest likelihood hypothesis is selected using the maximum likelihood procedure. The highest likelihood hypothesis is the one having the greatest likelihood of resembling the actual subject's psychometric function. The highest likelihood hypothesis is identified by its midpoint α. The likelihood of the hypothesis is calculated by the computing device 102, 202, 302 after each trial of the vision testing. As such, even after the very first trial, a maximum likelihood estimate is returned by the executed procedure. Although, the maximum likelihood estimate returned after the first trial may be highly inaccurate. As the number of trials increases, the maximum likelihood estimate becomes increasingly more accurate. Consequently, the best maximum likelihood estimate is that which is generated by computing device 102, 202, 302 based upon an average of the last few trials in the series of trials (i.e., based upon an average of a last predetermined number of trials in the series, e.g., the last three or four trials).

After the most likely hypothesis has been determined using the maximum likelihood estimation process, the computing device 102, 202, 302 subsequently determines the level of the next stimulus that is to be presented to the subject. In the illustrative embodiment, the stimulus level at threshold is set to the p-target value. The maximum likelihood procedure even has sufficient information to determine the threshold level, which is used as the stimulus for the successive trial, after the completion of the first trial in the series. The most likely threshold for the subject is included in the most likely hypothesis. As given by the equation below, the threshold is the inverse function of the most likely hypothesis at the p-target:

$$\Psi^{-1}(p_t) = \alpha_j - \frac{1}{B} \ln\left(\frac{1-\gamma-\lambda}{p_t - \gamma} - 1\right) \tag{17}$$

where:
$p_t$: is the p-target.

Finally, with respect to the logistic function, the sweet point ($p_{sw}$) is calculated analytically by the computing device 102, 202, 302 using the following equation:

$$p_{sw} = \frac{2\gamma + 1 + \sqrt{1 + 8\gamma}}{3 + \sqrt{1 + 8\gamma}} \tag{18}$$

As such, in accordance with the above equation, if it is assumed that the subject does not produce any attention lapse, the sweet point ($p_{sw}$) depends exclusively on the chance level γ. Advantageously, the maximum likelihood procedure that is executed by the computing device 102, 202, 302 maximizes the use of all data that is available. That is, the data from all of the trials is used to estimate the subject's threshold.

In one or more alternative embodiments, a static visual acuity of the subject 18 is not determined in carrying out the steps of the dynamic visual acuity (DVA) testing procedure and the gaze stabilization testing procedure described above. That is, in these embodiments, the steps of the dynamic visual acuity (DVA) and gaze stabilization testing procedures are carried out without quantifying the static visual acuity of the subject 18 in terms of a static visual acuity number (e.g., a Snellen fraction, such as 20/20, 20/100, or 20/200). In these one or more embodiments, the static visual acuity of the subject 18 is not assessed using a Snellen eye chart, a Tumbling E eye chart, or a computerized version of the eye chart static visual acuity test. As such, in these one or more embodiments, there is no way to ascertain a quantifiable static visual acuity of the subject 18 because a recognized standard for determining the static visual acuity is not being used.

It is apparent from the above detailed description that the vision testing systems 100, 200, 300 and the methods performed thereby significantly advance the field of vision and vestibular assessment. For example, the vision testing systems 100, 200, 300 described herein greatly minimize subject or patient fatigue by utilizing visual and auditory feedback mechanisms that enable the subject or patient to more easily properly perform the DVA test and GST (e.g., the visual and auditory feedback mechanisms assist the subject in achieving the requisite angular velocity range and angular displacement range). As another example, the vision testing systems 100, 200, 300 described herein are capable of testing the dynamic visual acuity and gaze stabilization of a subject or patient in an extremely efficient manner by utilizing optimization threshold calculation procedures that quickly arrive at an accurate result. As yet another example, the ease of use of the vision testing systems 100, 200, 300 described herein is greatly enhanced by the use of innovative graphical user interfaces and improved hardware (e.g., a wireless motion sensing device 28).

Any of the features or attributes of the above described embodiments and variations can be used in combination with any of the other features and attributes of the above described embodiments and variations as desired.

Although the invention has been shown and described with respect to a certain embodiment or embodiments, it is apparent that this invention can be embodied in many different forms and that many other modifications and variations are possible without departing from the spirit and scope of this invention.

Moreover, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. A system for testing the vision of a subject, said system comprising:
   a motion sensing device, the motion sensing device configured to measure a velocity or speed of a head of a subject;
   a visual display device having an output screen, the visual display device configured to display one or more visual objects on the output screen so that the one or more visual objects are visible to the subject;
   a data processing device, the data processing device operatively coupled to the motion sensing device and the visual display device, the data processing device being specially programmed to:
      display one or more configurations of one or more visual objects having a first initial size on the output screen of the visual display device while the subject maintains a generally fixed position of his or her head;
      determine whether or not the subject correctly identifies the one or more configurations of the one or more visual objects having the first initial size;
      incrementally decrease and/or increase the size of the one or more visual objects on the output screen of the visual display device during a first set of successive trials, and determine whether or not the subject correctly identifies one or more configurations of each of the differently sized visual objects during the first set of successive trials while the subject maintains a generally fixed position of his or her head;
      determine a size parameter of a first threshold version of the one or more visual objects based upon a performance of the subject during the first set of successive trials during which the subject maintains the generally fixed position of his or her head, wherein the determination of the size parameter of the first threshold version of the one or more visual objects does not require the exact distance between the subject and the visual display device to be measured or determined;
      display one or more configurations of the one or more visual objects having a second initial size on the output screen of the visual display device while the subject's head undergoes displacement at a velocity or speed within a predetermined range as measured by the motion sensing device;
      determine whether or not the subject correctly identifies the one or more configurations of the one or more visual objects having the second initial size;
      incrementally decrease and/or increase the size of the one or more visual objects on the output screen of the visual display device during a second set of successive trials, and determine whether or not the subject correctly identifies one or more configurations of each of the differently sized visual objects during the second set of successive trials when the subject's head undergoes displacement at a velocity or speed within the predetermined range as measured by the motion sensing device;
      determine a size parameter of a second threshold version of the one or more visual objects based upon a performance of the subject during the second set of successive trials during which the subject's head undergoes displacement;
      compare the size parameter of the second threshold version of the one or more visual objects to the size parameter of the first threshold version of the one or more visual objects; and
      generate a quantitative assessment of dynamic visual acuity loss using the size parameters of the first and second threshold versions of the one or more visual objects.

2. The system according to claim 1, wherein the motion sensing device comprises at least one of an accelerometer, a gyroscope, and a magnetometer.

3. The system according to claim 1, wherein the motion sensing device is configured to be attached to the head of the subject by means of an adjustable band.

4. The system according to claim 1, further comprising a user input device, the user input device configured to output an input signal in response to a manipulation of the user input device by a system user, the user input device being operatively coupled to the data processing device; and
   wherein the determination of whether or not the subject correctly identifies the one or more configurations of the one or more visual objects during the first and second successive trials is based upon the input signal from the user input device.

5. The system according to claim 4, wherein the user input device comprises at least one of: (i) a mouse, (ii) a keyboard, (iii) a clicking device, (iv) a voice recognition device, and (v) a joystick.

6. The system according to claim 1, wherein the one or more visual objects displayed on the output screen of the visual display device comprise one or more optotypes, the one or more optotypes comprising at least one of: (i) a Tumbling E, (ii) a Landolt C, (iii) different letters of a recognized alphabet, and (iv) any other identifiable symbol.

7. The system according to claim 1, wherein the second initial size of the one or more visual objects is equal to the first initial size of the one or more visual objects or the second initial size of the one or more visual objects is larger than the first initial size of the one or more visual objects.

8. The system according to claim 1, wherein, during the second set of successive trials, the data processing device is further specially programmed to generate and display a visual indicator on the output screen of the visual display device that indicates whether or not the velocity or speed at which the subject's head is being displaced lies within the predetermined range.

9. The system according to claim 1, wherein the data processing device is further specially programmed to generate a practice mode for the second set of successive trials during which the subject's head undergoes displacement; and
   wherein, during the practice mode, the data processing device is specially programmed to generate and display a visual indicator on the output screen of the visual display device that indicates whether or not the head of the subject is being displaced within a prescribed range of motion.

10. The system according to claim 1, further comprising an auditory output device operatively coupled to the data processing device; and wherein, during the second set of successive trials, the data processing device is further specially programmed to generate and output an audible cue configured to assist the subject in achieving a head velocity or speed that lies within the predetermined range.

11. The system according to claim 1, wherein the one or more configurations of the one or more visual objects displayed on the output screen of the visual display device by the data processing device comprise a series of different visual objects displayed in succession on the output screen of the visual display device.

12. A system for testing the vision of a subject, said system comprising:
- a motion sensing device, the motion sensing device configured to measure a velocity or speed of a head of a subject;
- a visual display device having an output screen, the visual display device configured to display one or more visual objects on the output screen so that the one or more visual objects are visible to the subject;
- a data processing device, the data processing device operatively coupled to the motion sensing device and the visual display device, the data processing device being specially programmed to:
  - display one or more configurations of one or more visual objects having a first initial size on the output screen of the visual display device while the subject maintains a generally fixed position of his or her head;
  - determine whether or not the subject correctly identifies the one or more configurations of the one or more visual objects having the first initial size;
  - incrementally decrease and/or increase the size of the one or more visual objects on the output screen of the visual display device during a first set of successive trials, and determine whether or not the subject correctly identifies one or more configurations of each of the differently sized visual objects during the first set of successive trials while the subject maintains a generally fixed position of his or her head;
  - determine a size parameter of a first threshold version of the one or more visual objects based upon a performance of the subject during the first set of successive trials during which the subject maintains the generally fixed position of his or her head, wherein the determination of the size parameter of the first threshold version of the one or more visual objects does not require the exact distance between the subject and the visual display device to be measured or determined;
  - display one or more configurations of the one or more visual objects having a second initial size on the output screen of the visual display device while the subject's head undergoes displacement at a velocity or speed within a predetermined range as measured by the motion sensing device;
  - determine whether or not the subject correctly identifies the one or more configurations of the one or more visual objects having the second initial size;
  - incrementally decrease and/or increase the predetermined velocity or speed range within which the subject's head is to be displaced while the subject identifies one or more configurations of the one or more visual objects during a second set of successive trials, and determine whether or not the subject correctly identifies the one or more configurations of the one or more visual objects for each of the predetermined velocity or speed ranges during the second set of successive trials, the velocity or speed of the head of the subject being measured by the motion sensing device;
  - compute a maximum head velocity or head speed at which the subject is capable of correctly identifying one or more configurations of the one or more visual objects; and
  - generate a quantitative assessment of gaze stabilization based upon the computed maximum head velocity or head speed at which the subject is capable of correctly identifying one or more configurations of the one or more visual objects.

13. The system according to claim 12, wherein the one or more visual objects displayed on the output screen of the visual display device comprise one or more optotypes, the one or more optotypes comprising at least one of: (i) a Tumbling E, (ii) a Landolt C, (iii) different letters of a recognized alphabet, and (iv) any other identifiable symbol.

14. The system according to claim 12, wherein the second initial size of the one or more visual objects is equal to the first initial size of the one or more visual objects or the second initial size of the one or more visual objects is larger than the first initial size of the one or more visual objects.

15. The system according to claim 12, wherein, during the second set of successive trials, the data processing device is further specially programmed to generate and display a visual indicator on the output screen of the visual display device that indicates whether or not the velocity or speed at which the subject's head is being displaced lies within the predetermined range.

16. The system according to claim 12, further comprising an auditory output device operatively coupled to the data processing device; and wherein, during the second set of successive trials, the data processing device is further specially programmed to generate and output an audible cue configured to assist the subject in achieving a head velocity or speed that lies within the predetermined range.

17. The system according to claim 12, wherein the one or more configurations of the one or more visual objects displayed on the output screen of the visual display device by the data processing device comprise a series of different visual objects displayed in succession on the output screen of the visual display device.

18. A method for testing the vision of a subject, said method comprising the steps of:
- providing a motion sensing device, the motion sensing device configured to measure a velocity or speed of the head of the subject;
- providing a visual display device having an output screen, the visual display device configured to display one or more visual objects on the output screen so that the one or more visual objects are visible to the subject;
- providing a data processing device, the data processing device operatively coupled to the motion sensing device and the visual display device;
- positioning the subject in front of the output screen of the visual display device such that one or more visual objects are visible to the subject;
- displaying one or more configurations of the one or more visual objects having a first initial size on the output screen of the visual display device while the subject maintains a generally fixed position of his or her head;
- determining, by using the data processing device, whether or not the subject correctly identifies the one or more configurations of the one or more visual objects having the first initial size;
- incrementally decreasing and/or increasing the size of the one or more visual objects on the output screen of the visual display device using the data processing device during a first set of successive trials, and determining whether or not the subject correctly identifies one or more configurations of each of the differently sized visual objects during the first set of successive trials;

determining, by using the data processing device, a size parameter of a first threshold version of the one or more visual objects based upon a performance of the subject during the first set of successive trials during which the subject maintains the generally fixed position of his or her head, wherein the determination of the size parameter of the first threshold version of the one or more visual objects does not require the exact distance between the subject and the visual display device to be measured or determined;

displaying one or more configurations of the one or more visual objects having a second initial size on the output screen of the visual display device when the subject's head undergoes displacement at a velocity or speed within a predetermined range as measured by the motion sensing device;

determining, by using the data processing device, whether or not the subject correctly identifies the one or more configurations of the one or more visual objects having the second initial size;

incrementally decreasing and/or increasing the size of the one or more visual objects on the output screen of the visual display device using the data processing device during a second set of successive trials, and determining whether or not the subject correctly identifies one or more configurations of each of the differently sized visual objects during the second set of successive trials when the subject's head undergoes displacement at a velocity or speed within the predetermined range as measured by the motion sensing device;

determining, by using the data processing device, a size parameter of a second threshold version of the one or more visual objects based upon a performance of the subject during the second set of successive trials during which the subject's head undergoes displacement;

comparing, by using the data processing device, the size parameter of the second threshold version of the one or more visual objects to the size parameter of the first threshold version of the one or more visual objects;

generating, by using the data processing device, a quantitative assessment of dynamic visual acuity loss using the size parameters of the first and second threshold versions of the one or more visual objects;

outputting the quantitative assessment of dynamic visual acuity loss of the subject on the output screen of the visual display device;

displaying one or more configurations of the one or more visual objects having a third initial size on the output screen of the visual display device when the subject's head undergoes displacement within a predetermined range as measured by the motion sensing device, determining, by using the data processing device, whether or not the subject correctly identifies the one or more configurations of the one or more visual objects having the third initial size;

incrementally decreasing and/or increasing, using the data processing device, the predetermined velocity or speed range within which the subject's head is to be displaced while identifying one or more configurations of the one or more visual objects during a third set of successive trials, and determining whether or not the subject correctly identifies the one or more configurations of the one or more visual objects for each of the predetermined velocity or speed ranges during the third set of successive trials, the velocity or speed of the head of the subject being measured by the motion sensing device;

computing, by using the data processing device, a maximum head velocity or head speed at which the subject is capable of correctly identifying one or more configurations of the one or more visual objects;

generating, by using the data processing device, a quantitative assessment of gaze stabilization based upon the computed maximum head velocity or head speed at which the subject is capable of correctly identifying the one or more configurations of the one or more visual objects; and outputting the quantitative assessment of gaze stabilization of the subject on the output screen of the visual display device.

19. The method according to claim 18, wherein the one or more configurations of the one or more visual objects are only displayed on the output screen of the visual display device during the second set or third set of successive trials when the data processing device determines that the subject's head is undergoing displacement at a velocity or speed that lies within the predetermined range.

20. The method according to claim 18, further comprising a user input device, the user input device configured to output an input signal in response to a manipulation of the user input device by a system user, the user input device being operatively coupled to the data processing device; and wherein the method further includes the step of:

inputting a response of the subject regarding the configuration of the one or more visual objects into the user input device, outputting an input signal from the user input device that is indicative of the response of the subject, and transmitting the input signal of the user input device to the data processing device so that the data processing device is capable of determining whether or not the subject has correctly identified a configuration of the one or more visual objects based upon the response of the subject.

21. The method according to claim 20, wherein the user input device is configured to accept at least four different responses of a subject, each of the at least four different responses of the subject corresponding to a different configuration of the one or more visual objects.

22. The method according to claim 18, further comprising the step of:

computing, by using the data processing device, the logarithm of the ratio of the size parameter of the second threshold version of the one or more visual objects to the size parameter of the first threshold version of the one or more visual objects.

23. The method according to claim 22, wherein the computed logarithm comprises a base 10 logarithm.

24. The method according to claim 18, wherein a static visual acuity of the subject is not determined in carrying out the steps of the method.

25. The method according to claim 18, wherein an exact distance between the subject and the visual display device is not measured or determined in carrying out the steps of the method.

26. The method according to claim 18, wherein a Snellen fraction is not determined in carrying out the steps of the method.

* * * * *